(12) United States Patent
Wang et al.

(10) Patent No.: US 11,154,548 B2
(45) Date of Patent: Oct. 26, 2021

(54) MONOSUBSTITUTED OR POLYSUBSTITUTED AMPHIPHILIC HYPOCRELLIN DERIVATIVE, AND PREPARATION METHOD AND APPLICATION THEREOF

(71) Applicant: Technical Institute of Physics and Chemistry of the Chinese Academy of Sciences, Beijing (CN)

(72) Inventors: Pengfei Wang, Beijing (CN); Jiasheng Wu, Beijing (CN); Weimin Liu, Beijing (CN); Ying Gu, Beijing (CN); Jiechao Ge, Beijing (CN); Xiuli Zheng, Beijing (CN); Hongyan Zhang, Beijing (CN)

(73) Assignee: TECHNICAL INSTITUTE OF PHYSICS AND CHEMISTRY OF THE CHINESE ACADEMY OF SCIENCES, Beijing (CN)

( * ) Notice: Subject to any disclaimer, the term of this patent is extended or adjusted under 35 U.S.C. 154(b) by 45 days.

(21) Appl. No.: 15/769,789

(22) PCT Filed: Oct. 21, 2016

(86) PCT No.: PCT/CN2016/102832
§ 371 (c)(1),
(2) Date: Apr. 20, 2018

(87) PCT Pub. No.: WO2017/067497
PCT Pub. Date: Apr. 27, 2017

(65) Prior Publication Data
US 2018/0338965 A1 Nov. 29, 2018

(30) Foreign Application Priority Data

Oct. 21, 2015 (CN) .......................... 201510689088.7
Oct. 9, 2016 (CN) .......................... 201610880613.8
Oct. 13, 2016 (CN) .......................... 201610894129.0
Oct. 13, 2016 (CN) .......................... 201610894400.0

(51) Int. Cl.
| | |
|---|---|
| *C07C 217/12* | (2006.01) |
| *C07C 221/00* | (2006.01) |
| *C07C 225/22* | (2006.01) |
| *C07C 225/32* | (2006.01) |
| *C07C 229/18* | (2006.01) |
| *C07C 237/08* | (2006.01) |
| *C07C 239/14* | (2006.01) |
| *C07C 243/22* | (2006.01) |
| *C07C 249/02* | (2006.01) |
| *C07C 251/24* | (2006.01) |
| *C07C 251/56* | (2006.01) |

(Continued)

(52) U.S. Cl.
CPC .......... *A61K 31/473* (2013.01); *A61K 31/122* (2013.01); *A61K 31/135* (2013.01); *A61K 41/0057* (2013.01); *A61K 47/54* (2017.08); *A61K 47/543* (2017.08); *A61K 47/60* (2017.08); *A61P 35/00* (2018.01); *C07C 50/36* (2013.01); *C07C 217/12* (2013.01); *C07C 221/00* (2013.01); *C07C 225/22* (2013.01); *C07C 225/32* (2013.01); *C07C 229/18* (2013.01); *C07C 237/08* (2013.01); *C07C 239/14* (2013.01); *C07C 243/22* (2013.01); *C07C 249/02* (2013.01); *C07C 251/24* (2013.01); *C07C 251/56* (2013.01); *C07C 251/86* (2013.01); *C07C 309/69* (2013.01); *C07C 319/18* (2013.01); *C07C 323/25* (2013.01); *C07D 221/02* (2013.01); *C07D 241/38* (2013.01); *C07D 279/14* (2013.01); *C07D 487/08* (2013.01); *C07D 513/06* (2013.01); *C07D 513/16* (2013.01); *C07C 2601/04* (2017.05); *C07C 2601/08* (2017.05); *C07C 2601/14* (2017.05); *C07C 2601/18* (2017.05)

(58) Field of Classification Search
CPC ............................ C07C 2603/54; A61K 31/12
See application file for complete search history.

(56) References Cited

FOREIGN PATENT DOCUMENTS

| | | |
|---|---|---|
| CN | 1600780 | 3/2005 |
| WO | 03063901 | 8/2003 |

(Continued)

OTHER PUBLICATIONS

Liu et al. "Photodynamic Properties of a Bispyrrolecarboxamide-Modified Hypocrellin B: The Role of Affinity and Ascorbic Acid" J. Phys. Chem. B 2008, 112, 9959-9965. (Year: 2008).*

(Continued)

*Primary Examiner* — Amanda L. Aguirre
(74) *Attorney, Agent, or Firm* — Rankin, Hill & Clark LLP

(57) ABSTRACT

The invention discloses a monosubstituted or polysubstituted amphiphilic hypocrellin derivative, and a preparation method and application thereof. The amphiphilic hypocrellin derivative substituted by a group containing PEG, a quaternary ammonium salt or the like prepared according to the invention has an obvious red shift in its absorption spectrum and a significantly enhanced molar extinction coefficient, compared with the parent hypocrellin, can efficiently produce singlet state oxygen and other reactive oxygen species under photosensitive conditions; has different amphiphilicities and increased biocompatibility with cells or tissues by regulating its hydrophilicity and hydrophobicity; can meet the requirements of different clinical drugs, and solves the requirements of different drug delivery methods for different drug hydrophilicity and lipophilicity. Under identical conditions, the amphiphilic hypocrellin derivative photosensitizer according to the invention has higher ability to photodynamically inactivate tumor cells than the first and second generation commercial photosensitizers.

10 Claims, 6 Drawing Sheets

(51) Int. Cl.
| | |
|---|---|
| C07C 251/86 | (2006.01) |
| C07C 309/69 | (2006.01) |
| A61K 31/122 | (2006.01) |
| A61K 31/135 | (2006.01) |
| A61K 31/473 | (2006.01) |
| A61K 41/00 | (2020.01) |
| A61K 47/54 | (2017.01) |
| A61K 47/60 | (2017.01) |
| A61P 35/00 | (2006.01) |
| C07C 323/25 | (2006.01) |
| C07C 319/18 | (2006.01) |
| C07D 279/14 | (2006.01) |
| C07D 487/08 | (2006.01) |
| C07D 513/06 | (2006.01) |
| C07D 513/16 | (2006.01) |
| C07D 241/38 | (2006.01) |
| C07C 50/36 | (2006.01) |
| C07D 221/02 | (2006.01) |

(56) References Cited

FOREIGN PATENT DOCUMENTS

| WO | 2007016762 | 2/2007 | |
|---|---|---|---|
| WO | WO-2007016762 A1 * | 2/2007 | ........... C07C 229/74 |
| WO | WO-2008011707 A1 * | 1/2008 | ............. A61K 8/355 |
| WO | 2013020204 | 2/2013 | |

OTHER PUBLICATIONS

Paul, B.T. et al.; "Biophysical Evaluation of Two Red-shifted Hypocrellin B Derivatives as Novel PDT Agents" Journal of Photochemistry and Photobiology, B: Biology, 94(1), Dec. 31, 2009, pp. 38-44.

Yang, Hongying et al., "a Novel Photosensitizer, 2-butylamino-2-demethoxy-hypocrellin B(2-BA-2-DMHB)—its Photodynamic Ejects on HeLa Cells: Effiicacy and Apoptosis", Biochimica et Biophysica Acta, 1540(1), Dec. 30, 2001, pp. 22 and 24.

Deng, Hong et al., "Quantitative and Site-Directed Chemical Modification of Hypocrellins toward Direct Drug Delivery and Effective Photodynamic Activity", J. Med. Chem., 55(5), Feb. 21, 2012, p. 1910.

Zhang, Yang et al., "Novel Surfactant-like Hypocrellin Derivatives to Achieve Simultaneous Drug Delivery in Blood Plasma and Cell Uptake", Photochemistry and Photobiology, 83(6), Dec. 31, 2010, p. 668.

International Search Report filed in PCT/CN2016/102832 dated Jan. 9, 2018.

* cited by examiner

Formula I    Formula II though less than 1 mm tissue, and has weak light absorption capacity in the PDT window (600-900 nm). Over the past ten years, there have been many
MONOSUBSTITUTED OR POLYSUBSTITUTED AMPHIPHILIC HYPOCRELLIN DERIVATIVE, AND PREPARATION METHOD AND APPLICATION THEREOF

TECHNICAL FIELD

The present invention relates to the field of photosensitizer drug technology in photodynamic therapy, and in particular to a monosubstituted or polysubstituted amphiphilic hypocrellin derivative, and preparation method and application thereof.

BACKGROUND ART

As a rapidly developing novel technique for selectively treating vascular diseases in recent years, photodynamic therapy (PDT for short) has significant curative effects against various tumor diseases. PDT has become the fourth special oncotherapy method following surgery, radiotherapy and chemotherapy. It has advantages in its high efficiency and security, can continuously produce reactive oxygen species under light illumination, leads to injury or necrosis of pathologically changed cells and tissues, and has significant efficiency comparing with traditional drugs capable of killing a single target molecule only. PDT has the bidirectional selectivity of drug targeting and illumination locating, and reduces the damage to normal cells, thus ensuring the therapeutic safety. Besides the great achievements in clinical treatment of cancers, PDT is also used to treat non-tumorous diseases, such as various vasculopathies, pointed condyloma, psoriasis, nevus flammeus, rheumatoid arthritis and macular degeneration and so on. Moreover, PDT also has a significant effect on laser beautification.

The photosensitizer is a key factor affecting the therapeutic effect of PDT. Among the known photosensitizer drugs applied at present, the first generation photosensitizer for clinical use is a porphyrin photosensitive drug, and the second generation is a phthalocyanine photosensitive drug. Among these photosensitive drugs, the most prominent problem of porphyrin photosensitizers and phthalocyanine photosensitizers is the difficult separation of geometric isomers, as it is difficult to obtain a pure monocomponent compound. Moreover, its relatively complex composition does not contribute to subsequent drug metabolism or toxicological evaluation. Other photosensitive drugs, such as dihydroporphin, chlorophyll and perylenequinonoid, are still in a development stage. At present, China still falls far short of photosensitive drugs for clinical use, and is in urgent need of novel efficient photosensitive drugs to fill the shortage.

Since the 1980s, perylenequinonoid photosensitive drugs have been successively discovered, such as cercosporin, hypericin, elsiuochrome and hypocrellin, all of which have been validated to have anti-cancer activities. Among them, hypocrellin is a natural photosensitizer extracted from *Hypocrella bambusae*, which is a parasitical fungus living on arrow bamboo in the Yunnan Plateau of China, where the altitude is 4000 m. Natural hypocrellin mainly includes hypocrellin A (HA for short) and hypocrellin B (HB for short). In recent years, people have made detailed researches on hypocrellin, which has the basic conditions for becoming a photosensitive drug with superior performance. For example, it has strong absorption and a high molar extinction coefficient in the visible light area, and can efficiently produce singlet state oxygen under photosensitive conditions; it is a botanical drug, has good phototoxicity, low dark toxicity, fast in-vivo metabolism and clear chemical structure, and thus has broad application prospects (Xu Shangjie, Zhang Xiaoxing, Chen Shen et al., Research and progress of novel photodynamic drugs-hypocrellin derivatives, *Chinese Science Bulletin*, 2003, 48, 1005-1015). However, the main absorption wavelength range of hypocrellin is 450-550 nm. This wavelength can penetrate less than 1 mm tissue, and has weak light absorption capacity in the PDT window (600-900 nm). Over the past ten years, there have been many chemical modifications for hypocrellin, where ammonia-modified hypocrellin has an obvious red shift of the absorption wavelength to 600-700 nm, and significant increase of the molar extinction coefficient (Paul B., Babu M. S., Santhoshkumar T. R., et al. Biophysical evaluation of two red-shifted hypocrellin B derivatives as novel PDT agents, *J. Photochem. Photobiol.* B: 2009, 94, 38-44). The amino-modified hypocrellin has presented good properties of a photosensitive drug. However, the water solubility and biocompatibility of these photosensitizers still need to be further improved. The target of microvascular diseases is the heterogeneous dense microvascular network in the focal zone, and is sensitive to photodynamic effects. In case of PDT, drugs are usually delivered to pathologically changed tissues through the blood circulation system by way of intravenous injection. However, hypocrellin is a small lipophilic organic molecule with very low solubility in water. It will spontaneously accumulate in blood, and thus causes blockage of blood vessels in case of direct intravenous injection. A sulfo-substituted derivative (Liu X, Xie J, Zhang L Y, et al. Optimization of hypocrellin B derivative amphiphilicity and biological activity. *Chinese Sci Bull,* 2009, 54: 2045-2050) has better water solubility, but is negatively charged, and has a low cellular uptake rate due to mutual repulsion between it and a lot of negative charges in cells and tissues, thereby greatly reducing the photodynamic activity. Therefore, the designed photosensitive drug molecule shall not only meet the above light absorption conditions, but also have optimized amphiphilicity—not only satisfying the concentration requirements for intravenous injection, but also ensuring a high cellular uptake rate to improve the PDT effect.

Therefore, it is necessary to provide a monosubstituted or polysubstituted amphiphilic hypocrellin derivative that not only meets light absorption conditions, but also has optimized amphiphilicity, and a preparation method and application thereof.

SUMMARY OF THE INVENTION

A first object of the invention is to provide a monosubstituted or polysubstituted amphiphilic hypocrellin derivative; a second object of the invention is to provide a method for preparing the monosubstituted or polysubstituted amphiphilic hypocrellin derivative; and a third object of the invention is to provide an application of the monosubstituted or polysubstituted amphiphilic hypocrellin derivative.

In view of the fact that the existing hypocrellin derivative can neither meet light absorption conditions, nor meet optimized amphiphilicity, the invention proposes the technical solution of the invention. The applicant proposes to enhance the biocompatibility and regulate the hydrophilicity and hydrophobicity of the parent hypocrellin by modifying it with polyethylene glycol (PEG), a long chain quaternary ammonium salt or the like, or modifying it with PEG, a long chain quaternary ammonium salt and the like at the same time. These derivatives have different amphiphilicities and are not susceptible to pH changes. The applicant further proposes to modify hypocrellin by substitutions at $C_2$, $C_3$ or $C_{15}$ and at $C_4$, $C_5$, $C_8$ or $C_9$ for the first time, so that its maximum absorption red shifts to more than 700 nm, and it has a higher molar extinction coefficient, so as to improve its weak light absorption capacity in the phototherapy window. The results of photodynamic experiments show that such amphiphilic hypocrellin derivatives can meet the requirements of different clinical drugs, and solve the requirements of different drug delivery methods for different drug hydrophilicity and lipophilicity. The technical solution is first disclosed in the invention.

To achieve the first object, the invention adopts the following technical solution:

A monosubstituted or polysubstituted amphiphilic hypocrellin derivative is represented by general structural formula (I) or (II):

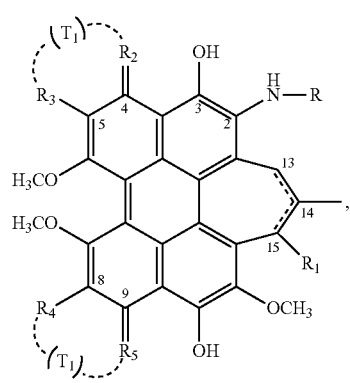

Formula (I)

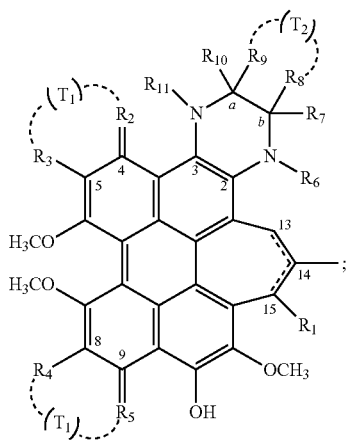

Formula (II)

in formulas (I) and (II), $T_1$ means that neither of two adjacent $R_2$ and $R_3$ nor two adjacent $R_4$ and $R_5$ are bonded, or just one group are bonded, or both of the two groups are bonded; when neither of two adjacent $R_2$ and $R_3$ and two adjacent $R_4$ and $R_5$ are bonded, $R_2$ and $R_5$ are oxygen, $R_3$ and $R_4$ are hydrogen; and when two adjacent $R_2$ and $R_3$ or two adjacent $R_4$ and $R_5$ are bonded, they form a substituted or unsubstituted six-membered heterocycle, wherein $T_1$ is a substituted or unsubstituted linker containing two carbon atoms, $R_2$ and $R_5$ are nitrogen, and $R_3$ and $R_4$ are sulfur; and the dashed lines at $C_{13}$, $C_{14}$ and $C_{15}$ mean that the double bond is at $C_{13}$=$C_{14}$ or $C_{14}$=$C_{15}$;

in formula (I), $R_1$ is —H, —COCH$_3$ or —C(CH$_3$)=N—R; in formula (II), $R_1$ is —H or —COCH$_3$; $T_2$ means that $R_8$ and $R_9$ are bonded or not bonded; and when $R_8$ and $R_9$ are bonded, they form a substituted or unsubstituted five-membered, six-membered or seven-membered ring, where $T_2$ is a substituted or unsubstituted linker containing one, two or three carbon atoms;

in formula (I), when neither of two adjacent $R_2$ and $R_3$ nor two adjacent $R_4$ and $R_5$ are bonded, $R_2$ and $R_5$ are oxygen, $R_3$ and $R_4$ are hydrogen, and $R_1$ is hydrogen, the double bond is located at $C_{13}$=$C_{14}$ or $C_{14}$=$C_{15}$ of the marked $C_{13}$, $C_{14}$ and $C_{15}$ in formula (I); and in formula (I), when neither of two adjacent $R_2$ and $R_3$ nor two adjacent $R_4$ and $R_5$ are bonded, $R_2$ and $R_5$ are oxygen, $R_3$ and $R_4$ are hydrogen, and $R_1$ is —COCH$_3$ or —C(CH$_3$)=N—R, the double bond is located at $C_{13}$=$C_{14}$ of the marked $C_{13}$, $C_{14}$ and $C_{15}$ in formula (I);

in formula (II), when none of two adjacent $R_2$ and $R_3$, two adjacent $R_4$ and $R_5$ and two adjacent $R_8$ and $R_9$ are bonded, $R_2$ and $R_5$ are oxygen, $R_3$ and $R_4$ are hydrogen, and $R_1$ is hydrogen, the double bond is located at $C_{13}$=$C_{14}$ or $C_{14}$=$C_{15}$ of the marked $C_{13}$, $C_{14}$ and $C_{15}$ in formula (II); and in formula (II), when none of two adjacent $R_2$ and $R_3$, two adjacent $R_4$ and $R_5$ and two adjacent $R_8$ and $R_9$ are bonded, $R_2$ and $R_5$ are oxygen, $R_3$ and $R_4$ are hydrogen, and $R_1$ is —COCH$_3$, the double bond is located at $C_{13}$=$C_{14}$ of the marked $C_{13}$, $C_{14}$ and $C_{15}$ in formula (II);

in formula (I), R is a substituent, and is a hydrophobic group, a hydrophilic group or different combinations thereof; the hydrophobic group comprises an alkyl, an alkenyl, an alkynyl, a cycloalkyl, a cycloalkenyl, a cycloalkynyl, a phenyl or a heterocycle; the hydrophilic group comprises a hydroxy, a carboxy, an ester group, an acylamino, a carboxy, a sulfo, a PEG-yl or a quaternary ammonium salt; and the substituent R is represented by general structural formula (III):

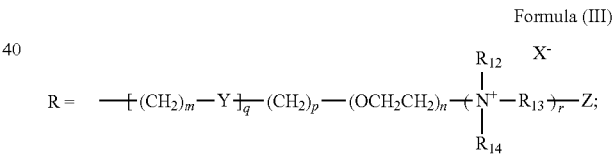

Formula (III)

in formula (III), $0 \leq m \leq 12$, $0 \leq n \leq 500$, $0 \leq p \leq 12$, $0 \leq q \leq 12$ and $0 \leq r \leq 1$; the m, n, p, q and r are zero or positive integers; Y is a linking group; Z is a terminal group; and (OCH$_2$CH$_2$)$_n$ is a polyethylene glycol unit;

in formula (III), the linking group Y is NH, O, S, a carboxylate, an amide, a sulfonate, an aryl, a heteroaryl, an alkyl containing 3-12 carbon atoms or a cycloalkyl containing 3-12 carbon atoms;

the aryl is a substituted or unsubstituted aryl; the heteroaryl is a substituted or unsubstituted heteroaryl; the alkyl containing 3-12 carbon atoms comprises a substituted or unsubstituted or heteroatom-containing alkene or alkyne; the cycloalkyl containing 3-12 carbon atoms comprises a substituted or unsubstituted or heteroatom-containing cycloalkane, cycloalkene or cycloalkyne; the heteroatom is oxygen, nitrogen or sulfur atom; the substituent is an alkyl containing 1-12 carbon atoms, an alkenyl containing 2-12 carbon atoms, an alkynyl containing 2-12 carbon atoms, a cycloalkyl containing 3-8 carbon atoms, an aryl or an aralkyl containing 6-12 carbon atoms; or an alkyl with a terminal group containing a hydroxy, a carboxy, a sulfo or a carboxylate; or an alkyl, alkenyl, alkynyl, cycloalkyl, aryl or aralkyl having a chain containing a heteroatom of oxygen, nitrogen or sulfur atom and 1-12 carbon atoms; or different combinations of the above substituents;

in formula (III), the terminal group Z is hydrogen, an alkyl containing 1-12 carbon atoms, an alkoxy containing 1-12 carbon atoms, a phenyl, a heterocycle, a hydroxy, a sulfhydryl, a carboxy, a sulfo or a pyridine salt;

in formula (III), when the terminal group Z is a pyridine salt, the substituent on the pyridine ring of the pyridine salt is at an ortho-position, a meta-position or a para-position; the pyridine salt is prepared by quaternization of pyridine and a halogenated hydrocarbon containing 1-12 carbon atoms of different chain lengths; and the anion of the pyridine salt is an acceptable anion in pharmaceutical preparations; in formula (III), three substituents $R_{12}$, $R_{13}$ and $R_{14}$ of a quaternary ammonium salt are independently or completely: an alkyl containing 1-12 carbon atoms, an alkenyl containing 2-12 carbon atoms, an alkynyl containing 2-12 carbon atoms, a cycloalkyl containing 3-8 carbon atoms, a cycloalkenyl containing 3-8 carbon atoms, an aryl or an aralkyl containing 6-12 carbon atoms; or an alkyl with a terminal group containing a hydroxy, a carboxy, a sulfo or a carboxylate; or an alkyl, alkenyl, alkynyl, cycloalkyl, aryl or aralkyl having a chain containing a heteroatom of oxygen, nitrogen or sulfur atom and 1-12 carbon atoms; or different combinations of the above substituents; and the anion $X^-$ of the quaternary ammonium salt is an acceptable anion in pharmaceutical preparations;

in formula (I), when neither of two adjacent $R_2$ and $R_3$, nor two adjacent $R_4$ and $R_5$ are bonded, $R_2$ and $R_5$ are oxygen, $R_3$ and $R_4$ are hydrogen, $R_1$ is —COCH$_3$, and the double bond is located at $C_{13}$=$C_{14}$, the substituent R in formula (I) does not comprise the following structure: —(CH$_2$)$_m$—NH—(CH$_2$)$_p$—Z, wherein 1≤m≤12, 0≤p≤12, and Z is a hydroxy, an alkoxy, a carboxylic acid or a carboxylate;

in formula (II), $R_6$-$R_{11}$ on the hypocrellinopiperazine ring are subject to the substituent R, which is a hydrophobic group, a hydrophilic group or different combinations thereof; the hydrophobic group comprises an alkyl, an alkenyl, an alkynyl, a cycloalkyl, a cycloalkenyl, a cycloalkynyl, a phenyl or a heterocyclic group; the hydrophilic group comprises a hydroxy, a carboxy, an ester group, an acylamino, a carboxy, a sulfo, a PEG-yl, a quaternary ammonium salt or a pyridine salt; and the substituent R is represented by general structural formula (III); and in formula (II), when none of two adjacent $R_2$ and $R_3$, two adjacent $R_4$ and $R_5$ and two adjacent $R_8$ and $R_9$ are bonded, $R_2$ and $R_5$ are oxygen, $R_3$ and $R_4$ are hydrogen, $R_1$ is hydrogen, and the double bond is located at $C_{14}$=$C_{15}$, at least one of carbon atoms a and b on the marked piperazine ring in formula (II) is a tertiary carbon atom; and in formula (II), when none of two adjacent $R_2$ and $R_3$, two adjacent $R_4$ and $R_5$, and two adjacent $R_8$ and $R_9$ are bonded, $R_2$ and $R_5$ are oxygen, $R_3$ and $R_4$ are hydrogen, $R_1$ is —COCH$_3$, and the double bond is located at $C_{13}$=$C_{14}$, at least one of the carbon atoms a and b on the marked piperazine ring in formula (II) is a tertiary carbon atom.

Preferably, the $T_1$ of the hypocrellin derivative in formula (I) is acyclically bonded, and is represented by general structural formula (IV):

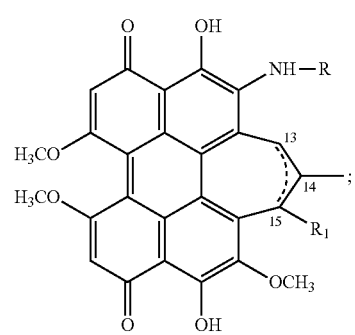

Formula (IV)

in formula (I), when neither of two adjacent $R_2$ and $R_3$ nor two adjacent $R_4$ and $R_5$ of hypocrellin are bonded, $R_2$ and $R_5$ are oxygen, and $R_3$ and $R_4$ are hydrogen, it is represented by general structural formula (IV);

in formula (IV), the substituent $R_1$ of the hypocrellin derivative is H, —COCH$_3$ or —C(CH$_3$)=N—R; when the $R_1$ is H, the double bond is located at $C_{13}$=$C_{14}$ or $C_{14}$=$C_{15}$ of the marked $C_{13}$, $C_{14}$ and $C_{15}$ in formula (IV); and when the $R_1$ is —COCH$_3$ or —C(CH$_3$)=N—R, the double bond is located at $C_{13}$=$C_{14}$ of the marked $C_{13}$, $C_{14}$ and $C_{15}$ in formula (IV); and preferably, the structure is shown in formula (IV-a)-formula (IV-d):

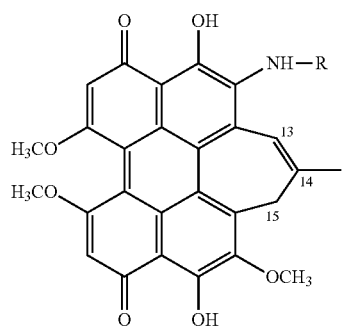

Formula (IV-a)

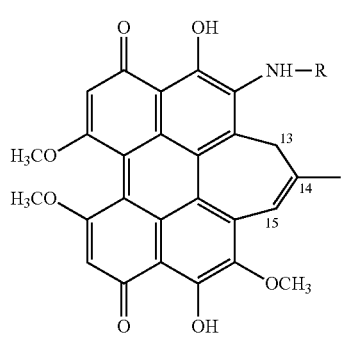

Formula (IV-b)

Formula (IV-c)

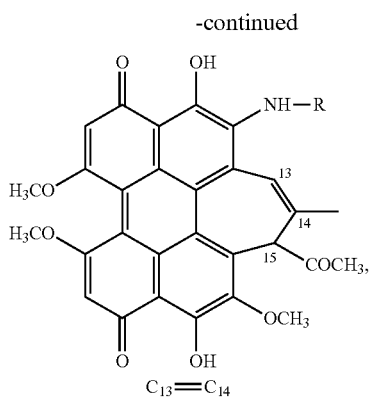

$C_{13}=C_{14}$

Formula (IV-d)

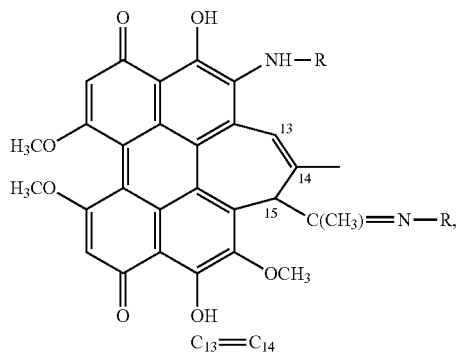

$C_{13}=C_{14}$ in formula (IV), the substituent R is represented by general structural formula (III), and is a hydrophobic group, a hydrophilic group or different combinations thereof; the hydrophobic group comprises an alkyl, an alkenyl, an alkynyl, a cycloalkyl, a cycloalkenyl, a cycloalkynyl, a phenyl or a heterocycle; the hydrophilic group comprises a hydroxy, a carboxy, an ester group, an acylamino, a carboxy, a sulfo, a PEG-yl or a quaternary ammonium salt; and in formula (IV), when the substituent $R_1$ is H and the double bond is located at $C_{14}=C_{15}$ (formula IV-b), or the $R_1$ is —$COCH_3$ and the double bond is located at $C_{13}=C_{14}$ (formula IV-c), the substituent R does not comprise the following structure: —$(CH_2)_m$—NH—$(CH_2)_p$—Z, wherein $1 \leq m \leq 12$, $0 \leq p \leq 12$, and Z is a hydroxy, an alkoxy, a carboxylic acid or a carboxylate.

Preferably, both of the $T_1$ and the $T_2$ in formula (II) are acyclically bonded, and is represented by general structural formula (V):

Formula (V)

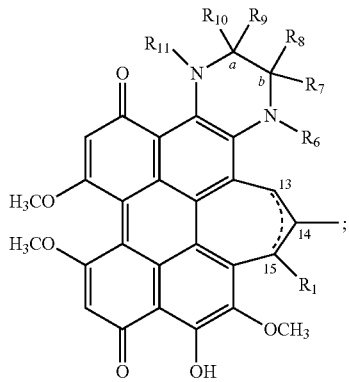

in formula (II), when none of two adjacent $R_2$ and $R_3$, two adjacent $R_4$ and $R_5$ and two adjacent $R_8$ and $R_9$ of hypocrellin are bonded, $R_2$ and $R_5$ are oxygen, and $R_3$ and $R_4$ are hydrogen, it is represented by general structural formula (V); in formula (V), the substituent $R_1$ of the piperazinohypocrellin derivative is H or —$COCH_3$; when the $R_1$ is H, the double bond is located at $C_{13}=C_{14}$ or $C_{14}=C_{15}$ of the marked $C_{13}$, $C_{14}$ and $C_{15}$ in formula (V); when the $R_1$ is —$COCH_3$, the double bond is located at $C_{13}=C_{14}$ of the marked $C_{13}$, $C_{14}$ and $C_{15}$ in formula (V); and preferably, the structure is shown in formula (V-a)-formula (V-c):

Formula (IV-a)

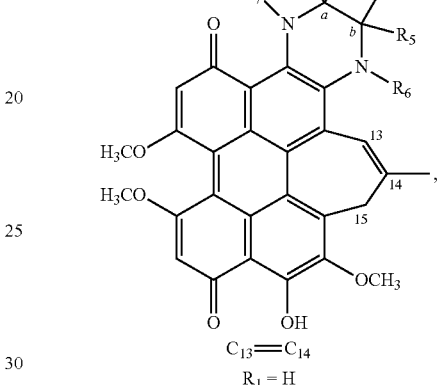

$C_{13}=C_{14}$
$R_1 = H$

Formula (IV-b)

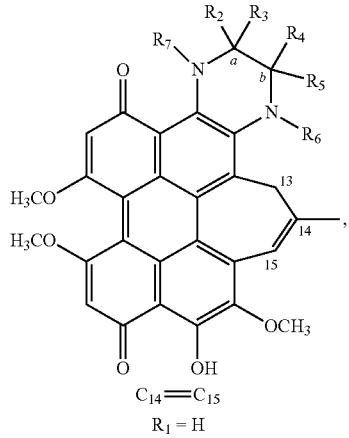

$C_{14}=C_{15}$
$R_1 = H$

Formula (IV-c)

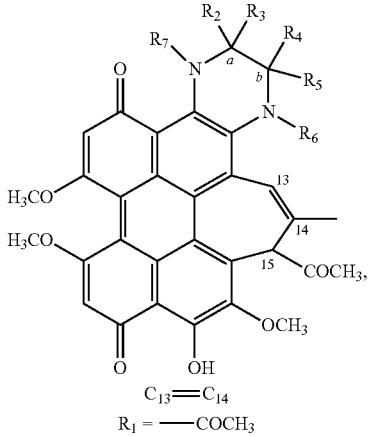

$C_{13}=C_{14}$
$R_1 =$ —$COCH_3$ in formula (V), when the substituent $R_1$ is H and the double bond is located at $C_{14}=C_{15}$, at least one of carbon atoms a and b on the marked piperazine ring in formula (V-b) is a tertiary carbon atom; and in formula (V), when the substituent $R_1$ is —$COCH_3$ and the double bond is located at $C_{13}=C_{14}$, at least one of the carbon atoms a and b on the marked piperazine ring in formula (V-c) is a tertiary carbon atom; and in formula (V), the substituents $R_6$-$R_{11}$ are defined similarly to the substituent R in formula (III), and are partially identical, or completely identical or completely different; and are hydrophobic groups, hydrophilic groups or different combinations thereof; the hydrophobic group comprises an alkyl, an alkenyl, an alkynyl, a cycloalkyl or a heterocycle; and the hydrophilic group comprises a hydroxy, a carboxy, an ester group, an ether group, an acylamino, a sulfo, a PEG unit or a quaternary ammonium salt.

Preferably, the $T_1$ in formula (I) and formula (II) is a substituted or unsubstituted linker containing two carbon atoms, and has a structure represented by formula (VI), wherein the substituents $R_{15}$-$R_{18}$ are independently or completely the substituent R in formula (III) according to claim 1; and preferably, the $R_8$, the $R_9$ and the $T_2$ in formula (II) form a substituted or unsubstituted five-membered, six-membered or seven-membered ring represented by formula (VII):

Formula (VI)

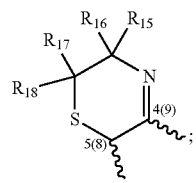

Formula (VII)

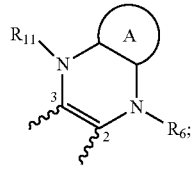

where ring A is a saturated or unsaturated five-membered, six-membered or seven-membered heterocycle or non-heterocycle, and the substituents thereon are independently or completely the substituent R in formula (III) according to claim 1; the substituent R is a hydrophobic group, a hydrophilic group or different combinations thereof; the hydrophobic group comprises an alkyl, an alkenyl, an alkynyl, a cycloalkyl, a cycloalkenyl, a cycloalkynyl, a phenyl or a heterocycle; and the hydrophilic group comprises a hydroxy, a carboxy, an ester group, an acylamino, a carboxy, a sulfo, a PEG-yl or a quaternary ammonium salt; and preferably, the linker Y in the substituent R in formula (III) is: —NH—; —O—; —S—; —COO—; CONH—; —$SO_3$—; —CH=CH—; —C≡C—; —$C_6H_4$— (phenyl); —$C_6H_3(CH_3)$—; —$C_6H_3(C_2H_5)$—; —$C_6H_3(OH)$—; —$C_6H_3(F)$—; —$C_6H_3(Cl)$—; —$C_6H_3(Br)$—; —$C_5H_3N$— (pyridyl); —$C_3H_4$-(cyclopropyl); —$C_4H_6$— (cyclobutyl); —$C_5H_8$— (cyclopentyl); —$C_5H_7(CH_3)$— (methylcyclopentyl); —$C_5H_7(OH)$— (hydroxycyclopentyl); —$C_6H_{10}$— (cyclohexyl); —$C_6H_9(CH_3)$— (methylcyclohexyl); —$C_6H_9(C_2H_5)$— (ethylcyclohexyl); —$C_6H_9(C_3H_7)$— (propylcyclohexyl); —$C_6H_9(C_4H_9)$— (butylcyclohexyl); —$C_6H_8$($CH_3$)$_2$-(dimethylcyclohexyl); —$C_6H_9(OH)$— (hydroxycyclohexyl); —$C_7H_{12}$— (cycloheptyl);

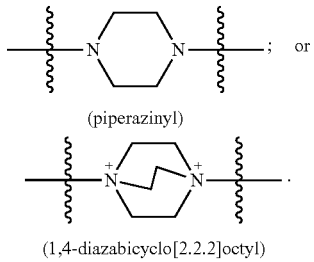

(piperazinyl)

(1,4-diazabicyclo[2.2.2]octyl)

Preferably, the terminal group Z in the substituent R in formula (III) is: —H; —$CH_3$; —$C_2H_5$; —$C_3H_7$; —$C_4H_9$; —$C_5H_{11}$; —$C_6H_{13}$; —$OCH_3$; —$OC_2H_5$; —$OC_3H_7$; —$OC_4H_9$; —$OC_5H_{11}$; —$OC_6H_{13}$; —$C_6H_5$; —$C_5H_4N$; —OH, —$NH_2$; —SH; —COOH; —$COOCH_3$; —$COOC_2H_5$; —$SO_3H$; —$C_5H_4N^+$; —$N^+(CH_3)_3$; —$N^+(C_2H_5)_3$; —$N^+(C_3H_7)_3$; —$N^+(C_4H_9)_3$; —$N^+(C_5H_{11})_3$; —$N^+(C_6H_{13})_3$; —$N^+(CH_3)_2(C_2H_5)$; —$N^+(CH_3)_2(C_3H_7)$; —$N^+(CH_3)_2(C_4H_9)$; —$N^+(CH_3)_2(C_5H_{11})$; —$N^+(CH_3)_2(C_6H_{13})$; —$N^+(CH_3)_2(C_7H_{15})$; —$N^+(CH_3)_2(C_8H_{17})$; —$N^+(CH_3)_2(C_9H_{19})$; —$N^+(CH_3)_2(C_{10}H_{23})$; —$N^+(CH_3)_2(C_{11}H_{23})$; —$N^+(CH_3)_2(C_{12}H_{25})$; —$N^+(C_2H_5)_2(C_3H_7)$; —$N^+(C_2H_5)_2(C_4H_9)$; —$N^+(C_2H_5)_2(C_5H_{11})$; —$N^+(C_2H_5)_2(C_6H_{13})$; —$N^+(C_2H_5)_2(C_7H_{15})$; —$N^+(C_2H_5)_2(C_8H_{17})$; —$N^+(C_2H_5)_2(C_9H_{19})$; —$N^+(C_2H_5)_2(C_{10}H_{23})$; —$N^+(C_2H_5)_2(C_{11}H_{23})$; —$N^+(C_2H_5)_2(C_{12}H_{25})$;

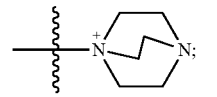

(1,4-diazabicyclo[2.2.2]octyl)

or a quaternary ammonium salt with a terminal group containing a hydroxy, a carboxy, a sulfo or a carboxylate.

Preferably, the substituent R is: —H; —$CH_3$; —$C_2H_5$; —$C_3H_7$; —$C_4H_9$; —$C_5H_{11}$; —$C_6H_{13}$; —$C_3H_6$; —$C_5H_9$ (cyclopentyl); —$C_6H_{11}$ (cyclohexyl); —$C_6H_{10}(CH_3)$ (methylcyclohexyl); —$C_6H_{10}(C_2H_5)$ (ethylcyclohexyl); —$C_6H_{10}(C_3H_7)$ (propylcyclohexyl); —$C_6H_{10}(C_4H_9)$ (butylcyclohexyl); —$C_6H_9(CH_3)_2$ (dimethylcyclohexyl); —$C_6H_{10}(OH)$ (hydroxycyclohexyl); —$C_7H_{12}$— (cycloheptyl); —$C_6H_5$; —$CH_2C_6H_5$; —$CH_2CH_2C_6H_5$; —$CH_2CH_2CH_2C_6H_5$; —$C_5H_4N$; —$CH_2C_5H_4N$; —$(CH_2)_2C_5H_4N$; —$(CH_2)_3C_5H_4N$; —$NH_2$; —$NHC_2H_5$; —$NHC_6H_5$; —$NHC_5H_4N$; —OH; —$CH_2CH_2OH$; —$CH_2CH_2$—$OCH_2CH_2$—OH; —$CH_2CH_2$—($OCH_2CH_2$)$_2$—OH; —$CH_2CH_2$—($OCH_2CH_2$)$_3$—OH; —$CH_2CH_2$—($OCH_2CH_2$)$_4$—OH; —$CH_2CH_2$—($OCH_2CH_2$)$_5$—OH; —$CH_2CH_2$—($OCH_2CH_2$)$_6$—OH; —$CH_2CH_2$—($OCH_2CH_2$)$_7$—OH; —$CH_2CH_2$—($OCH_2CH_2$)$_8$—OH; —$CH_2CH_2$—($OCH_2CH_2$)$_9$—OH; —$CH_2CH_2$—($OCH_2CH_2$)$_{10}$—OH; —$CH_2CH_2$—($OCH_2CH_2$)$_{11}$—OH; —$CH_2CH_2$—($OCH_2CH_2$)$_{12}$—OH; —$CH_2CH_2$—($OCH_2CH_2$)$_n$—OH [PEG with a molecular weight<30,000]; —$CH_2CH_2$—NH—$CH_2CH_2$—$OCH_2CH_2OH$; —$CH_2CH_2$—NH—$CH_2CH_2$—($OCH_2CH_2$)$_2$—OH; —$CH_2CH_2$—NH—$CH_2CH_2$—($OCH_2CH_2$)$_3$—OH; —$CH_2CH_2$—NH—$CH_2CH_2$—($OCH_2CH_2$)$_4$—OH; —$CH_2CH_2$—NH—$CH_2CH_2$—($OCH_2CH_2$)$_6$—OH; —$CH_2CH_2$—NH—$CH_2CH_2$—($OCH_2CH_2$)$_n$—OH; [PEG with a molecular weight<30,000]; —$(CH_2)_3$—OH; —$(CH_2)_3$—$OCH_2CH_2$—OH; —$(CH_3)_4$—$OCH_2CH_2$—OH; —$(CH_2)_3$—($OCH_2CH_2$)$_2$—

OH; —CH$_2$CH$_2$OCH$_3$; —CH$_2$CH$_2$—OCH$_2$CH$_2$—OCH$_3$; —CH$_2$CH$_2$—(OCH$_2$CH$_2$)$_2$—OCH$_3$; —CH$_2$CH$_2$—(OCH$_2$CH$_2$)$_4$—OCH$_3$; —CH$_2$CH$_2$—(OCH$_2$CH$_2$)$_6$—OCH$_3$; —CH$_2$CH$_2$—NH—CH$_2$CH$_2$—OCH$_2$CH$_2$OCH$_3$; —CH$_2$CH$_2$—NH—CH$_2$CH$_2$—(OCH$_2$CH$_2$)$_2$—OCH$_3$; —CH$_2$CH$_2$—NH—CH$_2$CH$_2$—(OCH$_2$CH$_2$)$_3$—OCH$_3$; —CH$_2$CH$_2$—NH—CH$_2$CH$_2$—(OCH$_2$CH$_2$)$_4$—OCH$_3$; —CH$_2$CH$_2$—NH—CH$_2$CH$_2$—(OCH$_2$CH$_2$)$_6$—OCH$_3$; —CH$_2$CH$_2$—NHCH$_2$CH$_2$—NH$_2$; —CH$_2$CH$_2$—(NHCH$_2$CH$_2$)$_2$—NH$_2$; —CH$_2$CH$_2$—(NHCH$_2$CH$_2$)$_3$—NH$_2$; —CH$_2$CH$_2$—NHCH$_2$CH$_2$—N(CH$_3$)$_2$; —CH$_2$CH$_2$—(NHCH$_2$CH$_2$)$_2$—N(CH$_3$)$_2$; —CH$_2$CH$_2$—(NHCH$_2$CH$_2$)$_3$—N(CH$_3$)$_2$; —CH$_2$CH$_2$—SH; —CH$_2$CH$_2$—S—CH$_2$CH$_2$OH; —CH$_2$CH$_2$—S—CH$_2$CH$_2$—OCH$_2$CH$_2$—OH; —CH$_2$CH$_2$—S—CH$_2$CH$_2$—(OCH$_2$CH$_2$)$_2$—OH; —CH$_2$CH$_2$—S—CH$_2$CH$_2$—SH; —CH$_2$CH$_2$—(SCH$_2$CH$_2$)$_2$—SH; —CH$_2$CH$_2$—(SCH$_2$CH$_2$)$_3$—SH; —CH$_2$CH$_2$—(SCH$_2$CH$_2$)$_4$—SH; —CH$_2$CH$_2$—SO$_3$H; —(CH$_2$CH$_2$O)$_2$—SO$_3$H; —CH$_2$CO$_2$H; —CH$_2$CH$_2$CO$_2$H; —CH$_2$CH$_2$CH$_2$CO$_2$H; —CH$_2$CH$_2$CH$_2$CO$_2$H; —CH$_2$—C(=O)—OCH$_2$CH$_2$—OH; —CH$_2$CH$_2$—C(=O)—OCH$_2$CH$_2$—OH; —CH$_2$CH$_2$—C(=O)—(OCH$_2$CH$_2$)$_2$—OH; —CH$_2$CH$_2$—C(=O)—(OCH$_2$CH$_2$)$_3$—OH; —CH$_2$CH$_2$—C(=O)—(OCH$_2$CH$_2$)$_4$—OH; —CH$_2$CH$_2$—C(=O)—(OCH$_2$CH$_2$)$_6$—OH; —CH$_2$CH$_2$—C(=O)—(OCH$_2$CH$_2$)$_n$—OH [PEG with a molecular weight<30,000]; —(CH$_2$)$_3$—C(=O)—OCH$_2$CH$_2$—OH; —(CH$_2$)$_3$—C(=O)—(OCH$_2$CH$_2$)$_2$—OH; —(CH$_2$)$_3$—C(=O)—(OCH$_2$CH$_2$)$_4$—OH; —(CH$_2$)$_3$—C(=O)—(OCH$_2$CH$_2$)$_6$—OH; —(CH$_2$)$_3$—C(=O)—(OCH$_2$CH$_2$)$_n$—OH [PEG with a molecular weight<30,000]; —(CH$_2$)$_4$—C(=O)—OCH$_2$CH$_2$—OH; —(CH$_2$)$_4$—C(=O)—(OCH$_2$CH$_2$)$_2$—OH; —(CH$_2$)$_4$—C(=O)—(OCH$_2$CH$_2$)$_4$—OH; —(CH$_2$)$_4$—C(=O)—(OCH$_2$CH$_2$)$_n$—OH [PEG with a molecular weight<30,000]; —(CH$_2$)$_5$—C(=O)—OCH$_2$CH$_2$—OH; —(CH$_2$)$_5$—C(=O)—(OCH$_2$CH$_2$)$_2$—OH; —(CH$_2$)$_5$—C(=O)—(OCH$_2$CH$_2$)$_4$—OH; —(CH$_2$)$_5$—C(=O)—(OCH$_2$CH$_2$)$_6$—OH; —(CH$_2$)$_5$—C(=O)—(OCH$_2$CH$_2$)$_n$—OH [PEG with a molecular weight<30,000]; —CH$_2$CH$_2$—SO$_2$—OCH$_2$CH$_2$—OH; —CH$_2$CH$_2$—SO$_2$—(OCH$_2$CH$_2$)$_2$—OH; —CH$_2$CH$_2$—SO$_2$—(OCH$_2$CH$_2$)$_4$—OH; —CH$_2$CH$_2$—SO$_2$—(OCH$_2$CH$_2$)$_6$—OH; —CH$_2$CH$_2$—SO$_2$—(OCH$_2$CH$_2$)$_n$—OH [PEG with a molecular weight<30,000]; —(CH$_2$)$_3$—SO$_2$—OCH$_2$CH$_2$—OH; —(CH$_2$)$_3$—SO$_2$—(OCH$_2$CH$_2$)$_2$—OH; —(CH$_2$)$_3$—SO$_2$—(OCH$_2$CH$_2$)$_4$—OH; —(CH$_2$)$_3$—SO$_2$—(OCH$_2$CH$_2$)$_6$—OH; —(CH$_2$)$_3$—SO$_2$—(OCH$_2$CH$_2$)$_n$—OH [PEG with a molecular weight<30,000]; —(CH$_2$)$_4$—SO$_2$—OCH$_2$CH$_2$—OH; —(CH$_2$)$_4$—SO$_2$—(OCH$_2$CH$_2$)$_2$—OH; —(CH$_2$)$_4$—SO$_2$—(OCH$_2$CH$_2$)$_4$—OH; —(CH$_2$)$_4$—SO$_2$—(OCH$_2$CH$_2$)$_6$—OH; —(CH$_2$)$_4$—SO$_2$—(OCH$_2$CH$_2$)$_n$—OH [PEG with a molecular weight<30,000]; —(CH$_2$)$_5$—SO$_2$—OCH$_2$CH$_2$—OH; —(CH$_2$)$_5$—SO$_2$—(OCH$_2$CH$_2$)$_2$—OH; —(CH$_2$)$_5$—SO$_2$—(OCH$_2$CH$_2$)$_4$—OH; —(CH$_2$)$_5$—SO$_2$—(OCH$_2$CH$_2$)$_6$—OH; —(CH$_2$)$_5$—SO$_2$—(OCH$_2$CH$_2$)$_n$—OH [PEG with a molecular weight<30,000]; —CH$_2$—C(=O)NH—CH$_2$CH$_2$—OCH$_2$CH$_2$—OH; —(CH$_2$)$_2$—C(=O)NH—CH$_2$CH$_2$—(OCH$_2$CH$_2$)$_2$—OH; —(CH$_2$)$_2$—C(=O)NH—CH$_2$CH$_2$—(OCH$_2$CH$_2$)$_3$—OH; —(CH$_2$)$_2$—C(=O)NH—CH$_2$CH$_2$—(OCH$_2$CH$_2$)$_6$—OH; —(CH$_2$)$_2$—C(=O)NH—CH$_2$CH$_2$—(OCH$_2$CH$_2$)$_n$—OH [PEG with a molecular weight<30,000]; —(CH$_2$)$_3$—C(=O)NH—CH$_2$CH$_2$—OCH$_2$CH$_2$—OH; —(CH$_2$)$_3$—C(=O)NH—CH$_2$CH$_2$—(OCH$_2$CH$_2$)$_2$—OH; —(CH$_2$)$_3$—C(=O)NH—CH$_2$CH$_2$—(OCH$_2$CH$_2$)$_6$—OH; —(CH$_2$)$_3$—C(=O)NH—CH$_2$CH$_2$—(OCH$_2$CH$_2$)$_n$—OH [PEG with a molecular weight<30,000]; —CH$_2$CH$_2$—N$^+$(CH$_3$)$_3$; —CH$_2$CH$_2$—N$^+$(C$_2$H$_5$)$_3$; —CH$_2$CH$_2$—N$^+$(C$_3$H$_7$)$_3$; —CH$_2$CH$_2$—N$^+$(C$_4$H$_9$)$_3$; —CH$_2$CH$_2$—N$^+$(C$_5$H$_{11}$)$_3$; —CH$_2$CH$_2$—N$^+$(C$_6$H$_{13}$)$_3$; —(CH$_2$)$_3$—N$^+$(CH$_3$)$_3$; —(CH$_2$)$_4$—N$^+$(CH$_3$)$_3$; —(CH$_2$)$_5$—N$^+$(CH$_3$)$_3$; —(CH$_2$)$_6$—N$^+$(CH$_3$)$_3$; —CH$_2$CH$_2$—N$^+$(CH$_3$)$_2$(C$_2$H$_5$); —CH$_2$CH$_2$—N$^+$(CH$_3$)$_2$(C$_3$H$_7$); —CH$_2$CH$_2$—N$^+$(CH$_3$)$_2$(C$_4$H$_9$); —CH$_2$CH$_2$—N$^+$(CH$_3$)$_2$(C$_5$H$_{11}$); —CH$_2$CH$_2$—N$^+$(CH$_3$)$_2$(C$_6$H$_{13}$); —CH$_2$CH$_2$—N$^+$(CH$_3$)$_2$(C$_7$H$_{15}$); —CH$_2$CH$_2$—N$^+$(CH$_3$)$_2$(C$_8$H$_{17}$); —CH$_2$CH$_2$—N$^+$(CH$_3$)$_2$(C$_9$H$_{19}$); —CH$_2$CH$_2$—N$^+$(CH$_3$)$_2$(C$_{10}$H$_{21}$); —CH$_2$CH$_2$—N$^+$(CH$_3$)$_2$(C$_{11}$H$_{23}$); —CH$_2$CH$_2$—N$^+$(CH$_3$)$_2$(C$_{12}$H$_{25}$); —(CH$_2$)$_3$—N$^+$(CH$_3$)$_3$; —(CH$_2$)$_3$—N$^+$(CH$_3$)$_2$(C$_2$H$_5$); —(CH$_2$)$_3$—N$^+$(CH$_3$)$_2$(C$_3$H$_7$); —(CH$_2$)$_3$—N$^+$(CH$_3$)$_2$(C$_4$H$_9$); —(CH$_2$)$_3$—N$^+$(CH$_3$)$_2$(C$_5$H$_{11}$); —(CH$_2$)$_3$—N$^+$(CH$_3$)$_2$(C$_6$H$_{13}$); —(CH$_2$)$_3$—N$^+$(CH$_3$)$_2$(C$_{10}$H$_{21}$); —(CH$_2$)$_3$—N$^+$(CH$_3$)$_2$(C$_{12}$H$_{25}$); —(CH$_2$)$_4$—N$^+$(CH$_3$)$_3$; —(CH$_2$)$_4$—N$^+$(CH$_3$)$_2$(C$_2$H$_5$); —(CH$_2$)$_4$—N$^+$(CH$_3$)$_2$(C$_4$H$_9$); —(CH$_2$)$_4$—N$^+$(CH$_3$)$_2$(C$_6$H$_{13}$); —(CH$_2$)$_4$—N$^+$(CH$_3$)$_2$(C$_8$H$_{17}$); —(CH$_2$)$_4$—N$^+$(CH$_3$)$_2$(C$_{10}$H$_{21}$); —(CH$_2$)$_5$—N$^+$(CH$_3$)$_3$; —(CH$_2$)$_5$—N$^+$(CH$_3$)$_2$(C$_2$H$_5$); —(CH$_2$)$_5$—N$^+$(CH$_3$)$_2$(C$_3$H$_7$); —(CH$_2$)$_5$—N$^+$(CH$_3$)$_2$(C$_4$H$_9$); —(CH$_2$)$_5$—N$^+$(CH$_3$)$_2$(C$_5$H$_{11}$); —(CH$_2$)$_5$—N$^+$(CH$_3$)$_2$(C$_6$H$_{13}$); —(CH$_2$)$_5$—N$^+$(CH$_3$)$_2$(C$_{10}$H$_{21}$); —(CH$_2$)$_5$—N$^+$(CH$_3$)$_2$(C$_{12}$H$_{25}$); —(CH$_2$)$_6$—N$^+$(CH$_3$)$_3$; —(CH$_2$)$_6$—N$^+$(CH$_3$)$_2$(C$_2$H$_5$); —(CH$_2$)$_6$—N$^+$(CH$_3$)$_2$(C$_4$H$_9$); —(CH$_2$)$_6$—N$^+$(CH$_3$)$_2$(C$_6$H$_{13}$); —(CH$_2$)$_6$—N$^+$(CH$_3$)$_2$(C$_8$H$_{17}$); —(CH$_2$)$_6$—N$^+$(CH$_3$)$_2$(C$_{10}$H$_{21}$); —(CH$_2$)$_6$—N$^+$(CH$_3$)$_2$(C$_{12}$H$_{25}$); —(CH$_2$)$_4$—N$^+$(C$_2$H$_5$)$_3$; —(CH$_2$)$_4$—N$^+$(C$_2$H$_5$)$_2$(C$_3$H$_7$); —(CH$_2$)$_4$—N$^+$(C$_2$H$_5$)$_2$(C$_4$H$_9$); —(CH$_2$)$_4$—N$^+$(C$_2$H$_5$)$_2$(C$_5$H$_{11}$); —(CH$_2$)$_4$—N$^+$(C$_2$H$_5$)$_2$(C$_6$H$_{13}$); —(CH$_2$)$_4$—N$^+$(C$_2$H$_5$)$_2$(C$_8$H$_{17}$); —(CH$_2$)$_4$—N$^+$(C$_2$H$_5$)$_2$(C$_{10}$H$_{21}$); or —(CH$_2$)$_4$—N$^+$(C$_2$H$_5$)$_2$(C$_{12}$H$_{25}$).

Preferably, the general structural formula of the hypocrellin derivative in formula (I) further comprises an enol tautomer represented by formula (I'), and the general structural formula of the hypocrellin derivative in formula (II) further comprises an enol tautomer represented by formula (II'):

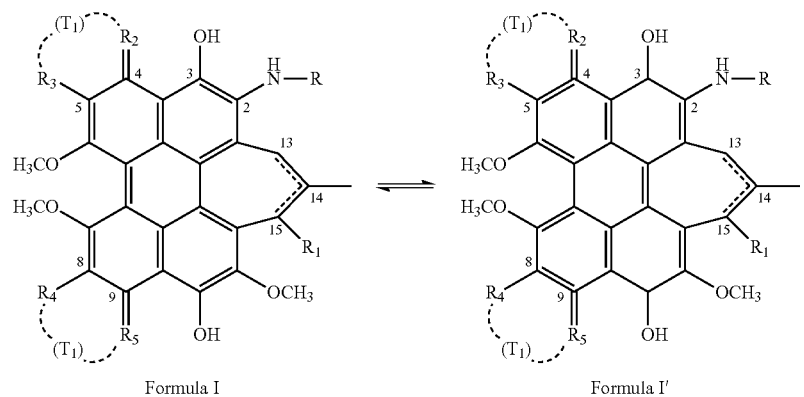

Formula I        Formula I'

-continued

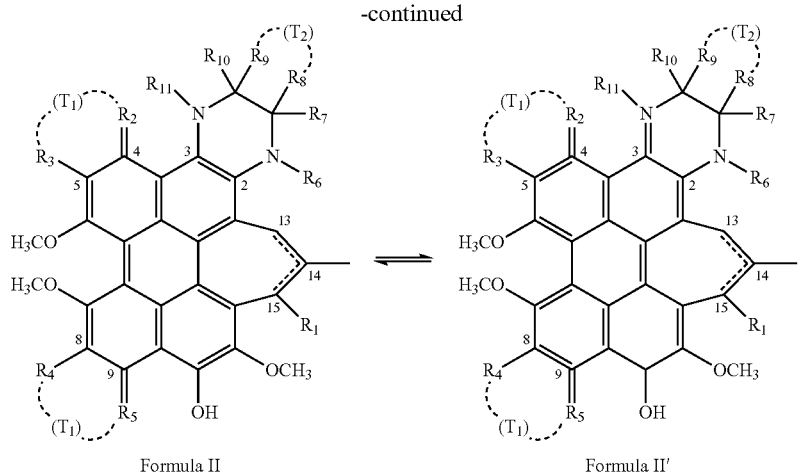

Formula II  Formula II′

To achieve the second object, the invention adopts the following technical solution:

A method for preparing the amphiphilic hypocrellin derivative in formula (IV) or (V) comprises the following steps:

dissolving hypocrellin and a corresponding substituted amino derivative in an organic solvent, keeping the resulting solution in dark under the protection of an inert gas, and obtaining the amphiphilic hypocrellin derivative by separation and purification.

The hypocrellin includes hypocrellin B (HB) and deacetylated hypocrellin (HC); the substituent of the substituted amino derivative is represented by general structural formula (III); the molar ratio of the hypocrellin to the substituted amino derivative is 1:5-1:50, and may specifically be 1:5, 1:10, 1:15, 1:20, 1:30, 1:40 or 1:50; the reaction temperature is 20-100° C.; and the reaction lasts for 6-18 h. The organic solvent is acetonitrile, tetrahydrofuran, pyridine, N,N-dimethyl formamide, methanol or ethanol; the reaction needs to be carried out in dark under the protection of an inert gas, such as argon or nitrogen.

Preferably, the organic solvent is one of acetonitrile, tetrahydrofuran and pyridine; the molar ratio of the hypocrellin to the substituted amino derivative is 1:20; the reaction temperature is 60° C.; and the reaction lasts for 8 h. Preferably, the separation and purification process includes: obtaining a residue by removing the organic solvent used in the reaction, dissolving the residue in dichloromethane, successively washing the residue with diluted aqueous hydrochloric acid solution and water, obtaining a crude product by drying and filtering the organic layer and removing the solvent, and obtaining a hypocrellin derivative containing a long chain quaternary ammonium salt by silica gel chromatography of the crude product.

Preferably, the developer used in silica gel chromatography is a mixed liquor containing acetone, ethyl acetate, ethanol and diethylamine, where the volume ratio of acetone to ethyl acetate to ethanol and to diethylamine in the mixed liquor is 20:1:1:1-20:1:3:1. Preferably, the separation and purification process includes: obtaining a blue black solid residue by removing the organic solvent used in the reaction, dissolving the residue in dichloromethane, washing the residue with equivalent volume of diluted aqueous hydrochloric acid solution (5%) thrice and with water once, and then obtaining a crude product by drying and filtering the organic layer with anhydrous magnesium sulfate and removing the solvent. The obtained crude product is further separated by silica gel chromatography with a developer of acetone:ethylacetate:ethanol:diethylamine preferably at a volume ratio of 20:1:1:1 to obtain a blue black solid amino-substituted hypocrellin derivative with a yield of 5-20%.

A method for preparing the polysubstituted near infrared hypocrellin derivative in formula (VI) or (VII) comprises the following steps:

mixing hypocrellin B or deacetylated hypocrellin and a corresponding substituted thioethylamine derivative at a molar ratio of 1:50-1:500 in a mixed solvent of an organic solvent and water, illuminating the resulting solution with light at a wavelength>450 nm at room temperature at pH>9 for 10-40 min, and obtaining a 4,5-substituted, 8,9-substituted or 4,5,8,9-substituted hypocrellin derivative by separation and purification of the product; and mixing the hypocrellin derivative and a corresponding substituted amino derivative at a molar ratio of 1:5-50 in an organic solvent, keeping the resulting solution in dark at a reaction temperature of 20-150° C. under the protection of an inert gas for 4-20 h, and obtaining the corresponding polysubstituted hypocrellin derivative in formula (VI) or formula (VII) by separation and purification of the product.

Preferably, the organic solvent is one or more of a raw material substituted amino derivative, dimethyl sulfoxide, N,N-dimethyl formamide, acetone, acetonitrile, tetrahydrofuran, pyridine, methanol and ethanol.

To achieve the third object, the invention adopts the following technical solution:

an application of the monosubstituted or polysubstituted amphiphilic hypocrellin derivative as a photosensitizer drug in PDT.

FIG. 1 is a general structural formula of a monosubstituted or polysubstituted amphiphilic hypocrellin according to the invention. FIG. 2-FIG. 6 are synthesis methods of the hypocrellin derivatives according to the invention. The amphiphilic hypocrellin derivatives synthesized according to the invention include lipophilic, hydrophilic and amphiphilic hypocrellin derivatives. The hypocrellin derivative containing polyethylene glycol or a quaternary ammonium salt or the like according to the invention has a very wide strong absorption in the phototherapy window. Its maximum absorption wavelength is about 600-630 nm, and can at most reach 650 nm. Its maximum absorption peak (450 nm) is red shifted by more than 150 nm, compared with that of the parent hypocrellin, and its molar extinction coefficient is about 10,000-40,000 $M^{-1}$ $cm^{-1}$. It shows a very strong red absorption capacity (as shown in FIG. 7). It has good water solubility, and can be prepared into a stock solution in normal saline in a concentration range of 0.1 uM-1 mM. Its ability to produce reactive oxygen is shown in FIG. 8: the experiments respectively using singlet state oxygen and superoxide radical scavenger show that such amphiphilic hypocrellin derivatives can efficiently produce photosensitively active species, mainly including singlet state oxygen (FIG. 8*a*), as well as a small amount of superoxide radical (FIG. 8*b*). The results of the confocal fluorescence imaging experiment as shown in FIG. 9 show that a small molecule phototherapy drug HB-1 has good biocompatibility, can enter the lysosomes of Hela cells, and can produce very good red fluorescence imaging in cells. The HB-1 and the Hela cells are incubated together. As shown in FIG. 10*a*, the cytotoxicity (dark toxicity) experiment shows that a PEG-containing hypocrellin derivative HB-1 synthesized in Example 3 has low cytotoxicity, and is similar to the HB and the commercial photosensitive drug haematoporphyrin HpD. After the Hela cells are incubated with the photosensitizer HB-1 at a concentration of 10 uM for half an hour, significant death of the Hela cells are not seen, showing that such photosensitizers basically have no cytotoxicity. The cell phototoxicity experiment as shown in FIG. 10*b* shows that the HB-1 shows very strong lethality against Hela cells exposed to red light, and can kill more than 90% Hela cells in a concentration range of 160 nM, while the hypocrellin B or the commercial photosensitizer hematoporphyrin derivatives can kill only about 20% Hela cells under identical conditions, indicating that such amphiphilic hypocrellin derivatives have significantly better photodynamic effects than the hypocrellin B (HB) and the commercial photosensitizer hematoporphyrin HpD. Similar results are also concluded in the dark cytotoxicity and phototoxicity experiments of a PEG-containing hypocrellin derivative HB-2 synthesized in Example 3, as shown in FIG. 11. In addition, FIG. 12 shows the phototoxic effect of killing tumor cells by an aminopropanol-modified deacetylated hypocrellin HC-3 or HC-4 synthesized in Example 4. FIG. 13 shows the phototoxic effect of killing tumor cells by deacetylated hypocrellin HC-87 or HC-88 modified with a long chain quaternary ammonium salt synthesized in Example 46. FIG. 14 shows the phototoxic effect of killing tumor cells by a piperazinohypocrellin B (HB-98) synthesized in Example 52. All of the results of the above phototoxicity experiments show that such amphiphilic hypocrellin derivatives have significantly better photodynamic effects than the hypocrellin B (HB) and the commercial photosensitizer haematoporphyrin HpD.

The polysubstituted near infrared hypocrellin derivative according to the invention has very wide strong absorption in the phototherapy window (600-900 nm). Its maximum absorption wavelength is red shifted to more than 700 nm, and can extend to 900 nm. Its molar extinction coefficient is about 10,000-40,000 $M^{-1}$ $cm^{-1}$. It shows a very strong near infrared red absorption capacity, and its synthesis method is shown in FIG. 6. The experiments respectively using singlet state oxygen and superoxide radical scavenger show that such polysubstituted near infrared hypocrellin derivatives can efficiently produce photosensitively active species, mainly including singlet state oxygen, as well as a small amount of superoxide radical (as shown in FIG. 15 and FIG. 17). As shown in FIG. 16*a*, the cytotoxicity (dark toxicity) experiment shows that a hypocrellin derivative I-1 synthesized in Example 67 has low cytotoxicity, and is similar to the hypocrellin B (HB) and the commercial photosensitive drug dihydroporphin Ce6. After Hela cells are incubated with the photosensitizer I-1 at a concentration of 10 uM for half an hour, significant death of the Hela cells are not seen, showing that such photosensitizers basically have no cytotoxicity. The cell phototoxicity experiment as shown in FIG. 16*b* shows that the I-1 shows very strong lethality against Hela cells exposed to 671 near infrared, and can kill more than 90% Hela cells in a concentration range of 200 nM, while the commercial photosensitizer dihydroporphin Ce6 can kill only about 30% Hela cells under identical conditions. By comparison with the dark cytotoxicity and phototoxicity experiments of a hypocrellin derivative II-2 synthesized in Example 86, as shown in FIG. 18, it is worth pointing out that an 808 nm near infrared laser is used, indicating that such compounds can be used in PDT for penetrating deeper tumor tissues.

Compared with the parent hypocrellin B, the amphiphilic hypocrellin derivatives according to the invention have greatly enhanced water solubility by introducing PEG, a quaternary ammonium salt or the like, and have good amphiphilicity, as well as very good biocompatibility in cells or tissues, by changing the aliphatic chain length to adjust oil-water ratio. These compounds exist in the form of PEG or a quaternary ammonium salt, are not susceptible to pH, and can be used in complex organisms. Such a hypocrellin with a normal salt like a quaternary ammonium salt can effectively bind to negatively charged species in an organism, especially has very good affinity to tumor cells. The effect of phototherapy is changed by adjusting the distance between the quaternary ammonium salt and the parent hypocrellin. The hydrophilicity and hydrophobicity of photosensitive drug molecules produced using PEG can be regulated at will by changing the number of PEG structure units, in order to meet the needs of different clinical drugs. Furthermore, the PEG structure is non-toxic, is also a drug component approved by FDA, and has very good biocompatibility. Therefore, such amphiphilic hypocrellin derivatives can be directly dissolved in normal saline to make pharmaceutical preparations and improve the medicinal effect; are made from natural products and will not produce toxic or side effects, thereby laying the foundation for the development of hypocrellin drugs for treating cancers and hypocrellin drugs against cancer viruses.

Hypocrellin is modified with a PEG group or a long chain quaternary ammonium salt or the like, and its molecular hydrophilicity and hydrophobicity are adjusted, so that such derivatives have different amphilicities, and their biocompatibility with cells or tissues is improved. Such compounds have the maximum absorption wavelength of 600-735 nm, molar extinction coefficients of 10,000-40,000 $M^{-1}$ $cm^{-1}$, and very strong light absorption capacity in the phototherapy window. Researches have shown that such derivatives can efficiently produce singlet state oxygen and other reactive oxygen species under photosensitive conditions, have very good photodynamic effects, and can be used as phototherapy drugs for treating tumors, various microangiopathies and other diseases.

In the prior art, neither preparation nor extraction of a PEG-modified hypocrellin derivative is researched. No researches are found to be related to such compounds that can satisfy not only light absorption conditions, but also optimized amphiphilicity, i.e., meeting the concentration requirements for intravenous injection to ensure a high cellular uptake rate.

Moreover, it should be noted that the hypocrellin derivatives to be protected in the patent each contain two enol tautomers (e.g., formulas 1 and 1', formulas 2 and formula 2'), the chemical structures of which fall, of course, within the scope of protection. Moreover, unless otherwise indicated, any range disclosed in the invention includes any subrange consisting of end values and any value between the end values, and end values or any value between the end values.

The invention has the following beneficial effects:

1) in the invention, the raw materials of hypocrellin are extracted from natural products, are readily available, are cheap, and facilitate mass production; the product has low toxic and side effects, and is easily metabolizeable; and the synthesis and separation methods are simple without expensive reaction materials and complex separation approaches.

2) The obtained hypocrellin derivative substituted by a group containing PEG, a quaternary ammonium salt or the like has an obvious red shift in its absorption spectrum and a significantly enhanced molar extinction coefficient, compared with the parent hypocrellin, can efficiently produce reactive oxygen (mainly including singlet state oxygen, supplemented by superoxide radical and other reactive oxygen species) under photosensitive conditions; has different amphiphilicities and increased biocompatibility with cells or tissues by regulating its hydrophilicity and hydrophobicity via introducing a structure, such as PEG, a quaternary ammonium salt or the like, into the parent hypocrellin; can meet the requirements of different clinical drugs, and solves the requirements of different drug delivery methods for different drug hydrophilicity and lipophilicity.

3) The polysubstituted near infrared hypocrellin derivative prepared in the invention has an obvious red shift of its absorption spectrum to more than 700 nm and a high molar extinction coefficient, compared with the parent hypocrellin.

4) Compared with the first generation porphyrin photosensitizer and the second generation phthalocyanine photosensitizer in clinical use, the amphiphilic hypocrellin derivative according to the invention has significantly improved absorption wavelength and light absorption capacity. What is important is that the product can be easily separated and purified with a specific structure, and overcomes the defects of porphyrin and phthalocyanine photosensitizers, such as difficult separation, complex composition and difficult structural determination. What is more important is that under identical conditions, the amphiphilic hypocrellin derivative photosensitizer according to the invention has higher ability to photodynamically inactivate tumor cells than the first and second generation commercial photosensitizers.

BRIEF DESCRIPTION OF THE DRAWINGS

The embodiments of the invention are further illustrated in detail below in conjunction with the accompanying drawings.

DETAILED DESCRIPTION

Figure 1:
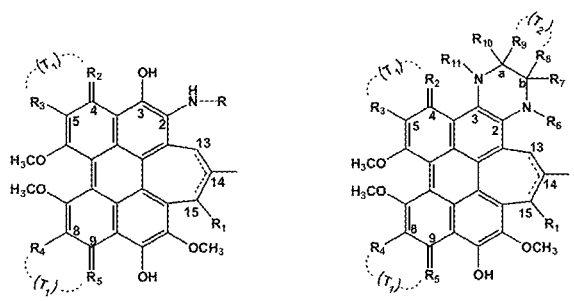
FIG. 1 shows a general structural formula of a monosubstituted or polysubstituted amphiphilic hypocrellin derivative according to the invention.

In order to illustrate the invention more clearly, the invention is further described below in conjunction with the preferred embodiments and the accompanying drawings, wherein like reference symbols represent like parts. As will be appreciated by those skilled in the art, the following specific description is descriptive rather than restrictive, and should not be used to limit the scope of protection of the invention.

Example 1

Extraction of hypocrellin A (HA): 100 g of hypocrellin was pulverized by a pulverizer, and continuously extracted with 1,000 ml of acetone as a solvent in a Soxhlet extractor for one day until nearly colorless. The extract was filtered to remove a small amount of infiltrated solid insoluble substances, spin-dried to remove acetone, dissolved in 500 ml of dichloromethane, and washed four times and each with 400 mL of distilled water. The organic layer was separated and spin-dried, the solid residue was washed five times and each with 100 mL of petroleum ether, naturally air-dried, and then recrystallized with chloroform-petroleum ether twice. The resulting crystal was the target product HA with a purity of more than 98%. Highly purified HA can be obtained by further purification using thin layer silica gel chromatography with petroleum ether:ethyl acetate:anhydrous ethanol (30:10:1) as a developer.

Preparation of hypocrellin B (HB): the HB was prepared by dehydrating the HA using a method, which is an appropriate improvement of a method in a reference book *Organic Chemistry* (pp. 252-254, Vol. 9, 1989, Zhao Kaihong). The specific method is as follows: 1 g of the HA was dissolved in 1000 mL of 1.5% aqueous solution of KOH, stirred in dark for 24 h, and neutralized with slightly excessive diluted hydrochloric acid. A product was extracted with chloroform, and purified by separation to obtain 0.98 g of the HB with a yield of 98%.

Preparation of deacetylated hypocrellin (HC): 200 mg of the HB was dissolved in 100 mL of 1.5% aqueous solution of KOH, refluxed in dark for 8 h, cooled, and then neutralized with slightly excessive diluted hydrochloric acid. A product was extracted with dichloromethane, and purified by separation to obtain 110 mg of the deacetylated hypocrellin (HC) with a yield of 56%. $^1$H NMR (CDCl$_3$, δ, ppm): 16.0 (s, —OH, 1H), 15.9 (s, —OH, 1H), 6.62 (d, 1H), 6.35 (s, 2H), 4.14, 4.12 (s, —OCH$_3$, 6H), 4.02 (s, —OCH$_3$, 3H), 3.1 (d, 2H), 2.25 (s, —OCH$_3$, 3H).

Example 2

The derivatives containing a long chain quaternary ammonium salt according to the invention were prepared using the following general methods, which are described by taking H$_2$NCH$_2$CH$_2$—N$^+$(CH$_3$)$_2$(C$_{10}$H$_{21}$) as an example.

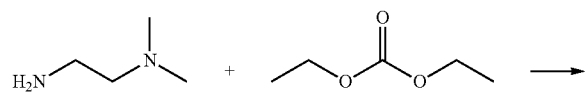

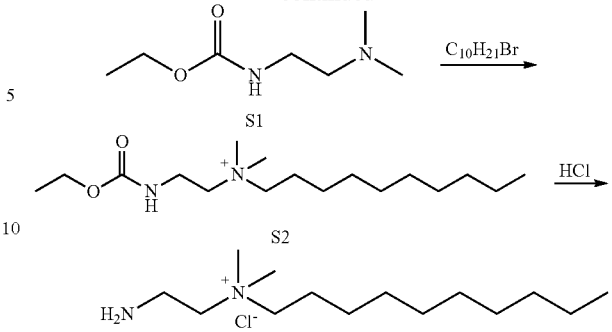

Preparation of an intermediate S1: N,N-dimethyl ethyldiamine (4.4 g, 0.05 mol) and diethyl carbonate (7.10 g, 0.06 mol) were mixed in a 100 ml round-bottomed flask, kept at 70° C. for 48 h, and then distilled under reduced pressure to obtain 7.20 g of a pale yellow liquid with a yield of 89%. $^1$H NMR (CDCl$_3$, δ, ppm): 5.45 (s, —NH—, 1H), 4.10 (d, J=6.5 Hz, —CH$_2$O, 2H), 3.24 (s, —NH—CH$_2$—, 2H), 2.39 (m, —CH$_2$N, 2H), 2.22 (d, J=1.5 Hz, CH$_3$NCH$_3$, 6H), 1.23 (t, J=6.5 Hz, —CH$_2$CH$_3$, 3H).

Preparation of an intermediate S2: the intermediate S1 reacted with 1-bromodecane (15.25 g, 0.05 mol) at 100° C. for 48 h for 72 h. The crude product was recrystallized with acetone-diethyl ether (1:1) to obtain a total of 15.83 g of a white crystal 2 with a yield of about 68%. $^1$H NMR (CDCl$_3$, δ, ppm): 6.73 (s, CONH—, 1H), 4.10 (q, J=7.1 Hz, —CH$_2$O—, 2H), 3.77 (s, —CH$_2$N$^+$, 4H), 3.53 (s, CH$_3$N$^+$, 6H), 3.39 (s, —NHCH$_2$—, 2H), 1.78-1.67 (m, —N$^+$CH$_2$CH$_2$—, 2H), 1.31-1.20 (m, —CH$_2$—, 29H), 0.88 (t, J=6.8 Hz, —CH$_3$, 3H). MS(ESI+): C$_{23}$H$_{50}$N$_2$O$_2$$^+$ (M+H$^+$), 385.3788.

Preparation of a long chain quaternary ammonium salt derivative S3: 50 mL of 48% hydrobromic acid and 50 mL of distilled water were added to the intermediate S2 (10.60 g, 0.02 mol), and refluxed while heating for 72 h. Hydrobromic acid was removed by rotary evaporation, and the solid residue was recrystallized with ethanol:diethyl ether (1:1) to obtain 13.62 g of a white flocculent crystal with a yield of 69%. $^1$H NMR (D$_2$O, δ, ppm): 5.34 (s, NH$_2$, 2H), 3.65 (m, NH$_2$CH$_2$CH$_2$—, 2H), 3.48 (m, —N$^+$CH$_2$CH$_2$—, 2H), 3.38 (m, NH$_2$CH$_2$—, 2H), 3.12 (s, N$^+$—CH$_3$, 6H), 1.78 (m, —N$^+$CH$_2$CH$_2$—, 2H), 1.37-0.99 (m, —CH$_2$—, 26H), 0.76 (t, J=6.5 Hz, —CH$_3$, 3H). MS (ESI+): C$_{20}$H$_{46}$N$_2$$^+$ (M+H$^+$), 313.3590.

Example 3

Figure 2:
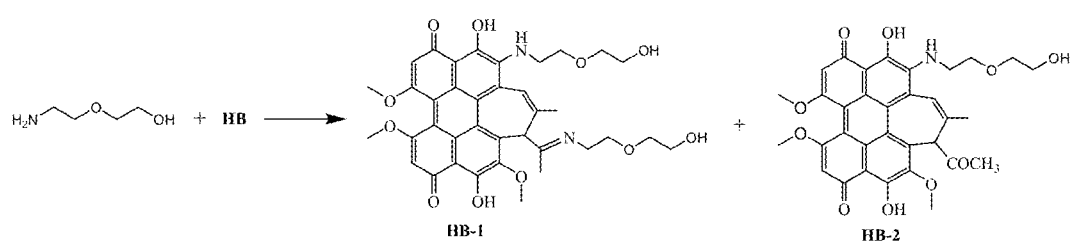
FIG. 2 shows a synthesis reaction route map of PEG-containing hypocrellin B derivatives HB-1 and HB-2 according to Example 3 of the invention.

Preparation of an aminoethyl glycol-modified hypocrellin derivative (R=—CH$_2$CH$_2$OCH$_2$CH$_2$OH): the synthesis route as shown in FIG. 2: Hypocrellin B (HB) (100 mg, 0.18 mmol) and aminoethyl glycol (0.40 g, 4 mmol) were dissolved in 20 mL of anhydrous acetonitrile, fully mixed, heated to 50° C. under nitrogen protection, and stirred in dark for 10 h. On completion of the reaction, the solvent was removed by rotary evaporation. A blue black solid residue was dissolved in 200 mL of dichloromethane, and successively washed with 100 mL of diluted aqueous hydrochloric acid solution once and with distilled water twice. The organic layer was dried with anhydrous magnesium sulfate, and filtered, and then the organic phase was spin-dried to obtain a crude product. The resulting crude product was further separated by silica gel chromatography with acetone:

ethyl acetate (volume ratio: 1:1) as a developer to respectively obtain two blue black solid products with Rf values respectively being 0.80 and 0.24, where the product with the Rf being 0.24 was identified to be a 2,17-substituted product, and was labeled as HB-1 with a yield of 12.2%; and the component with the Rf being 0.80 was further separated with acetone:petroleum ether (volume ratio: 1:1) using chromatography to obtain a product with the Rf value being 0.85 (detected as a 2-amino-substituted product, labeled as HB-2) with a yield of 6.5%.

Characterization data of 2,17-amino-substituted product HB-1 are as follows: $^1$HNMR (CDCl$_3$, δ, ppm): 17.16 (s, ArOH, 1H), 12.96 (s, ArOH, 1H), 6.98 (s, ArH, 1H), 6.55 (s, ArH, 1H), 6.34 (s, ArNH, 1H), 5.35 (s, ArNH, 1H), 5.22 (s, OH, 1H), 5.01 (s, OH, 1H), 4.18 (s, OCH$_3$, 3H), 4.06 (s, OCH$_3$, 3H), 4.04 (s, OCH$_3$, 3H), 3.91-3.61 (m, NHCH$_2$CH$_2$O, 12H), 3.56 (d, CH, 1H), 3.25 (d, CH, 1H), 2.27 (s, COCH$_3$, 3H), 2.19 (m, CH$_2$O, 2H), 2.02 (m, CH$_2$O, 2H), 1.57 (s, CH$_3$, 3H), 1.41-1.02 (m, CH$_2$—, 19H), 0.78 (t, CH$_3$, 3H). MS (ESI): C$_{37}$H$_{40}$N$_2$O$_{11}$ (M+H$^+$), 689.0. Maximum UV absorption wavelength: 468 nm, 630 nm.

Characterization data of 2-amino-substituted product HB-2 are as follows: $^1$HNMR (CDCl$_3$, δ, ppm): 16.76 (s, ArOH, 1H), 16.51 (s, ArOH, 1H), 6.50 (s, ArH, 1H), 6.47 (s, ArH, 1H), 6.40 (s, ArH, 1H), 5.80 (s, CH$_2$, 1H), 5.23 (s, CH$_2$, 1H), 4.18 (s, OCH$_3$, 3H), 4.08 (s, OCH$_3$, 3H), 4.02 (s, OCH$_3$, 3H), 3.83-3.76 (m, NHCH$_2$CH$_2$, 4H), 3.67-3.62 (m, OCH$_2$CH$_2$, 4H), 2.78 (s, OH, 1H), 2.27 (s, COCH$_3$, 3H), 1.61 (s, CH$_3$, 3H). MS (ESI): C$_{33}$H$_{31}$NO$_{10}$, 624.1 (M+Na$^+$), 600.5 (M−H). Maximum UV absorption wavelength: 464 nm, 625 nm.

The amino-substituted products HB-1 and HB-2 have the structural formulas as shown in the figure:

Deacetylated hypocrellin HC (100 mg, 0.20 mmol) and aminoethyl glycol (0.30 g, 4 mmol) were dissolved in 20 mL of anhydrous tetrahydrofuran, fully mixed, heated to 60° C. under nitrogen protection, and stirred in dark for 12 h. On completion of the reaction, the solvent was removed by rotary evaporation. A blue black solid residue was dissolved in 200 mL of dichloromethane, and successively washed with 100 mL of diluted aqueous hydrochloric acid solution once and with distilled water twice. The organic layer was dried with anhydrous magnesium sulfate, and filtered, and then the organic phase was spin-dried to obtain a crude product. The resulting crude product was further separated by silica gel chromatography with acetone:ethyl acetate (volume ratio: 1:1) as a developer to obtain a blue black solid product with a yield of 15.2% with Rf value of 0.45. MS (ESI+): 530.6. The amino-substituted product HC-3 (double bond located at C$_{13}$=C$_{14}$) or HC-4 (double bond located at C$_{14}$=C$_{15}$) has the structural formula as shown in the figure:

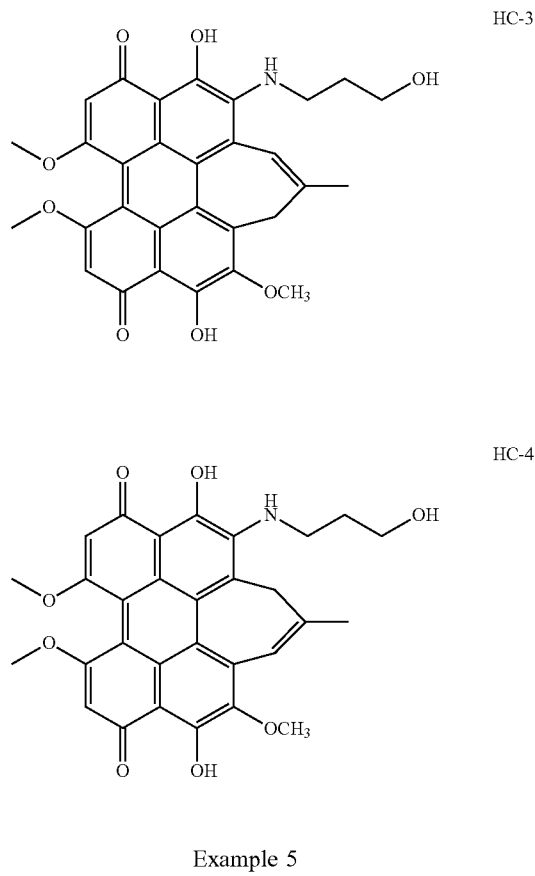

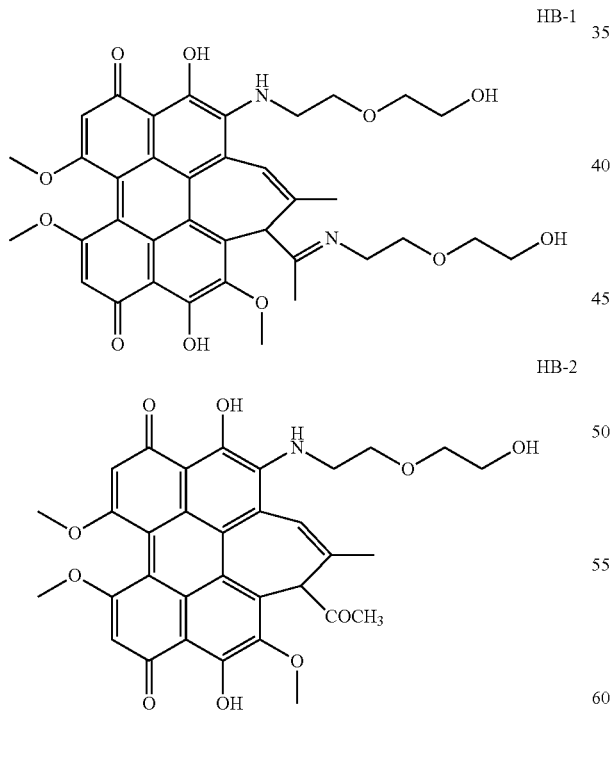

Example 4

Figure 3:
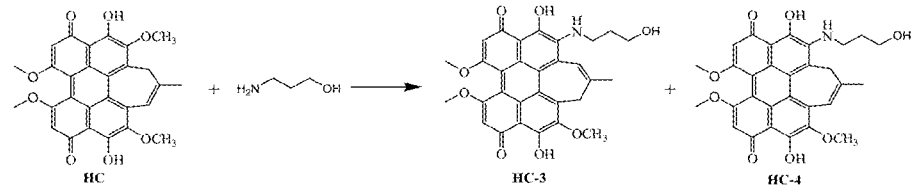
FIG. 3 shows a synthesis reaction route map of deacetylated hypocrellin HC and aminopropanol according to Example 4 of the invention.

Preparation of a 3-aminopropanol-modified deacetylated hypocrellin derivative (R=—CH$_2$CH$_2$CH$_2$OH): the synthesis route as shown in FIG. 3:

Example 5

Preparation of an aminoethyl triglycol-modified hypocrellin B derivative (R=—(CH$_2$CH$_2$—(OCH$_2$CH$_2$)$_2$—OH): the synthesis method similar to the preparation of an aminoethyl glycol-modified hypocrellin B derivative in Example 3. 2,17-amino-substituted product HB-5: yield: 8.4%, Rf: 0.24, MS (ESI+) 777.5, maximum UV absorption wavelength: 468 nm, 632 nm. 2-amino-substituted product HB-6: yield: 5.8%, Rf: 0.55, MS (ESI+) 646.6, maximum UV absorption wavelength: 462 nm, 625 nm. The amino-substituted products HB-5 and HB-6 have the structural formulas as shown in the figure:

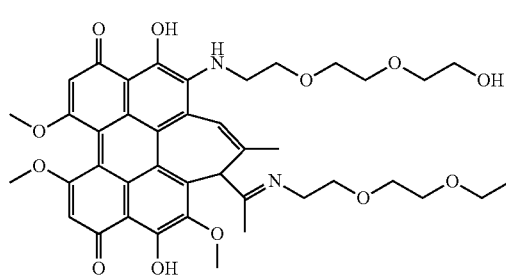

HB-5

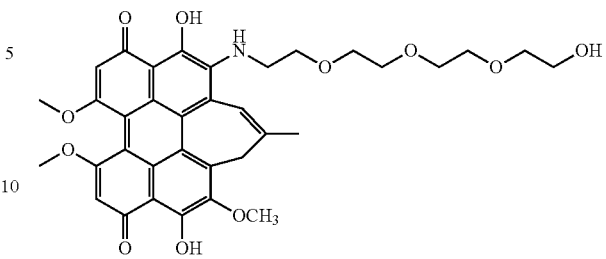

HC-7

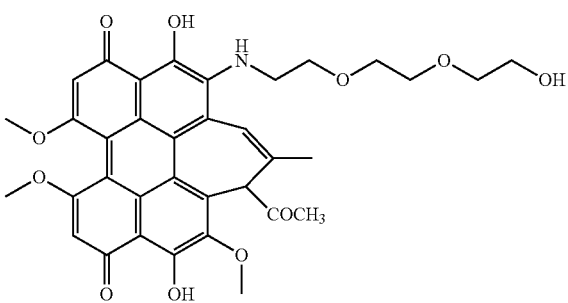

HB-6

HC-8

Example 6

Preparation of an aminoethyl tetraglycol-modified deacetylated hypocrellin derivative (R=—(CH$_2$CH$_2$—(OCH$_2$CH$_2$)$_3$—OH): the synthesis method similar to the preparation of a 3-aminopropanol-modified deacetylated hypocrellin derivative in Example 4. The resulting product: yield: 10.5%, Rf: 0.25. Characterization data as follows: MS (ESI+): 648.5; Maximum UV absorption wavelength: 468 nm, 632 nm. The amino-substituted product HC-7 (double bond located at C$_{13}$═C$_{14}$) or HC-8 (double bond located at C$_{14}$═C$_{15}$) has the structural formula as shown in the figure:

Example 7

Preparation of an aminoethyl pentaglycol-modified hypocrellin B derivative (R=—(CH$_2$CH$_2$—(OCH$_2$CH$_2$)$_4$—OH): the synthesis method similar to the preparation of an aminoethyl glycol-modified hypocrellin B derivative in Example 3. 2,17-amino-substituted product HB-9: yield: 12.4%, Rf: 0.30, MS (ESI+) 953.0, maximum UV absorption wavelength: 475 nm, 640 nm. 2-amino-substituted product HB-10: yield: 6.4%, Rf: 0.65, MS (ESI+) 734.3, maximum UV absorption wavelength: 470 nm, 630 nm. The amino-substituted products HB-9 and HB-10 have the structural formulas as shown in the figure:

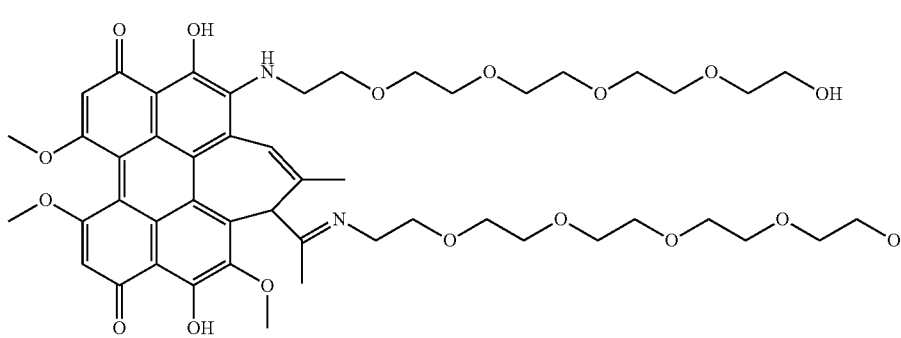

HB-9

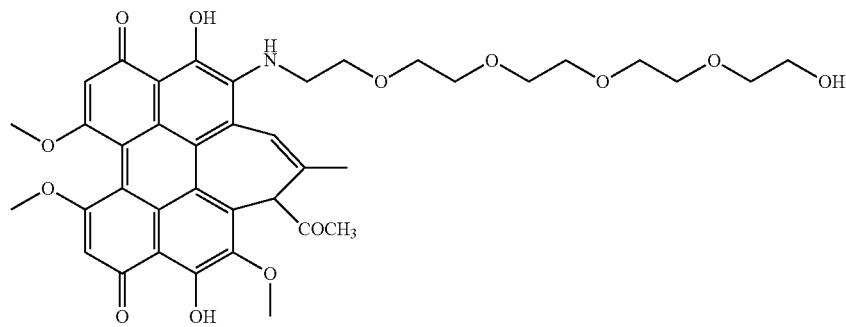

Example 8

Preparation of an aminoethyl polyglycol-modified deacetylated hypocrellin B derivative (R=—(CH$_2$CH$_2$—(OCH$_2$CH$_2$)$_n$—OH): the synthesis method similar to the preparation of a 3-aminopropanol-modified deacetylated hypocrellin derivative in Example 4. The resulting product: yield: 17.5%, Rf: 0.25; characterization data as follows: MS (ESI+): 560.0. Maximum UV absorption wavelength: 480 nm, 635 nm. The amino-substituted product HC-11 (double bond located at C$_{13}$=C$_{14}$) or HC-12 (double bond located at C$_{14}$=C$_{15}$) has the structural formula as shown in the figure:

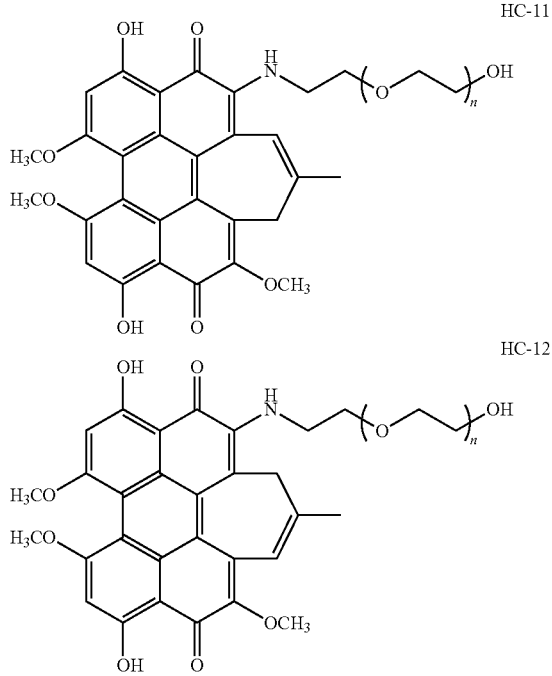

Example 9

Preparation of a 3-aminopropyl glycol-modified hypocrellin B derivative (R=—(CH$_2$)$_3$—OCH$_2$CH$_2$OH): the synthesis method similar to the preparation of an aminoethyl glycol-modified hypocrellin B derivative in Example 3. 2,17-amino-substituted product HB-13: yield: 6.5%, Rf: 0.16, MS (ESI+) 717.2, maximum UV absorption wavelength: 476 nm, 632 nm. 2-amino-substituted product HB-14: yield: 5.4%, Rf: 0.50, MS (ESI+) 615.6, maximum UV absorption wavelength: 463 nm, 624 nm. The amino-substituted products HB-13 and HB-14 have the structural formulas as shown in the figure:

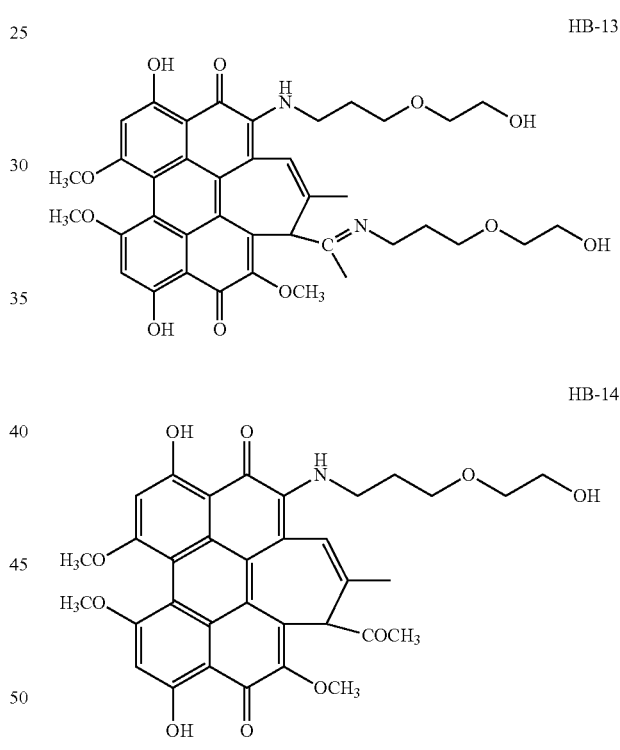

Example 10

Preparation of an ethylene glycol aminoacetate-modified deacetylated hypocrellin B derivative (R=—CH$_2$ COOCH$_2$ CH$_2$OH): the synthesis method similar to the preparation of a 3-aminopropanol-modified deacetylated hypocrellin derivative in Example 4. The resulting product: yield: 18.5%; Rf: 0.18; MS (ESI+) 574.5; maximum UV absorption wavelength: 474 nm, 638 nm. The amino-substituted product HC-15 (double bond located at C$_{13}$=C$_{14}$) or HC-16 (double bond located at C$_{14}$=C$_{15}$) has the structural formula as shown in the figure:

HC-15

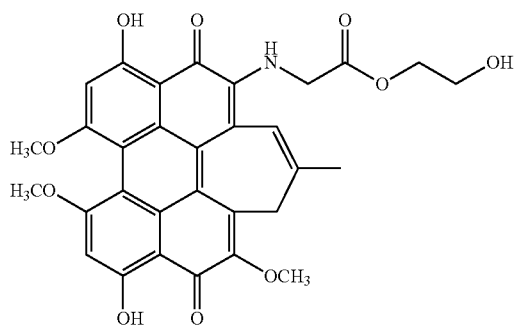

HB-18

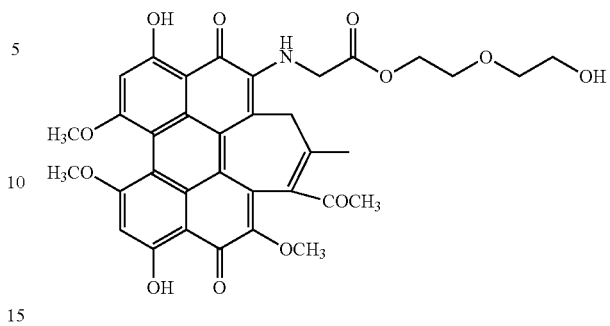

HC-16

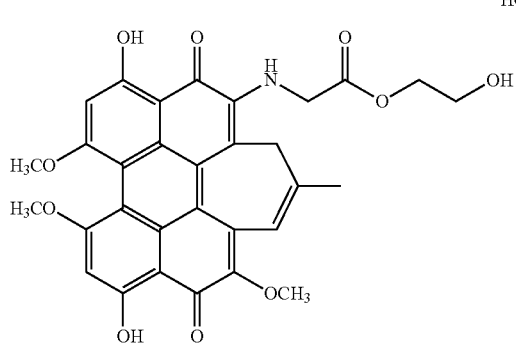

Example 12

Preparation of a triethylene glycol aminoacetate-modified deacetylated hypocrellin derivative (R=—CH$_2$CO(OCH$_2$CH$_2$)$_3$OH): the synthesis method similar to the preparation of a 3-aminopropanol-modified deacetylated hypocrellin derivative in Example 4. The resulting product: yield: 17.2%; Rf: 0.18; MS (ESI+) 662.3; maximum UV absorption wavelength: 466 nm, 640 nm. The amino-substituted product HC-19 (double bond located at C$_{13}$=C$_{14}$) or HC-20 (double bond located at C$_{14}$=C$_{15}$) has the structural formula as shown in the figure:

Example 11

Preparation of a diethylene glycol aminoacetate-modified hypocrellin B derivative (R=—CH$_2$CO(OCH$_2$CH$_2$)$_2$OH): the synthesis method similar to the preparation of an aminoethyl glycol-modified hypocrellin B derivative in Example 3. 2,17-amino-substituted product HB-17: yield: 6.2%, Rf: 0.16, MS (ESI+) 805.5, maximum UV absorption wavelength: 468 nm, 635 nm. 2-amino-substituted product HB-18: yield: 3.4%, Rf: 0.60, MS (ESI+) 659.6, maximum UV absorption wavelength: 462 nm, 624 nm. The amino-substituted products HB-17 and HB-18 have the structural formulas as shown in the figure:

HC-19

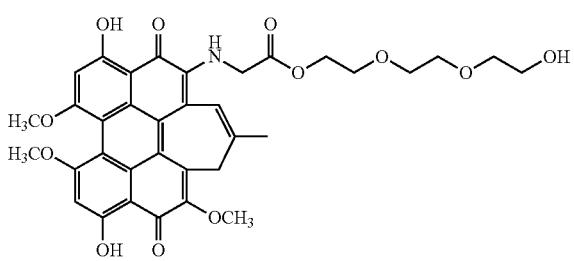

HB-17

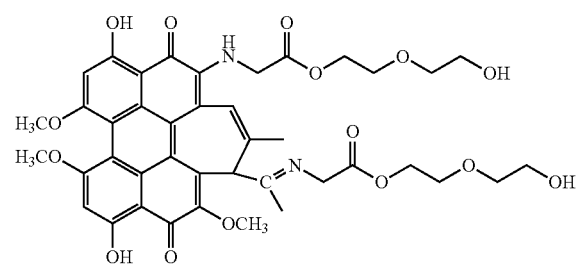

HC-20

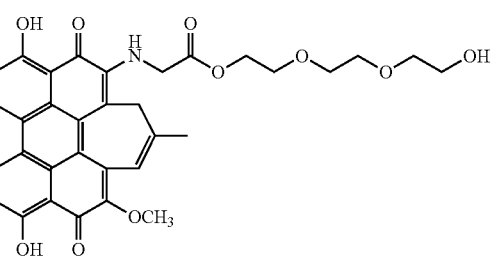

Example 13

Preparation of a polyethylene glycol aminopropionate-modified hypocrellin B derivative (R=—(CH$_2$)$_2$CO(OCH$_2$CH$_2$)$_n$OH): the synthesis method similar to the preparation of an aminoethyl glycol-modified hypocrellin B derivative in Example 3. 2,17-amino-substituted product HB-21: yield: 8.5%, Rf: 0.18, maximum UV absorption wavelength: 485 nm, 645 nm. 2-amino-substituted product HB-22: yield: 4.5%, Rf: 0.50, maximum UV absorption wavelength: 465 nm, 635 nm. The amino-substituted products HB-21 and HB-22 have the structural formulas as shown in the figure:

HB-21

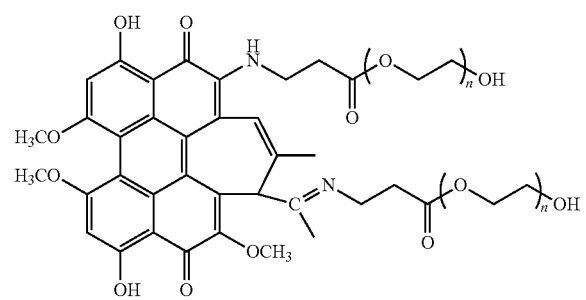

HB-22

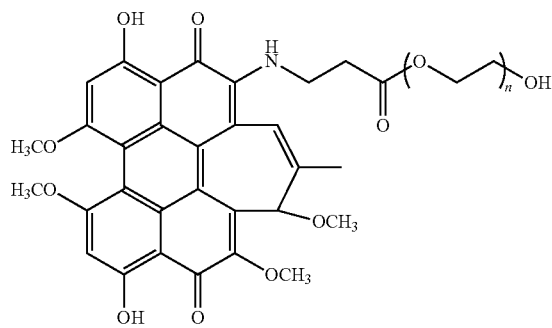

Example 14

Preparation of a triethylene glycol aminopentanoate-modified deacetylated hypocrellin derivative (R=—(CH$_2$)$_4$CO(OCH$_2$CH$_2$)$_3$$_0$H): the synthesis method similar to the preparation of a 3-aminopropanol-modified deacetylated hypocrellin derivative in Example 4. The resulting product: yield: 12.5%; Rf: 0.21; MS (ESI+) 704.5; maximum UV absorption wavelength: 455 nm, 642 nm. The amino-substituted product HC-23 (double bond located at C$_{13}$=C$_{14}$) or HC-24 (double bond located at C$_{14}$=C$_{15}$) has the structural formula as shown in the figure:

HC-23

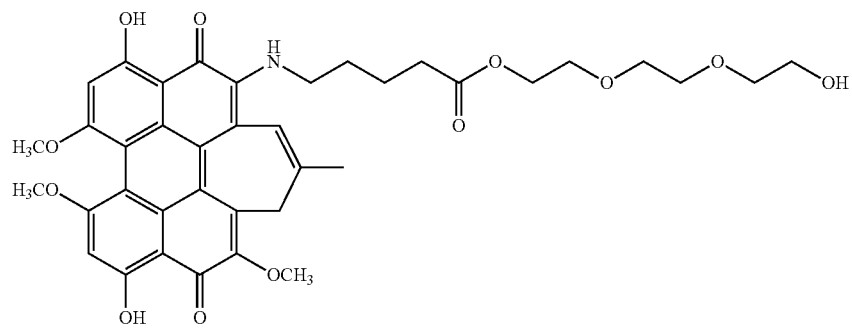

HC-24

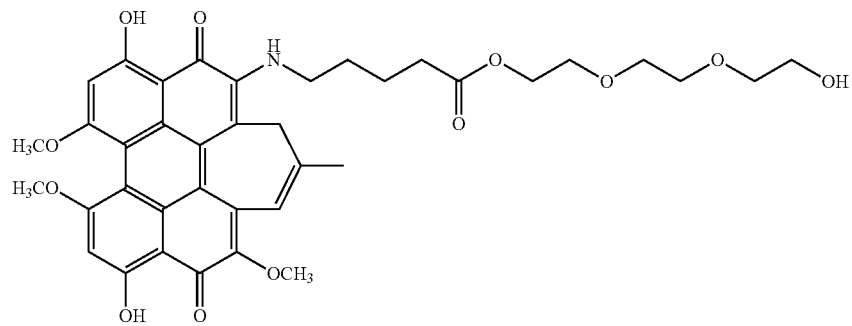

Example 15

Preparation of an ethylene glycol aminomethanesulfonate-modified hypocrellin derivative (R=—CH$_2$SO$_2$—OCH$_2$CH$_2$—OH): hypocrellin B (HB) (100 mg, 0.18 mmol) and monoethylene glycol aminomethanesulfonate (610 mg, 4 mmol) were dissolved in 20 mL of anhydrous acetonitrile, heated to 55° C. under nitrogen protection, and stirred in dark for 8 h. Then the solvent was removed by rotary evaporation. A blue black solid residue was dissolved in 200 mL of dichloromethane, and successively washed with diluted aqueous hydrochloric acid solution twice and with distilled water once. The organic layer was dried, and filtered, and then the organic phase was spin-dried to obtain a crude product. The resulting crude product was separated by thin layer silica gel chromatography with acetone:petroleum ether (volume ratio: 2:1) as a developer to obtain two blue black solid products. 2,17-amino-substituted product HB-25: yield: 9.2%, Rf: 0.18, MS (ESI+) 789.2, maximum UV absorption wavelength: 470 nm, 640 nm. 2-amino-substituted product HB-26: yield: 4.4%, Rf: 0.55, MS (ESI+) 652.6, maximum UV absorption wavelength: 465 nm, 628 nm. The amino-substituted products HB-25 and HB-26 have the structural formulas as shown in the figure:

HB-25

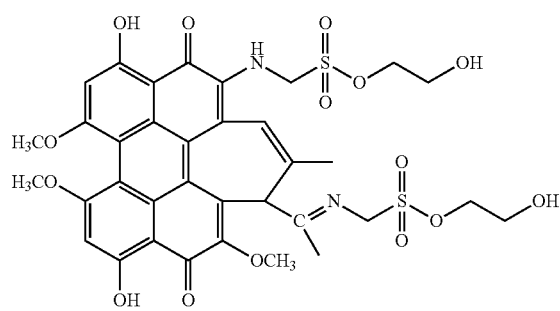

HB-26

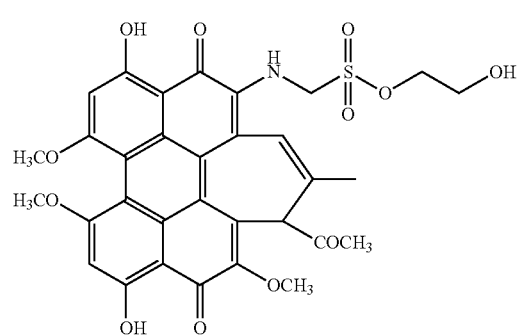

Example 16

Preparation of a diethylene glycol aminomethanesulfonate-modified deacetylated hypocrellin derivative (R=—CH$_2$SO$_2$(OCH$_2$CH$_2$)$_2$OH): the synthesis method similar to the preparation of a diethylene glycol aminomethanesulfonate-modified hypocrellin derivative in Example 15. The resulting product: yield: 16.2%; Rf: 0.16; MS (ESI+) 654.2; maximum UV absorption wavelength: 468 nm, 635 nm. The amino-substituted product HC-27 (double bond located at C$_{13}$=C$_{14}$) or HC-28 (double bond located at C$_{14}$=C$_{15}$) has the structural formula as shown in the figure:

HC-27

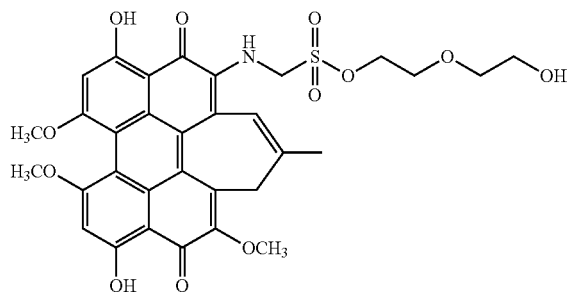

HC-28

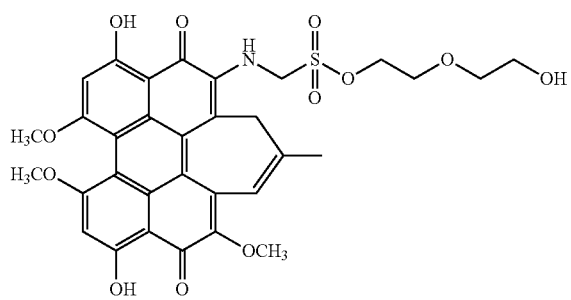

Example 17

Preparation of a tetraethylene glycol aminomethanesulfonate-modified hypocrellin derivative (R=—CH$_2$SO$_2$(OCH$_2$CH$_2$)$_4$OH): the synthesis method similar to the preparation of a diethylene glycol aminomethanesulfonate-modified hypocrellin derivative in Example 15. 2,17-amino-substituted product HB-29: yield: 8.4%, Rf: 0.16, MS (ESI+) 1053.4, maximum UV absorption wavelength: 468 nm, 648 nm. 2-amino-substituted product HB-30: yield: 5.4%, Rf: 0.62, MS (ESI+) 784.6, maximum UV absorption wavelength: 462 nm, 625 nm. The amino-substituted products HB-29 and HB-30 have the structural formulas as shown in the figure:

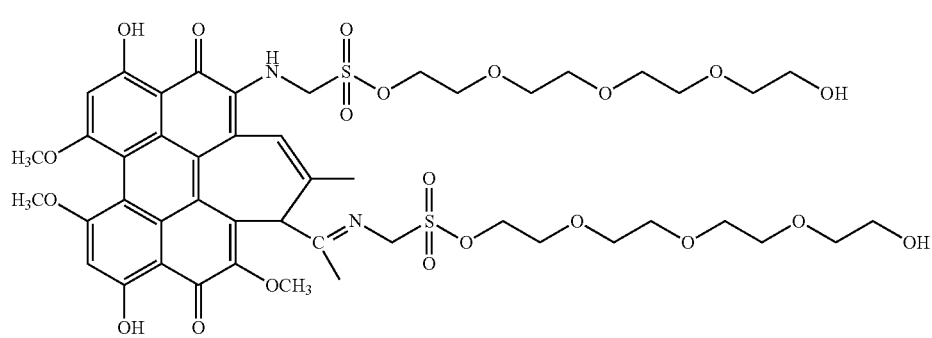

HB-29

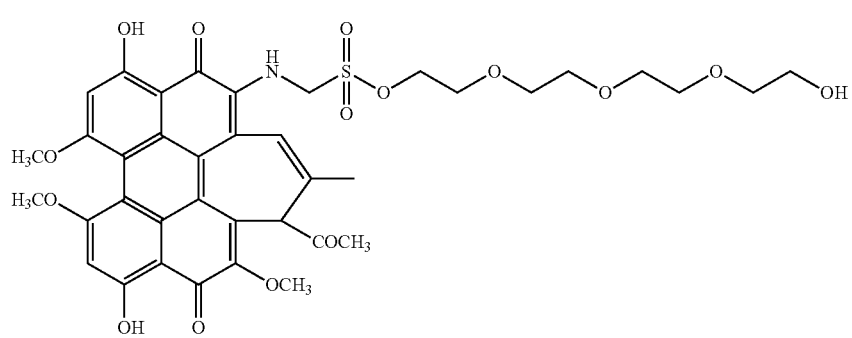

HB-30

Example 18

Preparation of a triethylene glycol aminobutanesulfonate-modified hypocrellin derivative (R=—CH$_2$CH$_2$CH$_2$CH$_2$SO$_2$(OCH$_2$CH$_2$)$_3$OH): the synthesis method similar to the preparation of a diethylene glycol aminomethanesulfonate-modified hypocrellin derivative in Example 15. The resulting product: yield: 16.5%; Rf: 0.21; MS (ESI+) 1036.5; maximum UV absorption wavelength: 455 nm, 638 nm. The amino-substituted product HC-31 (double bond located at C$_{13}$=C$_{14}$) or HC-32 (double bond located at C$_{14}$=C$_{15}$) has the structural formula as shown in the figure:

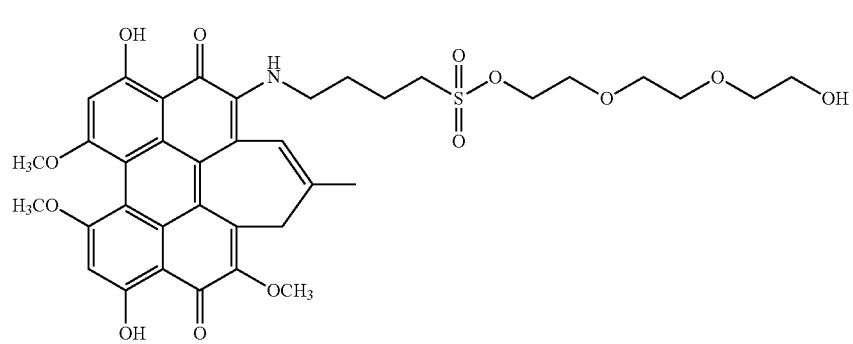

HC-31

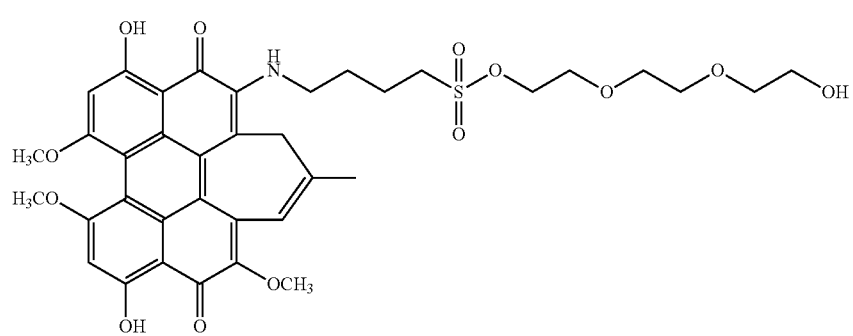

HC-32

Example 19

Preparation of an ethylenediamino-substituted triglycol-modified hypocrellin B derivative (R=—(CH$_2$CH$_2$—NHCH$_2$CH$_2$—OCH$_2$CH$_2$—OH): the synthesis method similar to the preparation of an aminoethyl glycol-modified hypocrellin B derivative in Example 3. 2,17-amino-substituted product HB-33: yield: 9.4%, Rf: 0.18, MS (ESI+) 775.5, maximum UV absorption wavelength: 469 nm, 635 nm. 2-amino-substituted product HB-34: yield: 8.8%, Rf: 0.58, MS (ESI+) 644.6, maximum UV absorption wavelength: 464 nm, 626 nm. The amino-substituted products HB-33 and HB-34 have the structural formulas as shown in the figure:

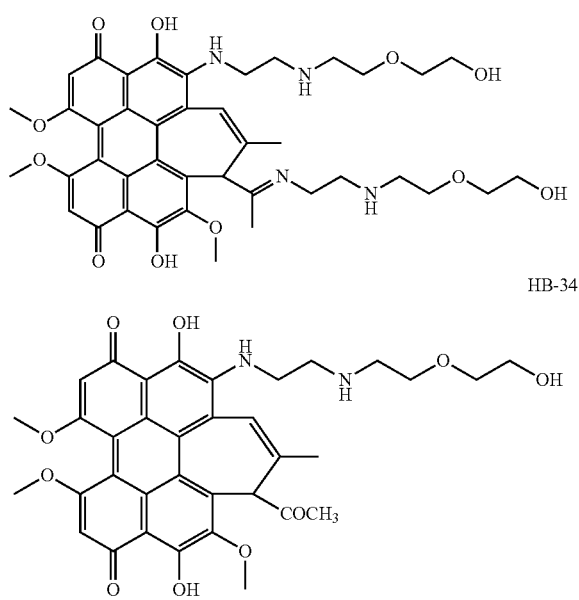

Example 20

Preparation of an ethylenediamino triglycol-modified deacetylated hypocrellin derivative (R=—(CH$_2$CH$_2$—NHCH$_2$CH$_2$—(OCH$_2$CH$_2$)$_2$—OH): the synthesis method similar to the preparation of a 3-aminopropanol-modified deacetylated hypocrellin derivative in Example 4. The resulting product: yield: 19.5%, Rf: 0.22. Characterization data as follows: MS (ESI+): 646.5; Maximum UV absorption wavelength: 468 nm, 631 nm. The amino-substituted product HC-35 (double bond located at C$_{13}$=C$_{14}$) or HC-36 (double bond located at C$_{14}$=C$_{15}$) has the structural formula as shown in the figure:

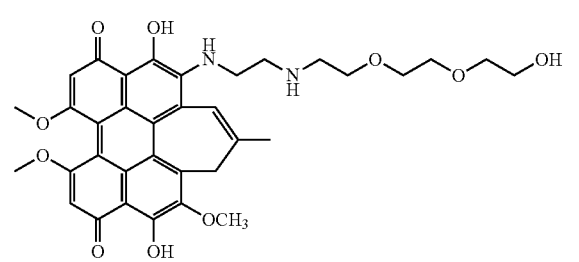

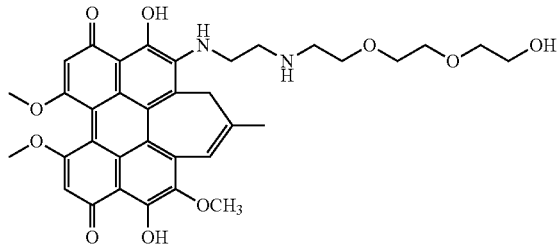

Example 21

Preparation of an aminoethylthio-substituted diglycol-modified hypocrellin B derivative (R=—CH$_2$CH$_2$—S—CH$_2$CH$_2$—OCH$_2$CH$_2$—OH): the synthesis method similar to the preparation of an aminoethyl glycol-modified hypocrellin B derivative in Example 3. 2,17-amino-substituted product HB-37: yield: 11.4%, Rf: 0.35, MS (ESI+) 809.0, maximum UV absorption wavelength: 475 nm, 640 nm. 2-amino-substituted product HB-38: yield: 7.4%, Rf: 0.68, MS (ESI+) 662.3, maximum UV absorption wavelength: 470 nm, 630 nm. The amino-substituted products HB-37 and HB-38 have the structural formulas as shown in the figure:

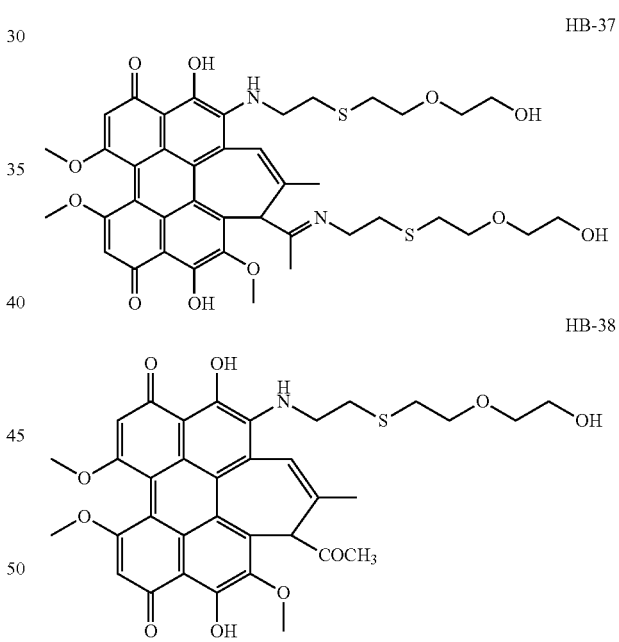

Example 22

Preparation of an aminoethylthio-substituted pentaglycol-modified deacetylated hypocrellin B derivative (R=—(CH$_2$CH$_2$—S—CH$_2$CH$_2$—(OCH$_2$CH$_2$)$_3$—OH): the synthesis method similar to the preparation of a 3-aminopropanol-modified deacetylated hypocrellin derivative in Example 4.

The resulting product: yield: 17.5%, Rf: 0.12; characterization data as follows: MS (ESI+): 709.0. Maximum UV absorption wavelength: 480 nm, 635 nm. The amino-substituted product HC-39 (double bond located at C$_{13}$=C$_{14}$) or HC-40 (double bond located at C$_{14}$=C$_{15}$) has the structural formula as shown in the figure:

HC-39

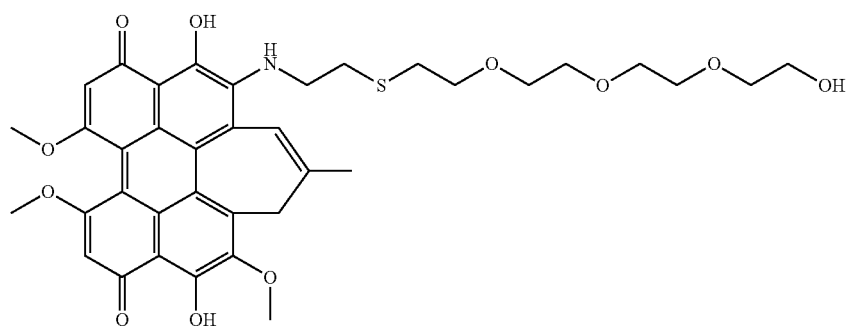

HC-40

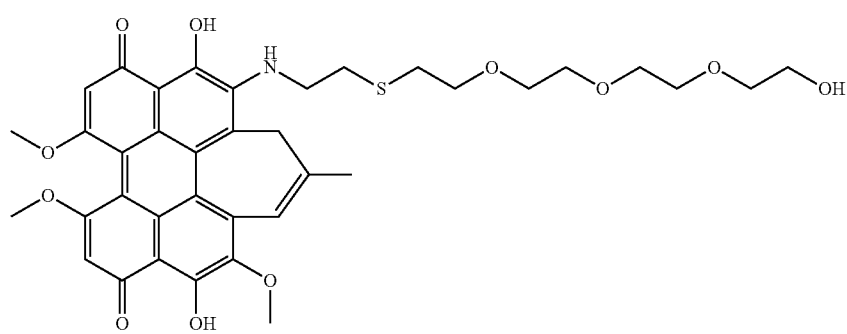

Example 23

Preparation of a methyl tetraglycol aminopropanamide-modified hypocrellin B derivative (R=—CH$_2$CH$_2$CONH—CH$_2$CH$_2$—(OCH$_2$CH$_2$)$_3$—OCH$_3$): the synthesis method similar to the preparation of an aminoethyl glycol-modified hypocrellin B derivative in Example 3. 2,17-amino-substituted product HB-41: yield: 7.8%, Rf: 0.15, MS (ESI+) 1035.2, maximum UV absorption wavelength: 461 nm, 643 nm. 2-amino-substituted product HB-42: yield: 5.4%, Rf: 0.54, MS (ESI+) 775.1, maximum UV absorption wavelength: 458 nm, 622 nm. The amino-substituted products HB-41 and HB-42 have the structural formulas as shown in the figure:

HB-41

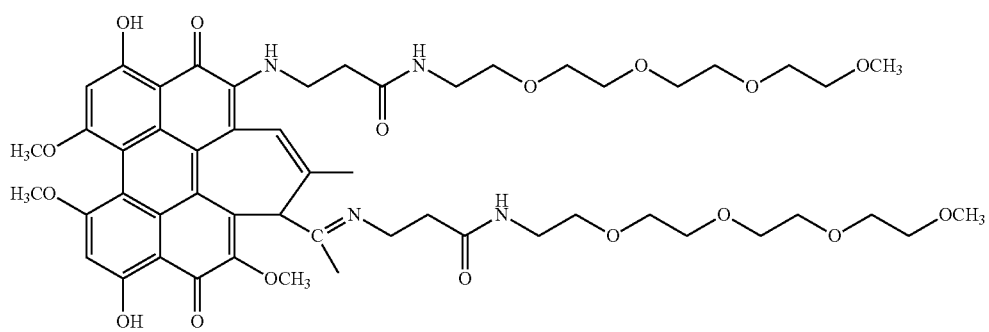

HB-42

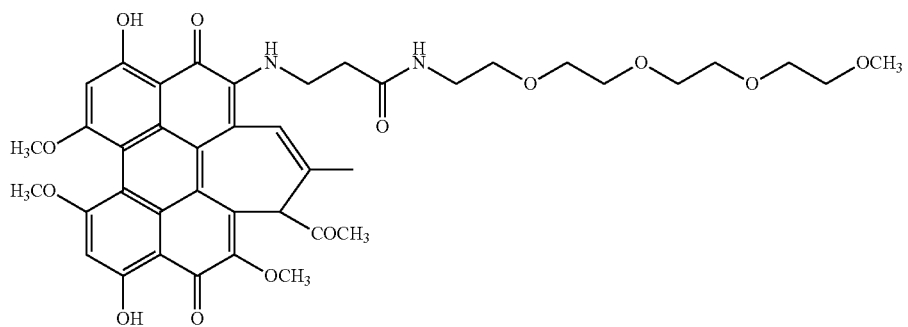

Example 24

Preparation of a tetraethylene glycol aminopentanamide-modified hypocrellin B derivative (R=—(CH$_2$)$_4$CH$_2$CONH—CH$_2$CH$_2$—(OCH$_2$CH$_2$)$_3$—OCH$_3$): the synthesis method similar to the preparation of a 3-aminopropanol-modified deacetylated hypocrellin derivative in Example 4. The resulting product: yield: 16.5%; Rf: 0.21; MS (ESI+) 760.5; maximum UV absorption wavelength: 455 nm, 642 nm. The amino-substituted product HC-43 (double bond located at C$_{13}$=C$_{14}$) or HC-44 (double bond located at C$_{13}$=C$_{14}$) has the structural formula as shown in the figure:

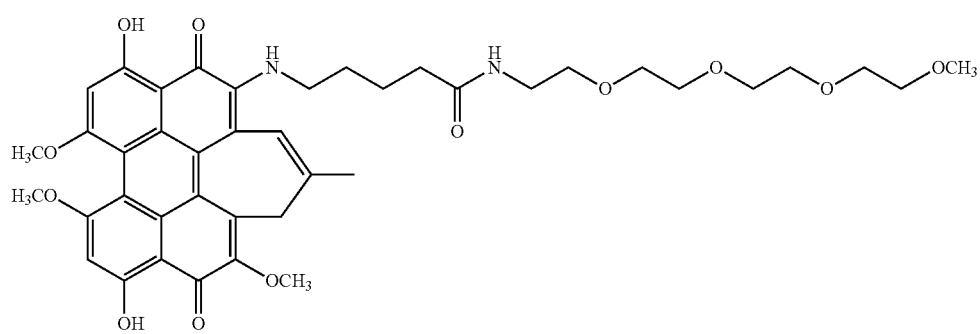

HC-43

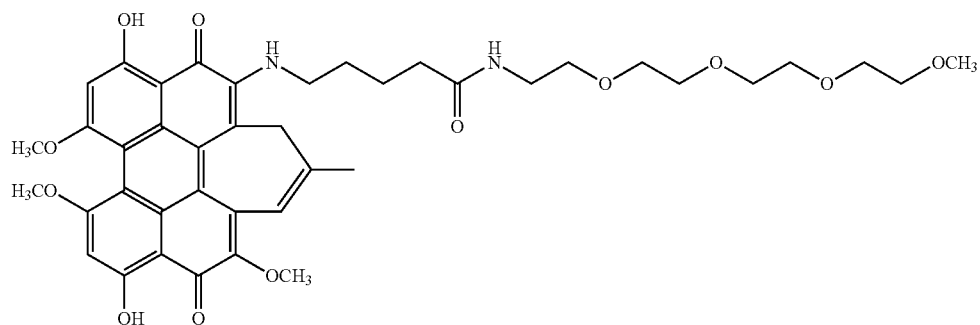

HC-44

Example 25

Preparation of a hexylamine-modified hypocrellin B derivative (R=—CH$_2$CH$_2$CH$_2$CH$_2$CH$_2$CH$_3$): a hypocrellin B (HB) (100 mg, 0.18 mmol) and hexylamine (0.51 g, 5 mmol) were dissolved in 50 mL of anhydrous acetonitrile, heated to 55° C. under nitrogen protection, and stirred in dark for 8 h. Then the solvent was removed by rotary evaporation. A blue black solid residue was dissolved in 200 mL of dichloromethane, and successively washed with diluted aqueous hydrochloric acid solution twice and with distilled water once. The organic layer was dried, and filtered, and then the organic phase was spin-dried to obtain a crude product. The resulting crude product was separated by thin layer silica gel chromatography with acetone:petroleum ether (volume ratio: 2:1) as a developer to obtain two blue black solid products. 2,17-amino-substituted product HB-45: yield: 28.6%, Rf: 0.24, MS (ESI+) 695.4, maximum UV absorption wavelength: 455 nm, 635 nm. 2-amino-substituted product HB-46: yield: 14.6%, Rf: 0.38, MS (ESI+) 598.2, maximum UV absorption wavelength: 452 nm, 626 nm. The amino-substituted products HB-45 and HB-46 have the structural formulas as shown in the figure:

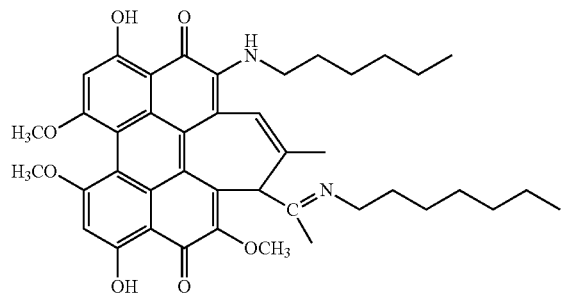

HB-45

-continued

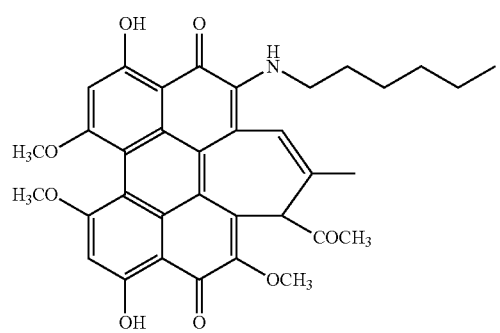

HB-46

Example 26

Preparation of a butylamine-modified hypocrellin B derivative (R=—CH$_2$CH$_2$CH$_2$CH$_3$): the synthesis method similar to the preparation of a hexylamine-modified hypocrellin derivative in Example 25. 2,17-amino-substituted product HB-47: yield: 32.6%, Rf: 0.26, MS (ESI+) 625.4, maximum UV absorption wavelength: 454 nm, 632 nm. 2-amino-substituted product HB-48: yield: 14.6%, Rf: 0.38, MS (ESI+) 570.2, maximum UV absorption wavelength: 448 nm, 624 nm. The amino-substituted products HB-47 and HB-48 have the structural formulas as shown in the figure:

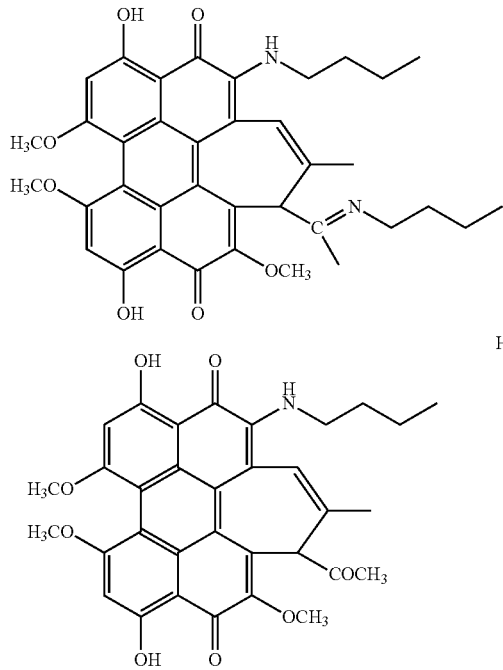

HB-47

HB-48

Example 27

Preparation of an octylamine-modified hypocrellin B derivative (R=—CH$_2$CH$_2$CH$_2$CH$_2$CH$_2$CH$_2$CH$_2$CH$_3$): the synthesis method similar to the preparation of a hexylamine-modified hypocrellin derivative in Example 25. 2,17-amino-substituted product HB-49: yield: 22.6%, Rf: 0.16, MS (ESI+) 737.4, maximum UV absorption wavelength: 452 nm, 632 nm. 2-amino-substituted product HB-50: yield: 18.6%, Rf: 0.60, MS (ESI+) 626.2, maximum UV absorption wavelength: 445 nm, 621 nm. The amino-substituted products HB-49 and HB-50 have the structural formulas as shown in the figure:

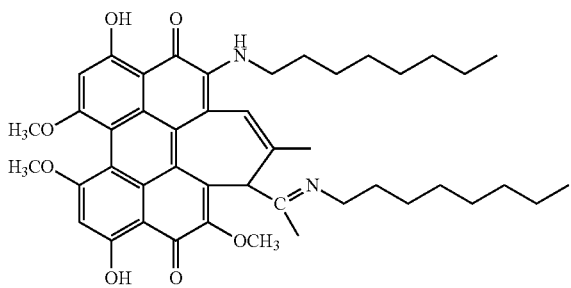

HB-49

-continued

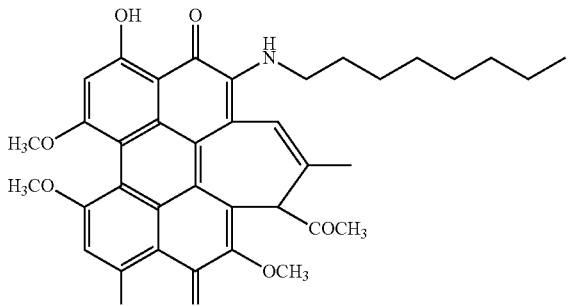

HB-50

Example 28

Preparation of a butylhexylamine-modified hypocrellin B derivative (R=—CH$_2$CH$_2$CH$_2$CH$_2$): the synthesis method similar to the preparation of a hexylamine-modified hypocrellin derivative in Example 25. The resulting product: yield: 38.6%; Rf: 0.24; MS (ESI+) 528.4; maximum UV absorption wavelength: 455 nm, 635 nm. The amino-substituted product HC-51 (double bond located at C$_{13}$=C$_{14}$) or HC-52 (double bond located at C$_{14}$=C$_{15}$) has the structural formula as shown in the figure:

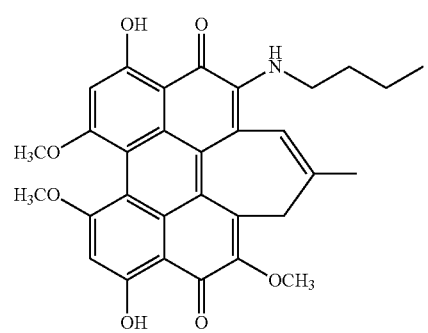

HC-51

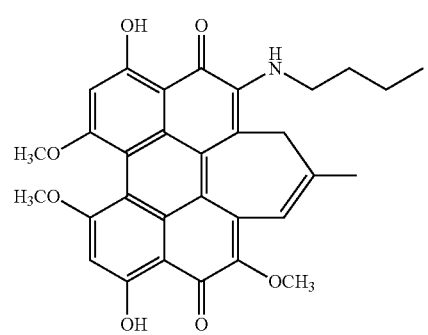

HC-52

Example 29

Preparation of a benzylamino hypocrellin B derivative (R=—CH$_2$C$_6$H$_5$): the synthesis method similar to the preparation of a hexylamine-modified hypocrellin derivative in Example 25. 2,17-amino-substituted product HB-53: yield: 25.4%, Rf: 0.22, MS (ESI+) 691.2, maximum UV absorption wavelength: 453 nm, 642 nm. 2-amino-substituted product HB-54: yield: 14.5%, Rf: 0.45, MS (ESI+) 604.9.

Maximum UV absorption wavelength: 453 nm, 622 nm. The amino-substituted products HB-53 and HB-54 have the structural formulas as shown in the figure:

HB-53

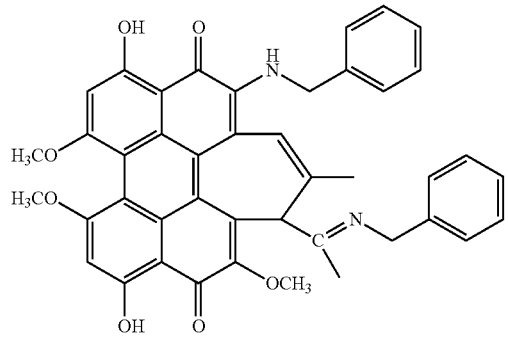

HB-54

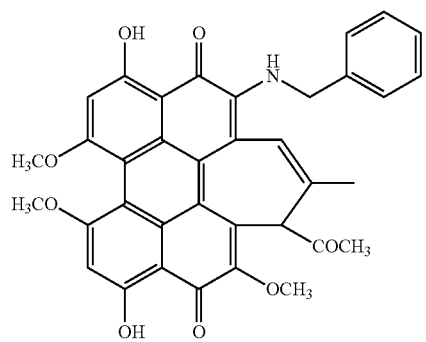

Example 30

Preparation of a phenylbutylamine-modified hypocrellin B derivative (R=—CH$_2$CH$_2$CH$_2$CH$_2$C$_6$H$_5$): the synthesis method similar to the preparation of a hexylamine-modified hypocrellin derivative in Example 25. 2,17-amino-substituted product HB-55: yield: 17.5%, Rf: 0.23, MS (ESI+) 1037.5, maximum UV absorption wavelength: 452 nm, 636 nm. 2-amino-substituted product HB-56: yield: 14.8%, Rf: 0.36, MS (ESI+) 776.3, maximum UV absorption wavelength: 452 nm, 619 nm. The amino-substituted products HB-55 and HB-56 have the structural formulas as shown in the figure:

HB-55

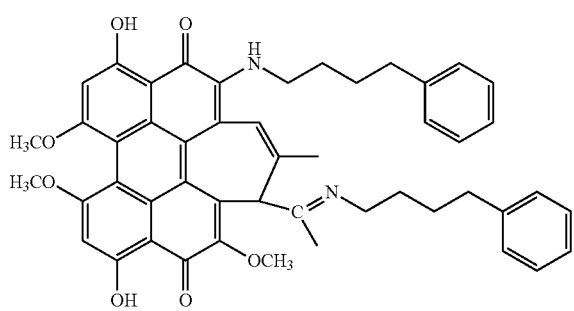

HB-56

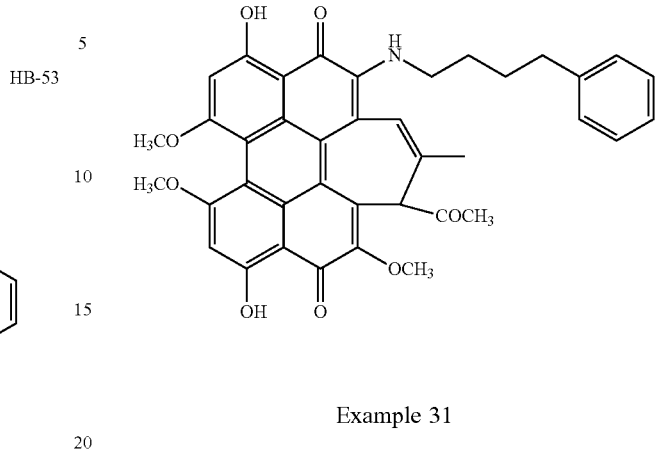

Example 31

Preparation of a 2-methylpyridin-amino hypocrellin B derivative (R=—CH$_2$C$_5$H$_4$N): the synthesis method similar to the preparation of a hexylamine-modified hypocrellin derivative in Example 25. 2,17-amino-substituted product HB-57: yield: 25.4%, Rf: 0.22, MS (ESI+) 693.2, maximum UV absorption wavelength: 453 nm, 634 nm. 2-amino-substituted product HB-58: yield: 14.5%, Rf: 0.45, MS (ESI+) 606.9, maximum UV absorption wavelength: 450 nm, 622 nm. The amino-substituted products HB-57 and HB-58 have the structural formulas as shown in the figure:

HB-57

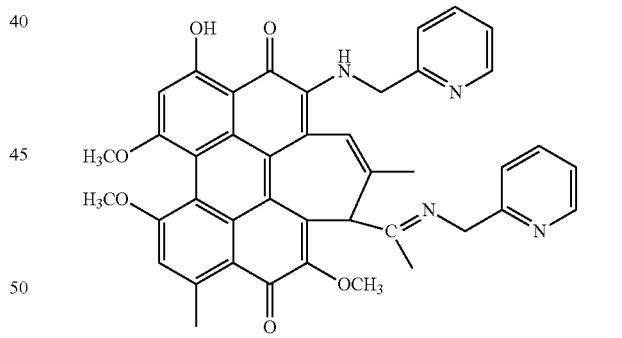

HB-58

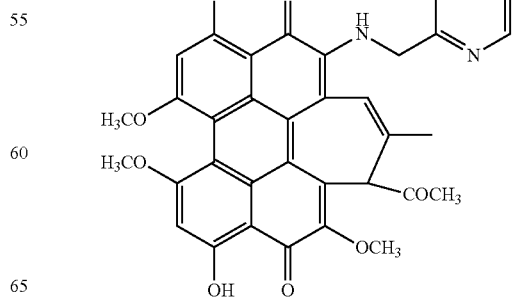

Example 32

Preparation of a phenylbutylamine-modified deacetylated hypocrellin B derivative (R=—CH$_2$CH$_2$CH$_2$CH$_2$C$_5$H$_4$N): the synthesis method similar to the preparation of a hexylamine-modified hypocrellin derivative in Example 25. The resulting product: yield: 17.5%; Rf: 0.23; MS (ESI+) 605.5; maximum UV absorption wavelength: 452 nm, 636 nm. The amino-substituted product HC-59 (double bond located at C$_{13}$═C$_{14}$) or HC-60 (double bond located at C$_{14}$═C$_{15}$) has the structural formula as shown in the figure:

HC-59

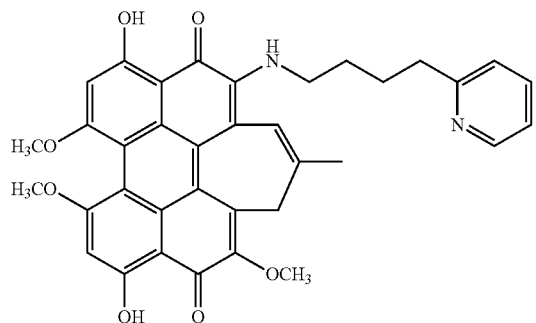

HC-60

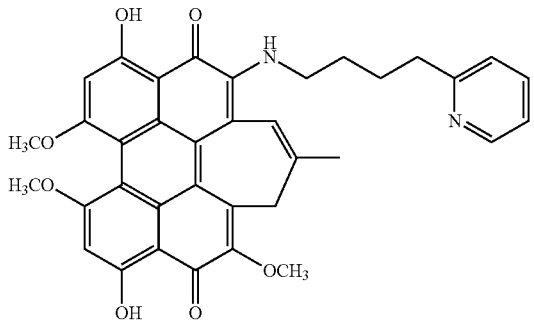

Example 33

Preparation of a 4-methylpyridin-butylamino hypocrellin B derivative (R=—(CH$_2$)$_4$C$_5$H$_4$N$^+$(C$_6$H$_{11}$)): the synthesis method similar to the preparation of a hexylamine-modified hypocrellin derivative in Example 25. 2,17-amino-substituted product HB-61: yield: 15.4%, Rf: 0.22, MS (ESI+) 984.2, maximum UV absorption wavelength: 453 nm, 634 nm. 2-amino-substituted product HB-62: yield: 14.5%, Rf: 0.45, MS (ESI+) 767.9, maximum UV absorption wavelength: 450 nm, 622 nm. The amino-substituted products HB-61 and HB-62 have the structural formulas as shown in the figure:

HB-61

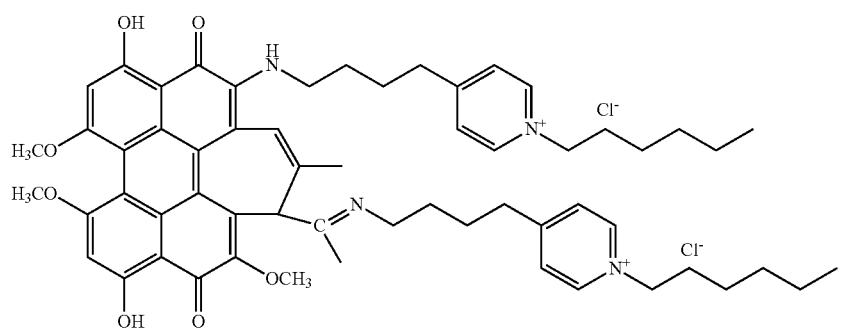

HB-62

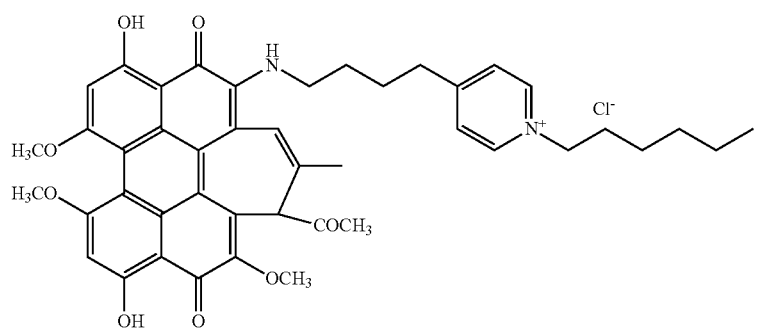

Example 34

Preparation of hypocrellin B hydrazine (R=—NH₂): the synthesis method similar to the preparation of a hexylamine-modified hypocrellin derivative in Example 25. 2,17-amino-substituted product HB-63: yield: 25.4%, Rf: 0.28, MS (ESI+) 543.8, maximum UV absorption wavelength: 455 nm, 640 nm. 2-amino-substituted product HB-64: yield: 12.6%, Rf: 0.48, MS (ESI+) 529.9, maximum UV absorption wavelength: 448 nm, 625 nm. The amino-substituted products HB-63 and HB-64 have the structural formulas as shown in the figure:

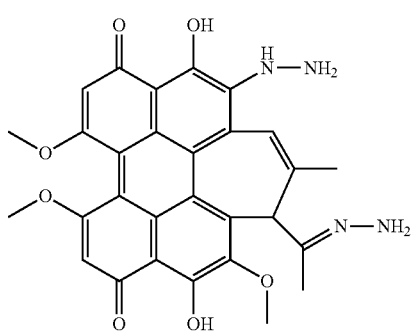

HB-63

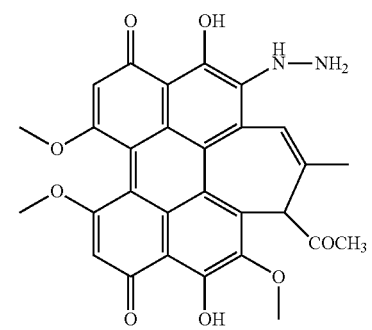

HB-64

Example 35

Preparation of deacetylated hypocrellin B hydrazine (R=—NH₂): the synthesis method similar to the preparation of a hexylamine-modified hypocrellin derivative in Example 25. The resulting product: yield: 28.5%; Rf: 0.30; MS (ESI+) 486.8; maximum UV absorption wavelength: 456 nm, 642 nm. The amino-substituted product HC-65 (double bond located at $C_{13}$=$C_{14}$) or HC-66 (double bond located at $C_{14}$=$C_{15}$) has the structural formula as shown in the figure:

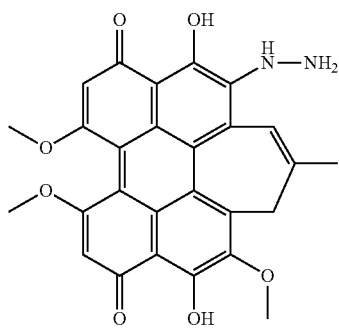

HC-65

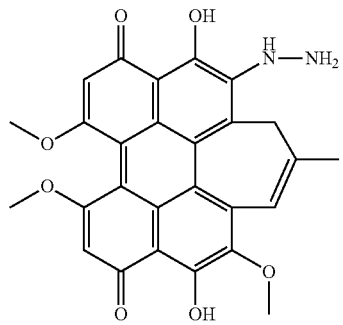

HC-66

Example 36

Preparation of hypocrellin B hydrazine (R=—OH): the synthesis method similar to the preparation of a hexylamine-modified hypocrellin derivative in Example 25. 2,17-amino-substituted product HB-67: yield: 28.6%, Rf: 0.22, MS (ESI+) 545.8, maximum UV absorption wavelength: 452 nm, 632 nm. 2-amino-substituted product HB-68: yield: 15.6%, Rf: 0.46, MS (ESI+) 531.9, maximum UV absorption wavelength: 445 nm, 622 nm. The amino-substituted products HB-67 and HB-68 have the structural formulas as shown in the figure:

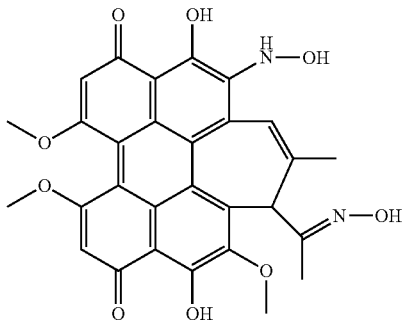

HB-67

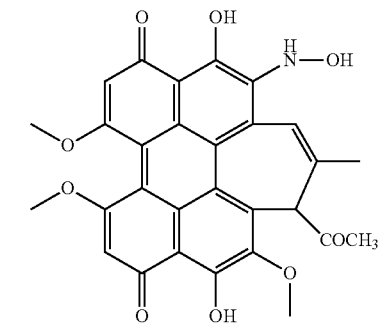

HB-68

Example 37

Preparation of deacetylated hypocrellin B hydrazine (R=—OH): the synthesis method similar to the preparation of a hexylamine-modified hypocrellin derivative in Example 25. The resulting product: yield: 21.5%; Rf: 0.28; MS (ESI+) 488.8; maximum UV absorption wavelength: 452 nm, 640 nm. The amino-substituted product HC-69 (double bond located at $C_{13}=C_{14}$) or HC-70 (double bond located at $C_{14}=C_{15}$) has the structural formula as shown in the figure:

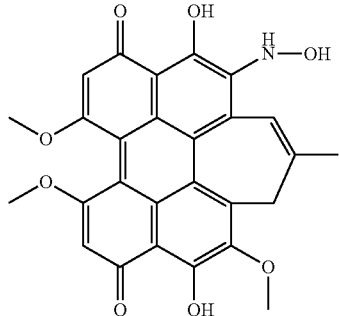

HC-69

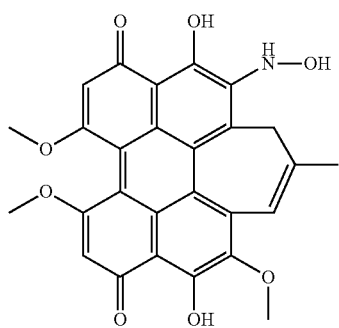

HC-70

Example 38

Preparation of cyclohexylamine-modified hypocrellin (R=—$C_6H_{11}$): the synthesis method similar to the preparation of a hexylamine-modified hypocrellin derivative in Example 25. 2,17-amino-substituted product HB-71: yield: 58.6%, Rf: 0.58, MS (ESI+) 677.5, maximum UV absorption wavelength: 448 nm, 626 nm. 2-amino-substituted product HB-72: yield: 12.6%, Rf: 0.82, MS (ESI+) 596.9, maximum UV absorption wavelength: 446 nm, 618 nm. The amino-substituted products HB-71 and HB-72 have the structural formulas as shown in the figure:

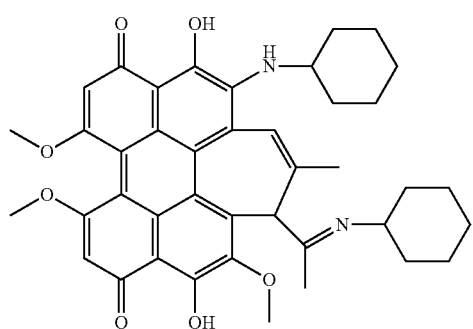

HB-71

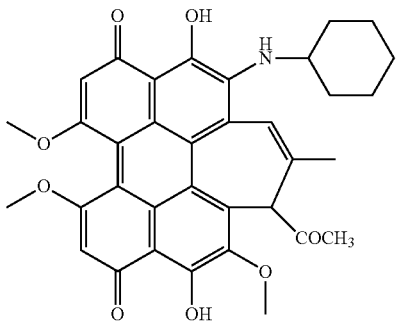

HB-72

Example 39

Preparation of cyclohexylamine-modified deacetylated hypocrellin (R=—$C_6H_{11}$): the synthesis method similar to the preparation of a hexylamine-modified hypocrellin derivative in Example 25. The resulting product: yield: 26.4%; Rf: 0.30; MS (ESI+) 553.8; maximum UV absorption wavelength: 450 nm, 638 nm. The amino-substituted product HC-73 (double bond located at $C_{13}=C_{14}$) or HC-74 (double bond located at $C_{14}=C_{15}$) has the structural formula as shown in the figure:

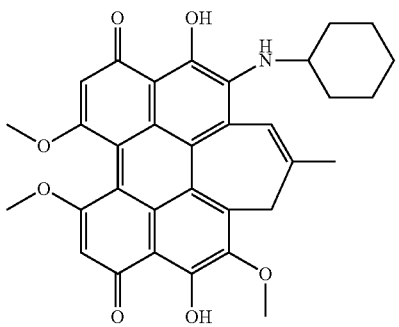

HC-73

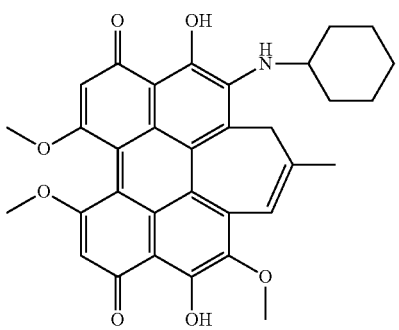

HC-74

Example 40

Preparation of cyclobutylamine-modified hypocrellin (R=—$C_4H_7$): the synthesis method similar to the preparation of a hexylamine-modified hypocrellin derivative in Example 25. 2,17-amino-substituted product HB-75: yield: 35.6%, Rf: 0.52, MS (ESI+) 621.5, maximum UV absorption wavelength: 450 nm, 630 nm. 2-amino-substituted product HB-76: yield: 15.6%, Rf: 0.80, MS (ESI+) 568.9, maximum UV absorption wavelength: 448 nm, 622 nm. The amino-substituted products HB-75 and HB-76 have the structural formulas as shown in the figure:

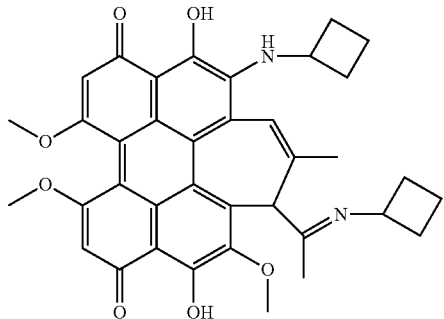

HB-75

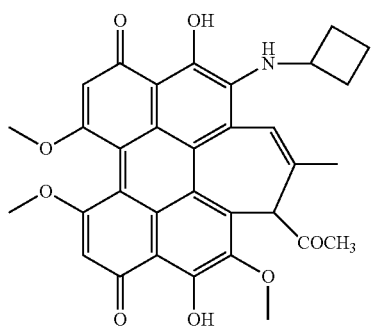

HB-76

Example 41

Preparation of cyclopentylamine-modified hypocrellin (R=—C₅H₉): the synthesis method similar to the preparation of a hexylamine-modified hypocrellin derivative in Example 25. 2,17-amino-substituted product HB-77: yield: 25.8%, Rf: 0.56, MS (ESI+) 649.5, maximum UV absorption wavelength: 452 nm, 632 nm. 2-amino-substituted product HB-78: yield: 10.2%, Rf: 0.85, MS (ESI+) 581.9, maximum UV absorption wavelength: 450 nm, 625 nm. The amino-substituted products HB-77 and HB-78 have the structural formulas as shown in the figure:

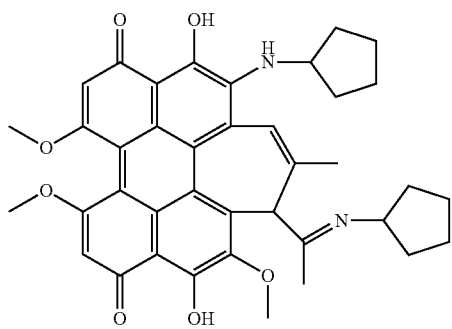

HB-77

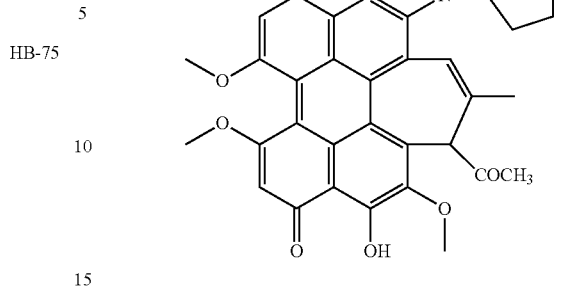

HB-78

Example 42

Preparation of cycloheptylamine-modified hypocrellin (R=—O5H₉): the synthesis method similar to the preparation of a hexylamine-modified hypocrellin derivative in Example 25. 2,17-amino-substituted product HB-79: yield: 28.1%, Rf: 0.58, MS (ESI+) 705.5, maximum UV absorption wavelength: 454 nm, 634 nm. 2-amino-substituted product HB-80: yield: 15.0%, Rf: 0.75, MS (ESI+) 610.2. Maximum UV absorption wavelength: 452 nm, 627 nm. The amino-substituted products HB-79 and HB-80 have the structural formulas as shown in the figure:

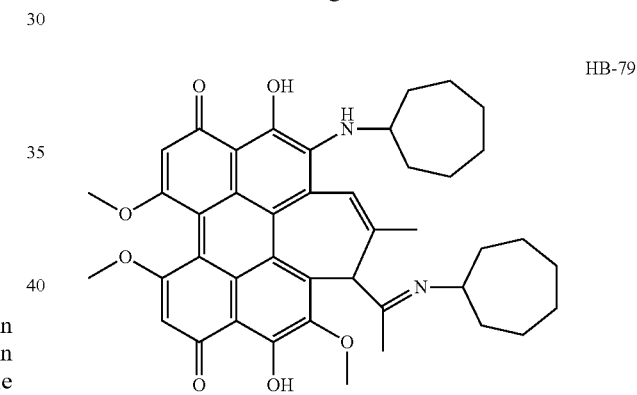

HB-79

HB-80

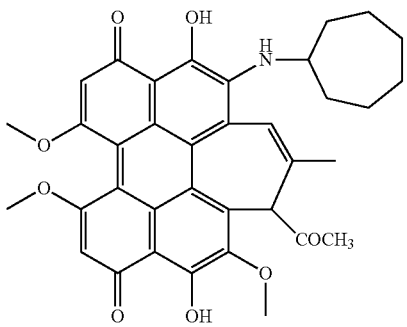

Example 43

Preparation of p-methyl-cyclohexylamine-modified hypocrellin (R=—C₆H₁₀CH₃): the synthesis method similar to the preparation of a hexylamine-modified hypocrellin derivative in Example 25. 2,17-amino-substituted product HB-81: yield: 46.6%, Rf: 0.52, MS (ESI+) 705.5, maximum UV absorption wavelength: 450 nm, 628 nm. 2-aminosubstituted product HB-82: yield: 10.1%, Rf: 0.80, MS (ESI+) 610.4, maximum UV absorption wavelength: 448 nm, 621 nm. The amino-substituted products HB-81 and HB-82 have the structural formulas as shown in the figure:

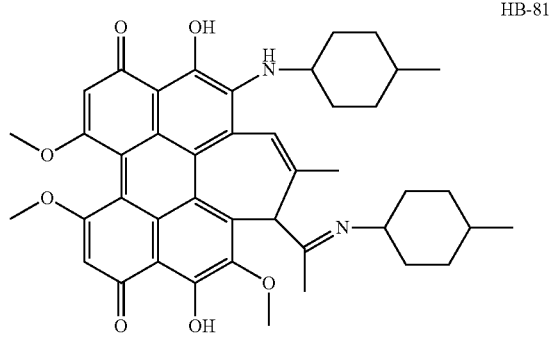

HB-81

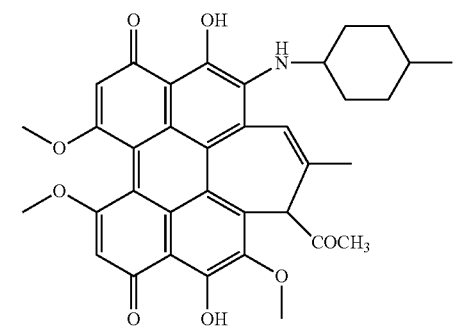

HB-82

Example 44

Preparation of 4-aminopiperidine-modified hypocrellin (R=–C$_5$H$_{10}$N): the synthesis method similar to the preparation of a hexylamine-modified hypocrellin derivative in Example 25. 2,17-amino-substituted product HB-83: yield: 26.5%, Rf: 0.50, MS (ESI+) 679.5, maximum UV absorption wavelength: 452 nm, 630 nm. 2-amino-substituted product HB-84: yield: 20.1%, Rf: 0.82, MS (ESI+) 597.4, maximum UV absorption wavelength: 450 nm, 625 nm. The amino-substituted products HB-81 and HB-82 have the structural formulas as shown in the figure:

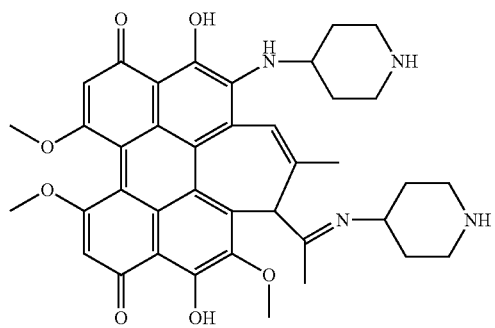

HB-83

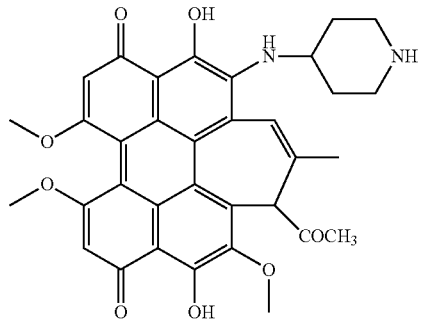

HB-84

Example 45

Preparation of 3-butenylamine-modified hypocrellin (R=–C$_4$H$_7$): the synthesis method similar to the preparation of a hexylamine-modified hypocrellin derivative in Example 25. 2,17-amino-substituted product HB-85: yield: 16.5%, Rf: 0.52, MS (ESI+) 621.7, maximum UV absorption wavelength: 450 nm, 632 nm. 2-amino-substituted product HB-86: yield: 28.1%, Rf: 0.84, MS (ESI+) 568.9. Maximum UV absorption wavelength: 451 nm, 628 nm. The amino-substituted products HB-85 and HB-86 have the structural formulas as shown in the figure:

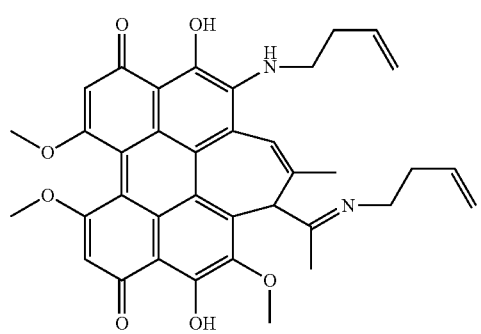

HB-85

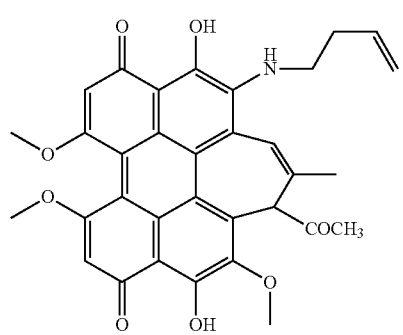

HB-86

Example 46

Figure 4:
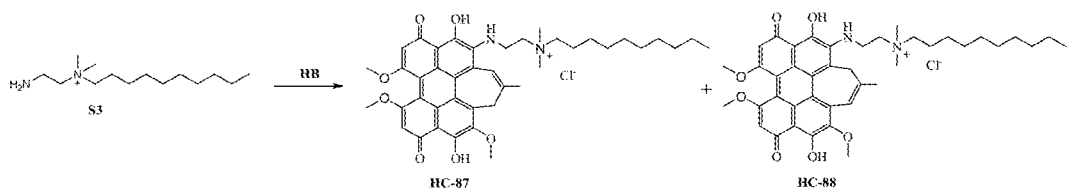
FIG. 4 shows a synthesis reaction route map of a deacetylated hypocrellin derivative containing a long chain quaternary ammonium salt according to Example 46 of the invention.

Preparation of N,N-dimethyl-N-decylamino-ethyl-diamino deacetylated hypocrellin B (R=—CH$_2$CH$_2$—N$^+$(CH$_3$)$_2$(C$_{10}$H$_{21}$)): the synthesis route as shown in FIG. 4: deacetylated hypocrellin HC (100 mg, 0.18 mmol) and a long chain quaternary ammonium salt derivative S3 (224 mg, 0.72 mmol) prepared in Example 3 were dissolved in 20 mL of anhydrous acetonitrile, fully mixed, heated to 50° C. under nitrogen protection, and stirred in dark for 10 h. On completion of the reaction, the solvent was removed by rotary evaporation. A blue black solid residue was dissolved in 200 mL of dichloromethane, and successively washed with 50 mL of diluted aqueous hydrochloric acid solution once and with distilled water twice. The organic layer was dried with anhydrous magnesium sulfate, and filtered, and then the organic phase was spin-dried to obtain a crude product. The resulting crude product was further separated by silica gel chromatography with acetone:ethyl acetate:ethanol:diethylamine (volume ratio: 20:1:1:3) as a developer to respectively obtain two blue black solid products. The resulting product: yield: 24.2%; Rf: 0.37; MS (ESI+) 684.5; maximum UV absorption wavelength: 453 nm, 630 nm. The amino-substituted product HC-87 (double bond located at $C_{13}=C_{14}$) or HC-88 (double bond located at $C_{14}=C_{15}$) has the structural formula as shown in the figure:

HC-87

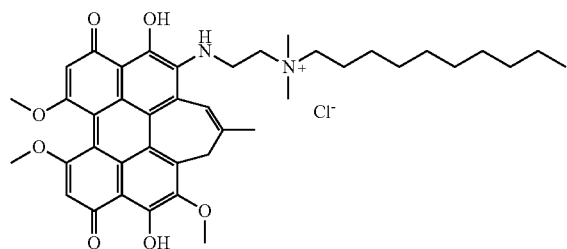

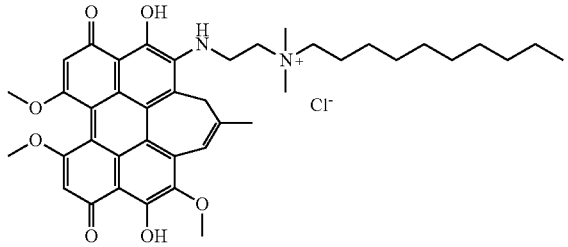

Example 47

Preparation of N,N-dimethyl-N-dodecylamine-butyl-diamino hypocrellin B (R=—$CH_2CH_2CH_2CH_2$—$N^+(CH_3)_2$ ($C_{12}H_{23}$): the synthesis method similar to the preparation of a quaternary ammonium salt-containing hypocrellin derivative in Example 46. The resulting 2-amino-substituted product: yield: 15.4%, Rf: 0.36. Characterization data as follows: MS (ESI+): 739.5; Maximum UV absorption wavelength: 462 nm, 624 nm. The amino-substituted product HC-89 (double bond located at $C_{13}=C_{14}$) or HC-90 (double bond located at $C_{14}=C_{15}$) has the structural formula as shown in the figure:

HC-89

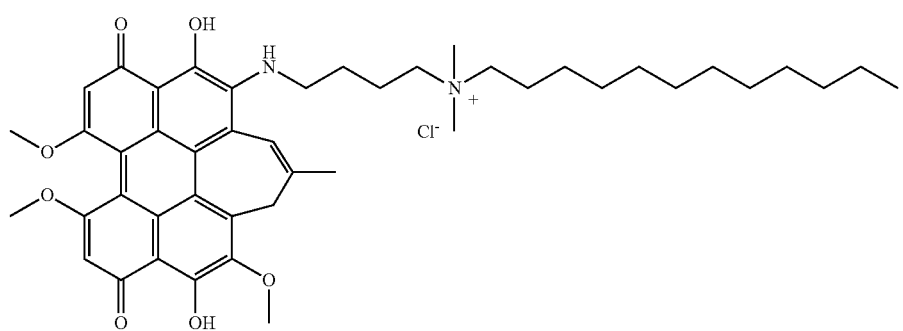

HC-90

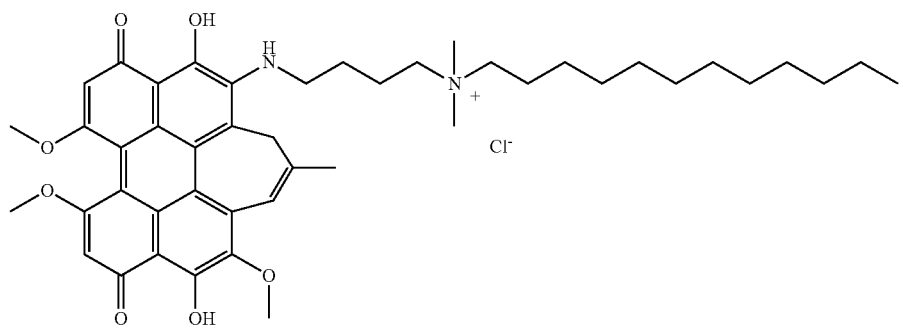

Example 48

Preparation of N,N,N-trimethylammonium-decyldiamino hypocrellin B (R=—(CH$_2$)$_{10}$—N$^+$(CH$_3$)$_3$: the synthesis method similar to the preparation of a quaternary ammonium salt-containing hypocrellin derivative in Example 46. The resulting 2-amino-substituted product: yield: 8.8%, Rf: 0.35. Characterization data as follows: MS (ESI+): 791.2; Maximum UV absorption wavelength: 464 nm, 626 nm. The amino-substituted product HC-91 (double bond located at C$_{13}$=C$_{14}$) or HC-92 (double bond located at C$_{14}$=C$_{15}$) has the structural formula as shown in the figure:

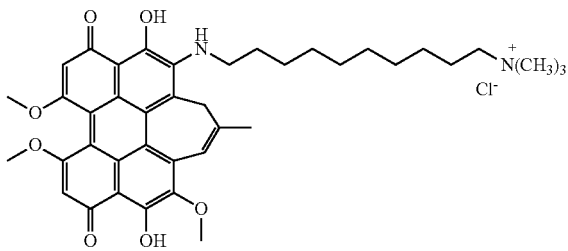

HC-92

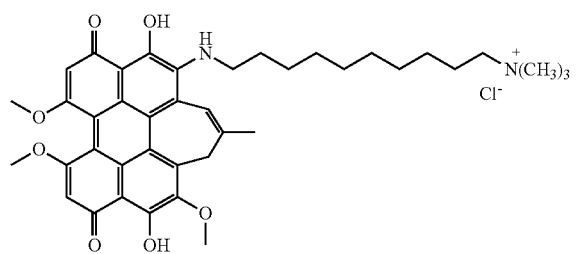

HC-91

Example 49

Preparation of N,N-dimethyl-N-decyl-PEG-amino hypocrellin (R=—CH$_2$CH$_2$OCH$_2$CH$_2$OCH$_2$CH$_2$—N$^+$(CH$_3$)$_2$ (C$_{10}$H$_{21}$): the synthesis method similar to the preparation of quaternary ammonium salt-containing hypocrellin derivative in Example 46. The resulting 2-amino-substituted product: yield: 15.5%, Rf: 0.28. Characterization data as follows: MS (ESI+): 771.2; Maximum UV absorption wavelength: 462 nm, 628 nm. The amino-substituted product HC-93 (double bond located at C$_{13}$=C$_{14}$) or HC-94 (double bond located at C$_{14}$=C$_{15}$) has the structural formula as shown in the figure:

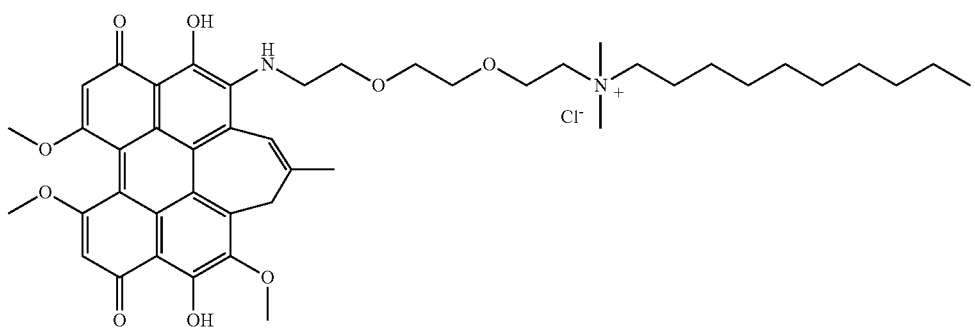

HC-93

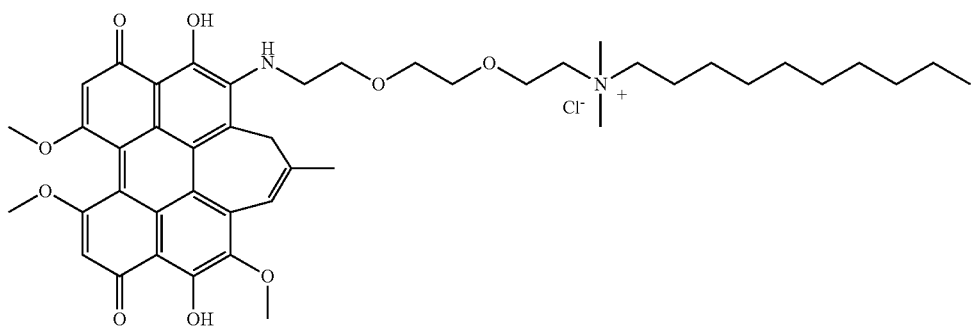

HC-94

Example 50

Preparation of piperazino (deacetylated hypocrellin): deacetylated hypocrellin HC (100 mg, 0.20 mmol) and ethyldiamine (421 mg, 2 mmol) were dissolved in 20 mL of anhydrous acetonitrile, fully mixed, heated to 45° C. under nitrogen protection, and stirred in dark for 6 h. On completion of the reaction, the solvent was removed by rotary evaporation. A blue black solid residue was dissolved in 100 mL of dichloromethane, washed with 50 mL of diluted aqueous hydrochloric acid solution thrice, and then washed with distilled water once. The organic layer was dried with anhydrous magnesium sulfate, and filtered, and then the organic phase was spin-dried to obtain a crude product. The resulting crude product was further separated by silica gel chromatography with acetone:ethyl acetate:ethanol:diethylamine (volume ratio: 20:1:1:1) as a developer to obtain a blue black solid product with a yield of 49.8% and with Rf of 0.45. Characterization data of the product as follows: ESI MS: m/z, 497.3. Maximum UV absorption wavelength: 462 nm, 650 nm. The product is respectively represented by structural formula HC-95:

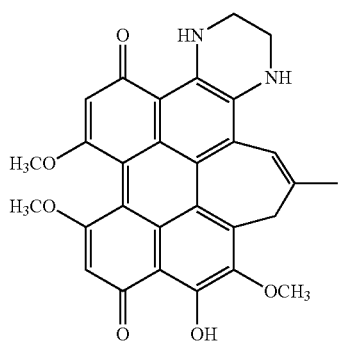

HC-95

Example 51

Preparation of methylpiperazino (deacetylated hypocrellin B): the preparation method similar to the preparation of piperazino (deacetylated hypocrellin) in Example 50. Yield: 59.8%, Rf: 0.60. Characterization data of the product as follows: ESI MS: m/z, 511.3. Maximum UV absorption wavelength: 465 nm, 652 nm. The product is respectively represented by structural formula HC-96 or HC-97:

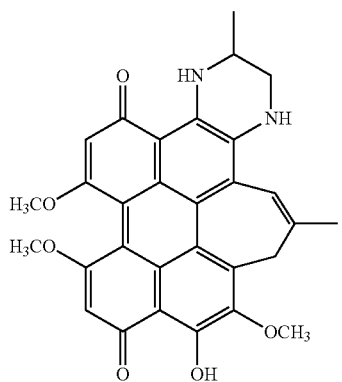

HC-96

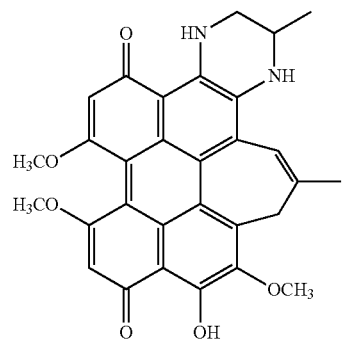

HC-97

Example 52

Preparation of dimethylpiperazino(hypocrellin B): A hypocrellin B (HB) (100 mg, 0.18 mmol) and dimethyl ethyldiamine (421 mg, 2 mmol) were dissolved in 20 mL of anhydrous acetonitrile, fully mixed, heated to 45° C. under nitrogen protection, and stirred in dark for 6 h. On completion of the reaction, the solvent was removed by rotary evaporation. A blue black solid residue was dissolved in 100 mL of dichloromethane, washed with 50 mL of diluted aqueous hydrochloric acid solution thrice, and then washed with distilled water once. The organic layer was dried with anhydrous magnesium sulfate, and filtered, and then the organic phase was spin-dried to obtain a crude product. The resulting crude product was further separated by silica gel chromatography with acetone:ethylacetate:ethanol:diethylamine (volume ratio: 20:1:1:1) as a developer to obtain a blue black solid product with a yield of 19.8% and with Rf of 0.45. Characterization data of the product as follows: ESI MS: m/z, 569.3. Maximum UV absorption wavelength: 462 nm, 650 nm. The product is respectively represented by structural formula HC-98 or HC-99:

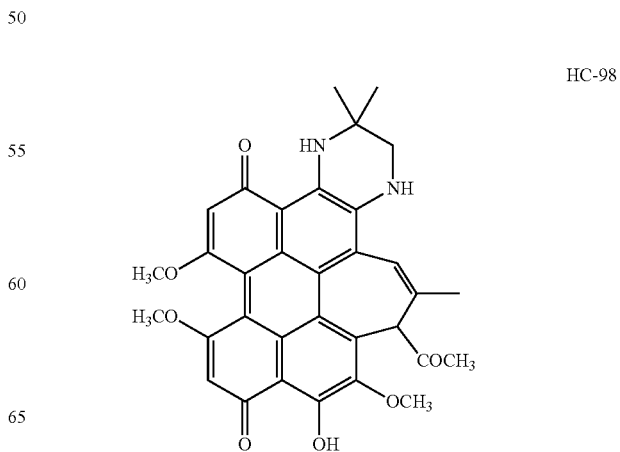

HC-98

-continued

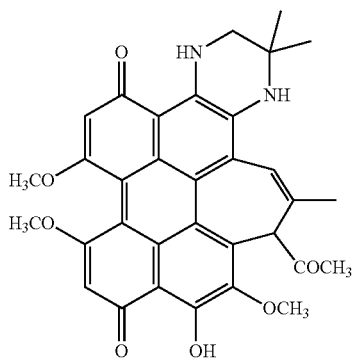

HC-99

Example 53

Preparation of diethylpiperazino(hypocrellin B): the synthesis method similar to the preparation of dimethylpiperazino(hypocrellin B) in Example 52. Yield: 18.8%, Rf: 0.38. Characterization data of the product as follows: ESI MS: m/z, 596.8. Maximum UV absorption wavelength: 465 nm, 655 nm. The product is respectively represented by structural formula HC-99 or HC-100:

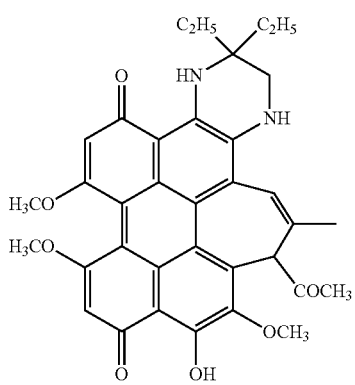

HC-99

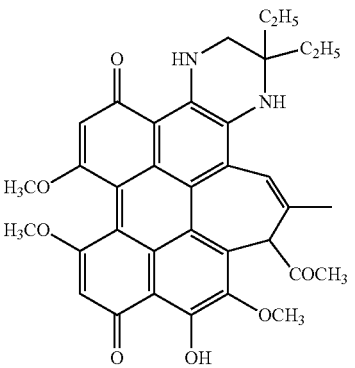

HC-100

Example 54

Preparation of dipropylpiperazino(hypocrellin B): the synthesis method similar to the preparation of dimethylpiperazino(hypocrellin B) in Example 52. Yield: 21.2%, Rf: 0.35. Characterization data of the product as follows: ESI MS: m/z, 596.8. Maximum UV absorption wavelength: 462 nm, 652 nm. The product is respectively represented by structural formula HC-101 or HC-102:

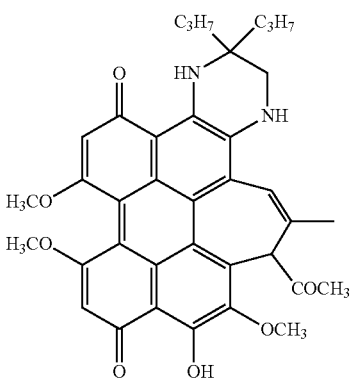

HC-101

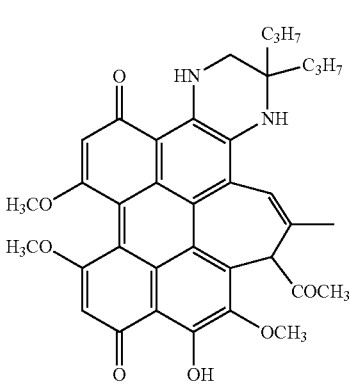

HC-102

Example 55

Preparation of dibutylpiperazino(hypocrellin B): the synthesis method similar to the preparation of dimethylpiperazino(hypocrellin B) in Example 52. Yield: 21.5%, Rf: 0.38. Characterization data of the product as follows: ESI MS: m/z, 609.8. Maximum UV absorption wavelength: 468 nm, 657 nm. The product is respectively represented by structural formula HC-103 or HC-104:

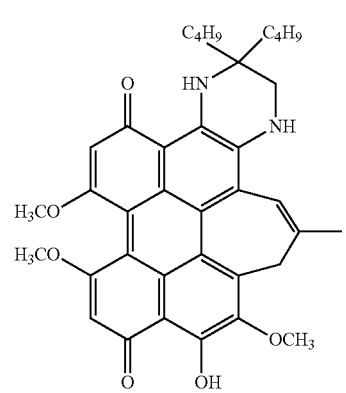

HC-103

-continued

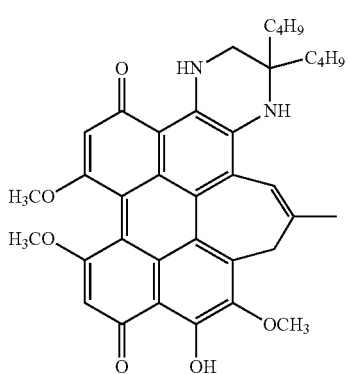

HC-104

Example 56

Preparation of dibutylpiperazino(hypocrellin B): the synthesis method similar to the preparation of dimethylpiperazino(hypocrellin B) in Example 52. Yield: 18.8%, Rf: 0.38. Characterization data of the product as follows: ESI MS: m/z, 665.8. Maximum UV absorption wavelength: 465 nm, 655 nm. The product is respectively represented by structural formula HC-105 or HC-106:

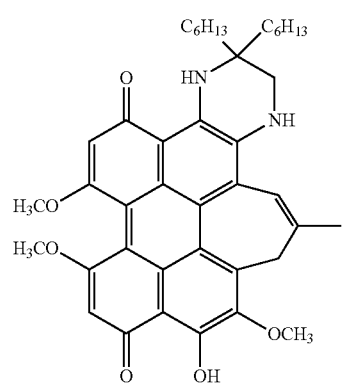

HC-105

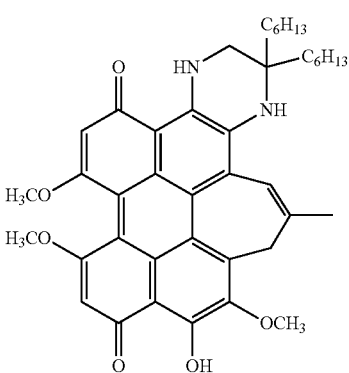

HC-106

Example 57

Preparation of trimethylpiperazino(hypocrellin B): the synthesis method similar to the preparation of dimethylpiperazino(hypocrellin B) in Example 52. Yield: 23.4%, Rf: 0.48. Characterization data of the product as follows: ESI MS: m/z, 569.3. Maximum UV absorption wavelength: 464 nm, 652 nm. The product is respectively represented by structural formula HC-107 or HC-108:

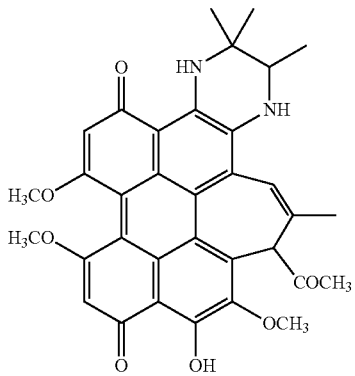

HC-107

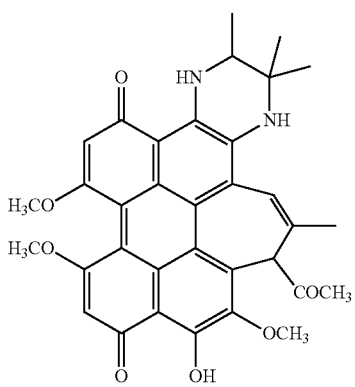

HC-108

Example 58

Preparation of dibutyl-methylpiperazino(hypocrellin B): the synthesis method similar to the preparation of dimethylpiperazino(hypocrellin B) in Example 52. Yield: 18.8%, Rf: 0.38. Characterization data of the product as follows: ESI MS: m/z, 596.8. Maximum UV absorption wavelength: 465 nm, 655 nm. The product is respectively represented by structural formula HC-109 or HC-110:

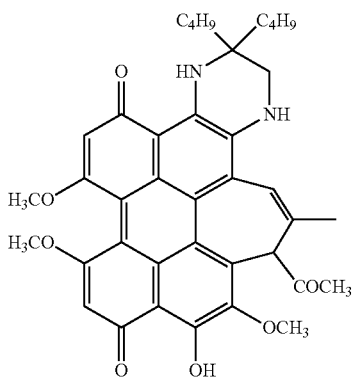

HC-109

-continued

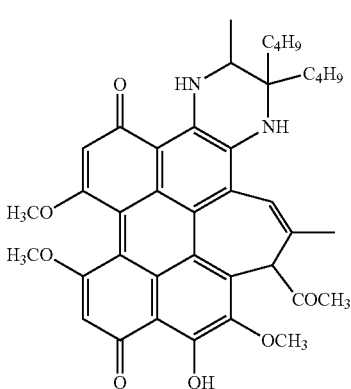

HC-110

Example 59

Preparation of dihexyl-methylpiperazino(hypocrellin B): the synthesis method similar to the preparation of dimethylpiperazino(hypocrellin B) in Example 52. Yield: 18.8%, Rf: 0.38. Characterization data of the product as follows: ESI MS: m/z, 596.8. Maximum UV absorption wavelength: 465 nm, 655 nm. The product is respectively represented by structural formula HC-111 or HC-112:

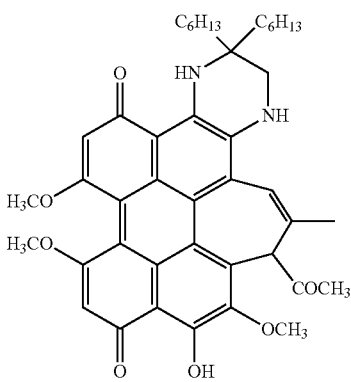

HC-111

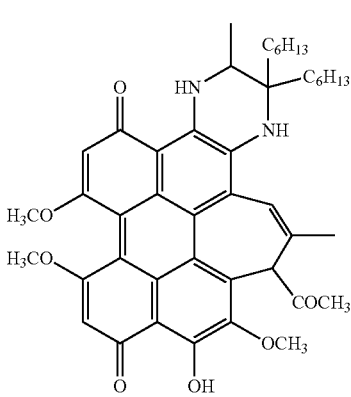

HC-112

Example 60

Preparation of dimethyl-ethoxylpiperazino(hypocrellin B): the synthesis method similar to the preparation of dimethylpiperazino (hypocrellin B) in Example 52. Yield: 12.5%, Rf: 0.35. Characterization data of the product as follows: ESI MS: m/z, 611.6. Maximum UV absorption wavelength: 463 nm, 652 nm. The product is respectively represented by structural formula HC-113 or HC-114:

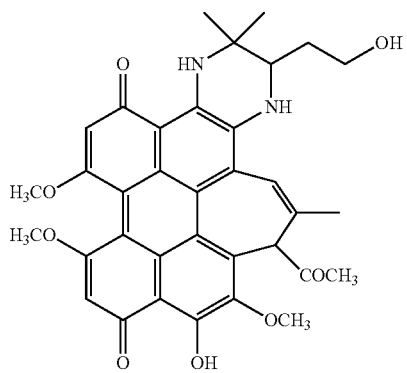

HB-113

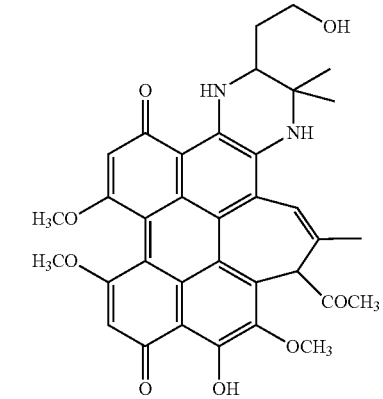

HB-114

Example 61

Preparation of dimethyl-DEG-ylpiperazino(hypocrellin B): the synthesis method similar to the preparation of dimethylpiperazino(hypocrellin B) in Example 52. Yield: 13.8%, Rf: 0.40. Characterization data of the product as follows: ESI MS: m/z, 655.6. Maximum UV absorption wavelength: 460 nm, 655 nm. The product is respectively represented by structural formula HC-115 or HC-116:

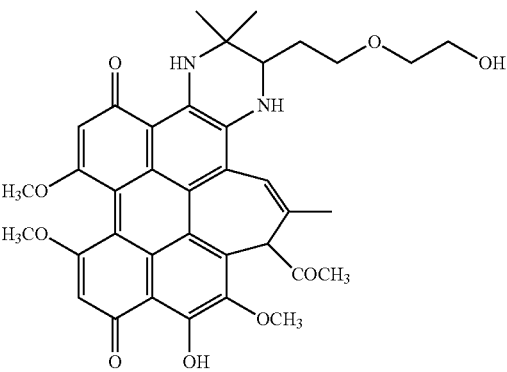

HB-115

HB-116

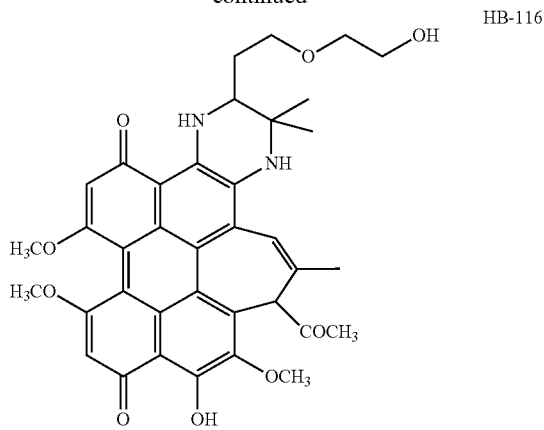

Example 62

Preparation of dimethyl-triethylene glycol-ylpiperazino (hypocrellin B): the synthesis method similar to the preparation of dimethylpiperazino(hypocrellin B) in Example 52. Yield: 8.5%, Rf: 0.45. Characterization data of the product as follows: ESI MS: m/z, 699.1. Maximum UV absorption wavelength: 462 nm, 658 nm. The product is respectively represented by structural formula HC-117 or HC-118:

HB-117

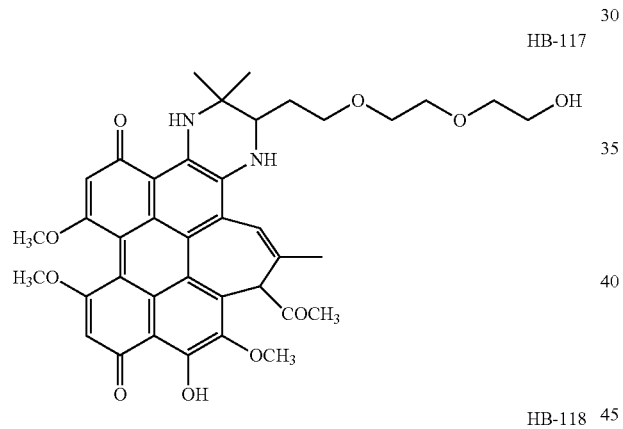

HB-118

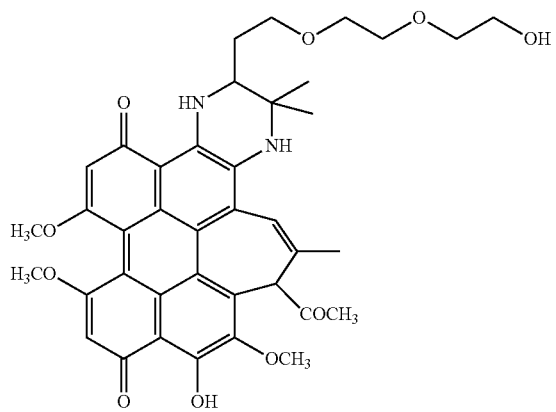

Example 63

Preparation of dimethyl-triethylene glycol-ylpiperazino (hypocrellin B): the synthesis method similar to the preparation of dimethylpiperazino(hypocrellin B) in Example 52. Yield: 8.5%, Rf: 0.45. Characterization data of the product as follows: ESI MS: m/z, 745.5. Maximum UV absorption wavelength: 462 nm, 658 nm. The product is respectively represented by structural formula HC-119 or HC-120:

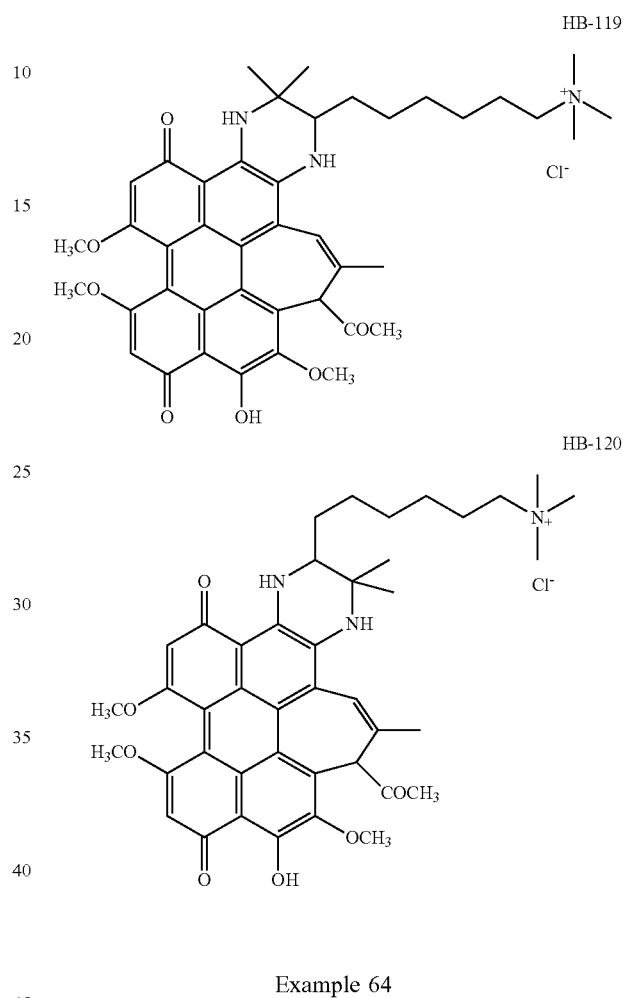

Example 64

Preparation of diethoxylpiperazino(hypocrellin B):

A hypocrellin B (HB) (100 mg, 0.18 mmol) and dihydroxyethyl ethyldiamine (421 mg, 2 mmol) were dissolved in 20 mL of anhydrous acetonitrile, fully mixed, heated to 45° C. under nitrogen protection, and stirred in dark for 6 h. On completion of the reaction, the solvent was removed by rotary evaporation. A blue black solid residue was dissolved in 100 mL of dichloromethane, washed with 50 mL of diluted aqueous hydrochloric acid solution thrice, and then washed with distilled water once. The organic layer was dried with anhydrous magnesium sulfate, and filtered, and then the organic phase was spin-dried to obtain a crude product. The resulting crude product was further separated by silica gel chromatography with acetone:ethyl acetate:ethanol:diethylamine (volume ratio: 20:1:1:1) as a developer to obtain a blue black solid product with a yield of 18.5% and with Rf of 0.21. Characterization data of the product as follows: ESI MS: m/z, 583.5. Maximum UV absorption wavelength: 463 nm, 650 nm. The product is respectively represented by structural formula HB-121 or HB-122:

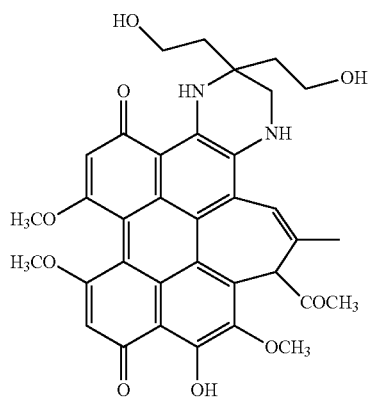

HB-121

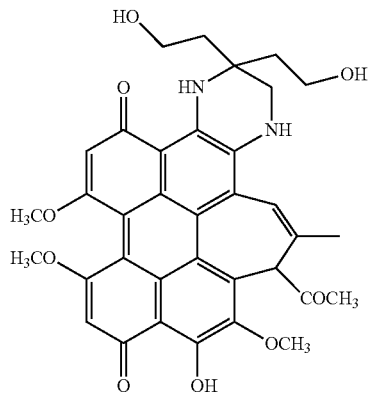

HB-122

Example 65

Preparation of dihexyl-ethoxylpiperazino(hypocrellin B): the synthesis method similar to the preparation of diethxoylpiperazino(hypocrellin B) in Example 64. Yield: 25.5%, Rf: 0.41. Characterization data of the product as follows: ESI MS: m/z, 596.8. Maximum UV absorption wavelength: 468 nm, 652 nm. The product is respectively represented by structural formula HB-123 or HB-124:

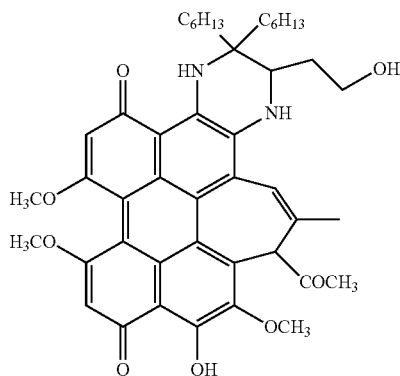

HB-123

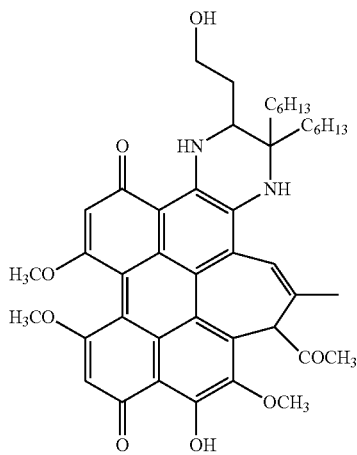

HB-124

Example 66

Preparation of a DABACO quaternary ammonium salt-modified hypocrellin B derivative: the synthesis method similar to the preparation of a quaternary ammonium salt-containing hypocrellin derivative in Example 46. 2,17-amino-substituted product HB-125: yield: 12.4%, Rf: 0.28, MS (ESI+) 941.2, maximum UV absorption wavelength: 455 nm, 635 nm. 2-amino-substituted product HB-126: yield: 16.5%, Rf: 0.48, MS (ESI+) 746.9. Maximum UV absorption wavelength: 451 nm, 624 nm. The amino-substituted products HB-125 and HB-126 have the structural formulas as shown in the figure:

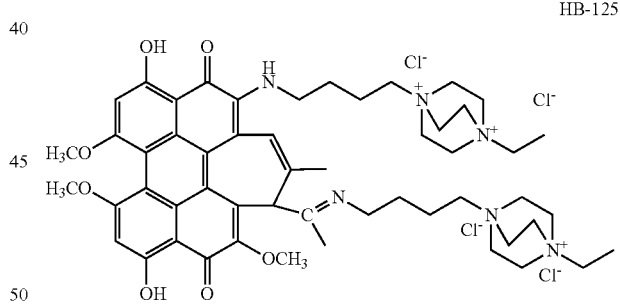

HB-125

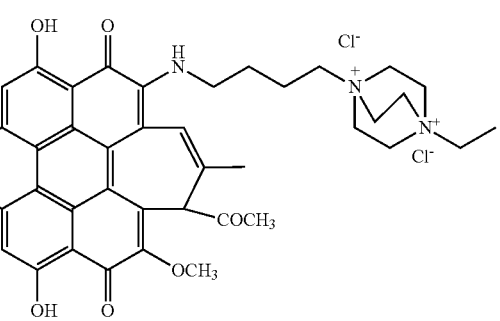

HB-126

Example 67

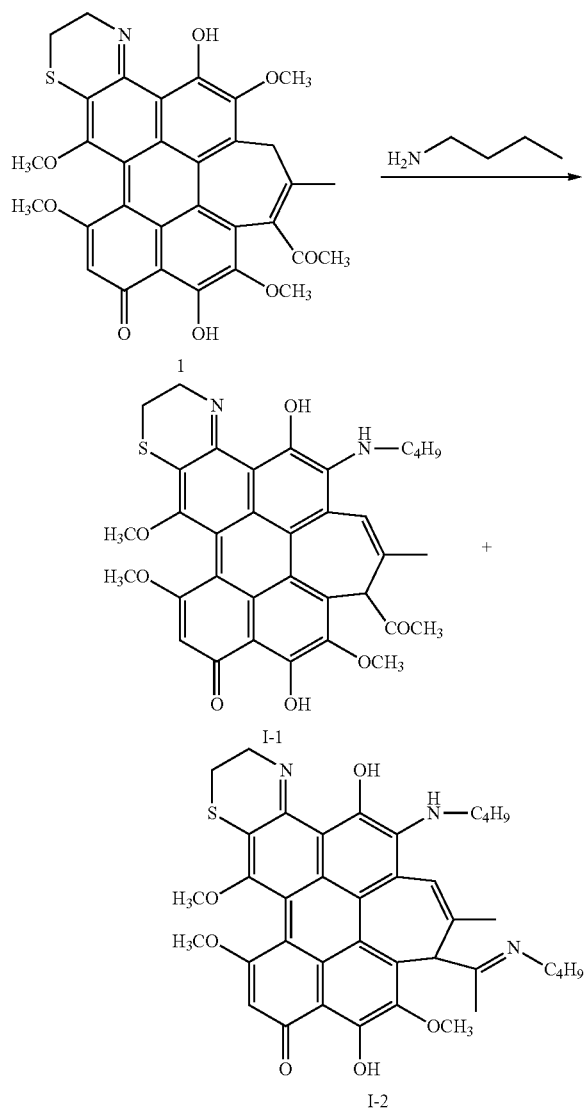

Please refer to the following documents for the preparation method of a compound 1:

Photoreactions of hypocrellin B with thiol compounds, *Journal of Photochemistry and Photobiology B: Biology*, 1998, 44, 45-52; Synthesis of a new water-soluble phototherapeutic sensitizer from hypocrellin B with enhanced red absorption, Synthesis of a new water-soluble phototherapeutic sensitizer, *Dyes and Pigments*, 1999, 4, 93-100. 10 groups of 5 mL of ethanol/water buffer solution (1/3, pH=10) of HB (0.2 mM) and mercaptoethylamine hydrochloride (0.01 mM) present in 10 photochemical reactors were irradiated with a 450 W high pressure sodium lamp (light below 470 nm filtered with a glass long pass filter) at room temperature for 20 min. On completion of the reaction, and after acidification with 10% hydrochloric acid, chloroform was added for extraction. The chloroform phase was washed with water and then spin-dried to obtain a crude product. The crude product was further separated by silica gel chromatography with chloroform:methanol (volume ratio: 99:1) as a developer to obtain a mixture of 4,5- substituted, 8,9-substituted or 4,5,8,9-substituted HB, which were separated by HPLC to obtain the compound 1 with a yield of 25.2%. MS (ESI+): m/z $C_{32}H_{27}NO_8S$, $[M+H]^+$ =586.1. 100 mg of the compound 1 and 10 mL of n-butylamine were dissolved in 100 mL of pyridine, fully mixed, heated to 50° C. under nitrogen protection, and stirred in dark for 10 h. On completion of the reaction, the solvent was removed by rotary evaporation. The solid residue was dissolved in 100 mL of chloroform, and washed with 50 mL of diluted aqueous hydrochloric acid solution several times until the solution was neutral. The organic phase was spin-dried to obtain a crude product. The resulting crude product was further separated by 1% $KH_2PO_4$ silica gel chromatography with petroleum ether:ethyl acetate:ethanol (volume ratio: 4:2.5:1) as a developer to respectively obtain products I-1 and I-2. I-1: yield: 40.4%; MS (ESI+), m/z $C_{35}H_{34}N_2O_7S$, $[M+H]^+$=527.2; maximum UV absorption wavelength: $\lambda_{max}$ (log ε), 682 nm (4.3). I-2: yield: 12.9%; MS (ESI+), m/z $C_{39}H_{43}N_3O_6S$, $[M+H]^+$=682.3; maximum UV absorption wavelength: $\lambda_{max}$ (log ε), 691 nm (4.2).

Figure 16:
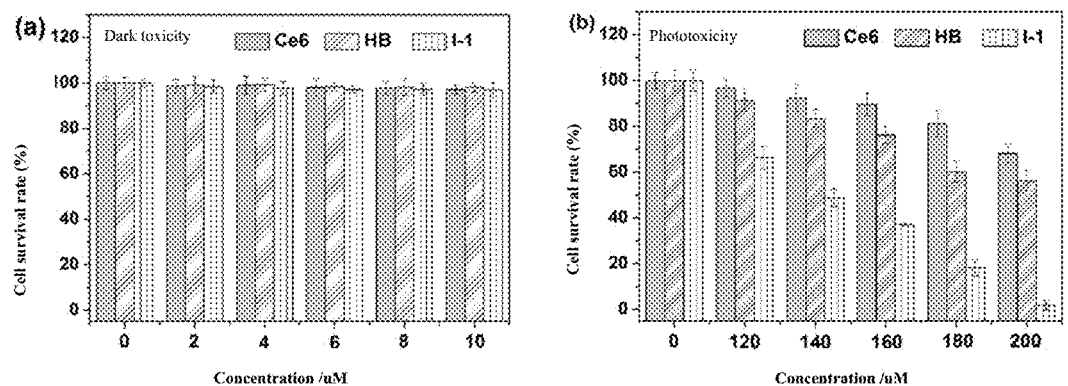
FIG. 16a shows the Hela cell dark toxicity of different concentrations of a dihydroporphin Ce6, hypocrellin B (HB) and a hypocrellin derivative I-1 or I-2 according to Example 67 of the invention.
FIG. 16b shows the Hela cell phototoxicity of different concentrations of a dihydroporphin Ce6, hypocrellin B (HB) and a hypocrellin derivative I-1 or I-2 according to Example 67 of the invention.
Figure 17:
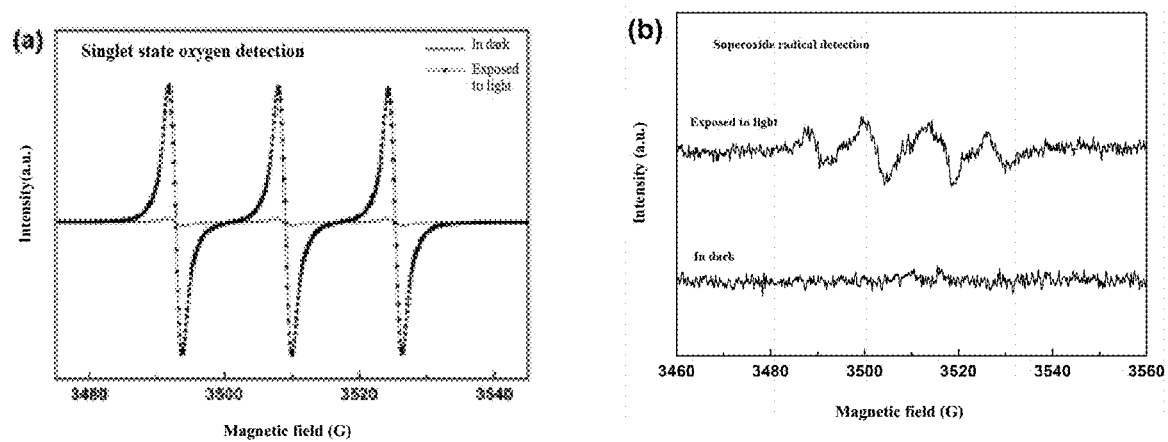
FIG. 17a shows the reaction of a hypocrellin derivative II-2 according to Example 67 of the invention with a singlet state oxygen scavenger.
FIG. 17b shows the reaction of a hypocrellin derivative II-2 according to Example 67 of the invention with a superoxide radical scavenger.

Dark toxicity experiment: Hela cells at a certain concentration were inoculated into a 96-well plate, and cultured for 12-24 h. After removing the original culture solution from the 96-well plate, compound I-1 solutions at different concentrations were added. After incubation for 1 h, the photosensitizer solution was removed, and a fresh culture solution was added for cultivation in a 5% $CO_2$ environment at 37° C. for 24 h. The survival rate of cells in each group was detected by MTT assay. As shown in FIG. 16a, the compound I-1 has very low cytotoxicity, which is equivalent to the cytotoxicity of the commercial photosensitizer dihydroporphin Ce6 and the HB.

Phototoxicity experiment: Hela cells were incubated together with different concentrations of the compound I-1, the HB and the Ce6 respectively, further incubated in an incubator with a 5% $CO_2$ environment at 37° C. for another 1 hour. After laser irradiation with a power density of 50 mW/cm² at a wavelength of 671 nm for 20 min, the Hela cells were further cultured and incubated in an incubator with a 5% $CO_2$ environment at 37° C. for another 24 h. The survival rate of cells in each group was detected by MTT assay. As shown in FIG. 16b, 200 nM compound I-1 can kill more than 90% Hela cells, while the commercial photosensitizer dihydroporphin Ce6 can kill only about 30% Hela cells under identical conditions.

Example 68

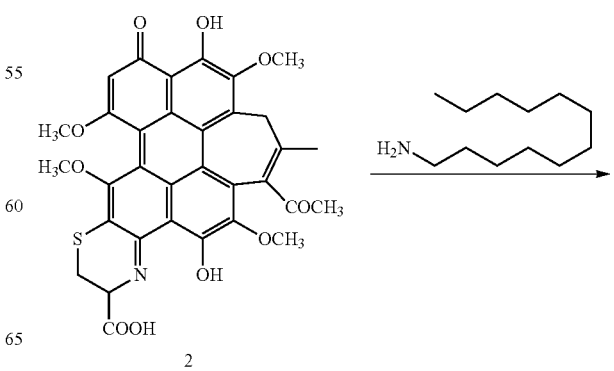

-continued

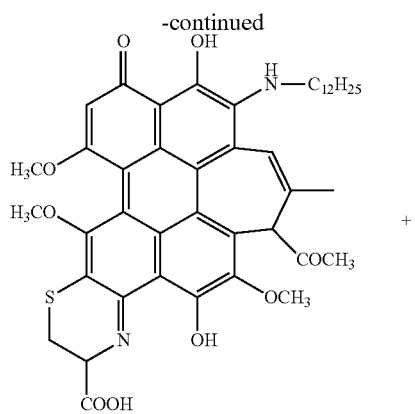

I-3

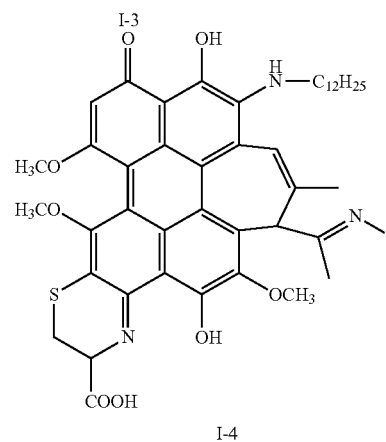

I-4

Please refer to the following documents for the preparation method of a compound 2: Photoreactions of hypocrellin B with thiol compounds, *Journal of Photochemistry and Photobiology B: Biology,* 1998, 44, 45-52; Synthesis of a new water-soluble phototherapeutic sensitizer, *Dyes and Pigments,* 1999, 4, 93-100. 10 groups of 5 mL of methanol/water buffer solution (1/3, pH=11) of HB (0.5 mM) and cysteine hydrochloride (0.05 mM) present in 10 photochemical reactors were irradiated with a 450 W high pressure sodium lamp (light below 470 nm filtered with a glass long pass filter) at room temperature for 20 min. On completion of the reaction, and after acidification with 10% hydrochloric acid, chloroform was added for extraction. The chloroform phase was washed with water and then spin-dried to obtain a crude product. The crude product was further separated by silica gel chromatography with chloroform:methanol (volume ratio: 98:1) as a developer to obtain a mixture of 4,5-substituted and 8,9-substituted HB, which were separated by HPLC to obtain the compound 2 with a yield of 24.5%. MS (ESI+): m/z $C_{33}H_{27}NO_{10}S$, $[M+H]^+$ =630.1. 100 mg of the compound 2 and 5 mL of n-dodecylamine were dissolved in 100 mL of pyridine, fully mixed, heated to 50° C. under nitrogen protection, and stirred in dark for 15 h. On completion of the reaction, the solvent was removed by rotary evaporation. The solid residue was dissolved in 100 mL of chloroform, and washed with 50 mL of diluted aqueous hydrochloric acid solution until the solution was neutral. The organic phase was spin-dried to obtain a crude product. The resulting crude product was further separated by 1.5% $KH_2PO_4$ silica gel chromatography with petroleum ether:ethyl acetate:ethanol (volume ratio: 4:2.5:1) as a developer to respectively obtain two products I-3 and I-4. I-3: yield: 20.4%; MS (ESI+), m/z $C_{44}H_{50}N_2O_9S$, $[M+H]^+$=783.3; maximum UV absorption wavelength: $\lambda_{max}$ (log ε), 680 nm (4.3). I-4: yield: 10.1%; MS (ESI+), m/z $C_{39}H_{43}N_3O_6S$, $[M+H]^+$=950.5; maximum UV absorption wavelength: $\lambda_{max}$ (log ε), 691 nm (4.2).

Example 69

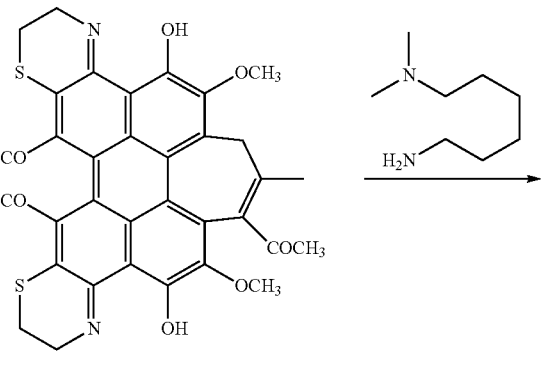

3

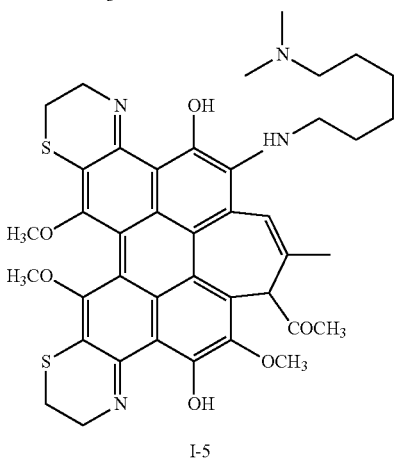

I-5

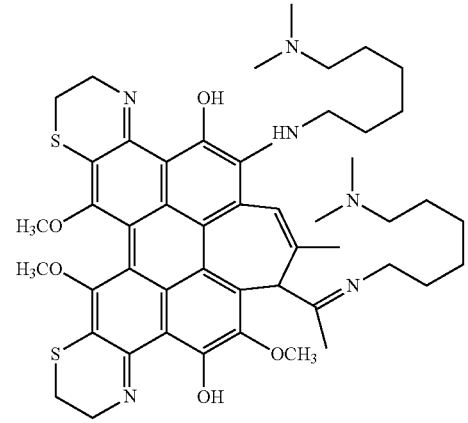

I-6

By referring to the method in Example 67, 10 groups of 5 mL of ethanol/water buffer solution (1/3, pH=11) of HB (0.5 mM) and mercaptoethylamine hydrochloride (0.1 mM) present in 10 photochemical reactors were irradiated with a 450 W high pressure sodium lamp (light below 470 nm filtered with a glass long pass filter) at room temperature for 30 min. On completion of the reaction, and after acidification with 10% hydrochloric acid, chloroform was added for extraction. The chloroform phase was washed with water and then spin-dried to obtain a crude product. The crude product was further separated by silica gel chromatography with chloroform:methanol (volume ratio: 99:1) as a developer to obtain a mixture of 4,5-substituted, 8,9-substituted or 4,5,8,9-substituted HB, which were separated by HPLC to obtain a compound 3 with a yield of 30.9%. MS (ESI+): m/z $C_{34}H_{30}N_2O_7S_2$, $[M+H]^+$=643.1. 100 mg of the compound 3 and 10 mL of 6-N,N-dimethylamino n-hexylamine were dissolved in 50 mL of tetrahydrofuran, fully mixed, heated to 55° C. under nitrogen protection, and stirred in dark for 18 h. On completion of the reaction, the solvent was removed by rotary evaporation. The solid residue was dissolved in 100 mL of chloroform, and washed with 50 mL of diluted aqueous hydrochloric acid solution several times until the solution was neutral. The organic phase was spin-dried to obtain a crude product. The resulting crude product was further separated by 2% $KH_2PO_4$ silica gel chromatography with petroleum ether:ethyl acetate:ethanol (volume ratio: 3:2:1) as a developer to respectively obtain two products I-5 and I-6. I-5: yield: 26.4%; MS (ESI+), m/z $C_{41}H_{46}N_4O_6S2$, $[M+H]^+$=755.3; maximum UV absorption wavelength: $\lambda_{max}$ (log ε), 712 nm (4.0). I-6: yield: 15.1%; MS (ESI+), m/z $C_{49}H_{64}N_6O_5S2$, $[M+H]^+$=881.4; maximum UV absorption wavelength: $\lambda_{max}$ (log ε), 720 nm (4.1).

Example 70

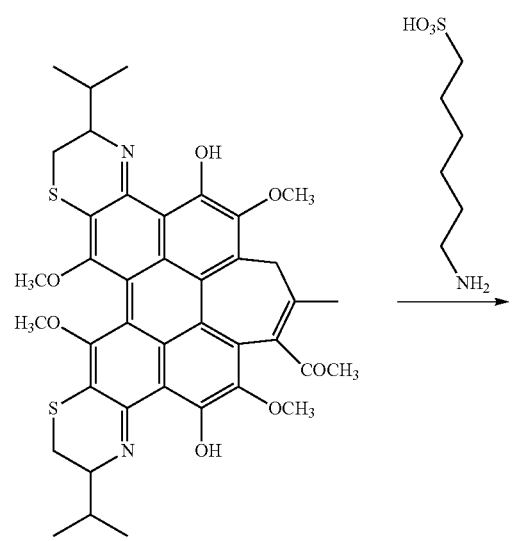

-continued

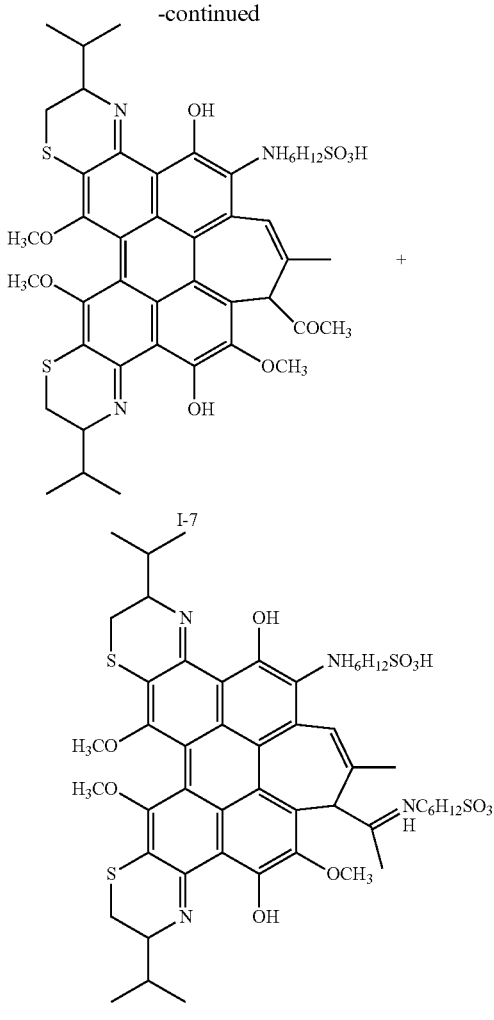

Please refer to the following documents for the preparation method of a compound 4: Photoreactions of hypocrellin B with thiol compounds, *Journal of Photochemistry and Photobiology B: Biology*, 1998, 44, 45-52; Synthesis of a new water-soluble phototherapeutic sensitizer, *Dyes and Pigments*, 1999, 4, 93-100. 10 groups of 4 mL of ethanol/water buffer solution (1/3, pH=11) of HB (0.5 mM) and mercaptoethylamine hydrochloride (0.05 mM) present in 10 photochemical reactors were irradiated with a 450 W high pressure sodium lamp (light below 470 nm filtered with a glass long pass filter) at room temperature for 20 min. On completion of the reaction, and after acidification with 10% hydrochloric acid, chloroform was added for extraction. The chloroform phase was washed with water and then spin-dried to obtain a crude product. The crude product was further separated by silica gel chromatography with chloroform: methanol (volume ratio: 99:1) as a developer to obtain a mixture of 4,5-substituted, 8,9-substituted or 4,5,8,9-substituted HB, which were separated by HPLC to obtain the compound 4 with a yield of 27.3%. MS (ESI+): m/z $C_{40}H_{42}N_2O_7S_2$, $[M+H]^+$=727.2.

100 mg of the compound 4 and 1 g of 6-sulfo n-hexylamine were dissolved in 80 mL of dimethyl sulfoxide and 2 mol/L water solution of sodium hydroxide (1:1), fully mixed, heated to 120° C. under nitrogen protection, and stirred in dark for 4 h. On completion of the reaction, the pH was adjusted to a neutral pH with diluted hydrochloric acid, and the solvent was removed by rotary evaporation. The resulting crude product was further separated by 1% KH$_2$PO$_4$ silica gel chromatography with dichloromethane:methanol (volume ratio: 5:1) as a developer to respectively obtain products I-7 and I-8. I-7: yield: 30.4%; MS (ESI+), m/z C$_{45}$H$_{53}$N$_3$O$_9$S$_3$, [M+H]$^+$=876.3; maximum UV absorption wavelength: λ$_{max}$ (log ε), 715 nm (4.4). I-8: yield: 8.8%; MS (ESI+), m/z C$_{51}$H$_{66}$N$_4$O$_{11}$S$_4$, [M+H]$^+$=1039.3; maximum UV absorption wavelength: λ$_{max}$ (log ε), 721 nm (4.2).

Example 71

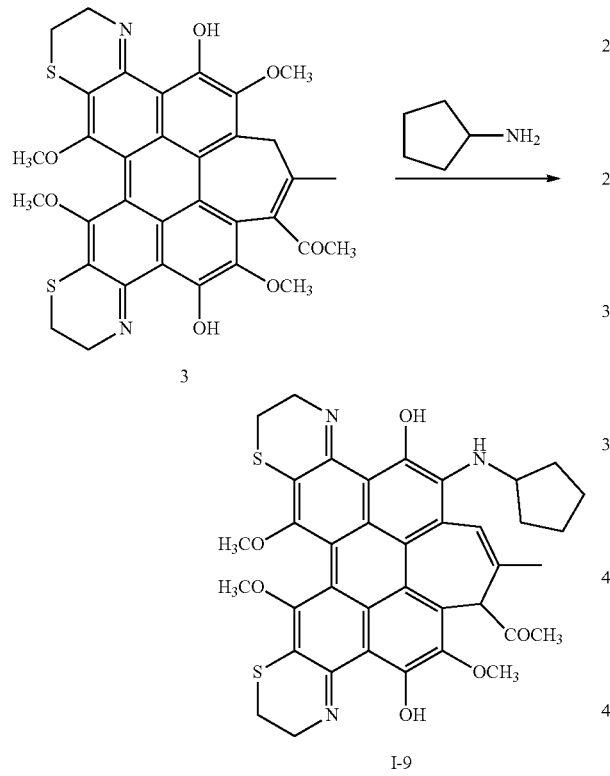

100 mg of the compound 3 and 10 mL of cyclopentylamine were dissolved in 100 mL of pyridine, fully mixed, heated to 50° C. under nitrogen protection, and stirred in dark for 15 h. On completion of the reaction, the solvent was removed by rotary evaporation. The solid residue was dissolved in 100 mL of chloroform, and washed with 50 mL of diluted aqueous hydrochloric acid solution several times until the solution was neutral. The organic phase was spin-dried to obtain a crude product. The resulting crude product was further separated by 1% KH$_2$PO$_4$ silica gel chromatography with petroleum ether:ethyl acetate:ethanol (volume ratio: 3:2:1) as a developer to obtain a compound I-9: yield: 46.4%; MS (ESI+), m/z C$_{38}$H$_{37}$N$_3$O$_6$S$_2$, [M+H]$^+$=696.2; maximum UV absorption wavelength: λ$_{max}$ (log ε), 710 nm (4.2).

Example 72

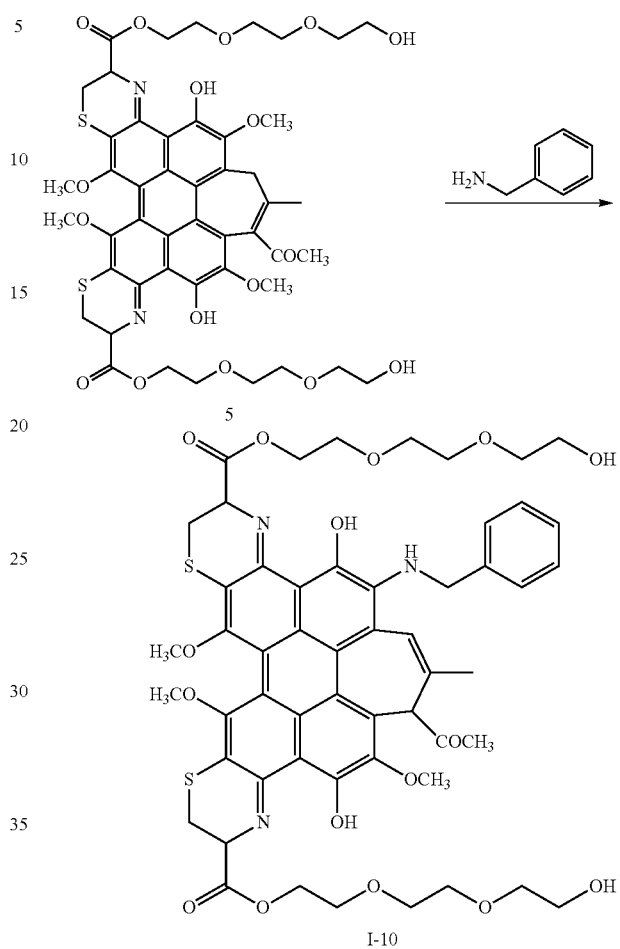

Please refer to the following documents for the preparation method of a compound 5: Photoreactions of hypocrellin B with thiol compounds, *Journal of Photochemistry and Photobiology B: Biology*, 1998, 44, 45-52; Synthesis of a new water-soluble phototherapeutic sensitizer, *Dyes and Pigments*, 1999, 4, 93-100. 10 groups of 5 mL of ethanol/water buffer solution (1/3, pH=10) of HB (0.5 mM) and cysteine triethylene glycol ester (0.05 mM) present in 10 photochemical reactors were irradiated with a 450 W high pressure sodium lamp (light below 470 nm filtered with a glass long pass filter) at room temperature for 10 min. On completion of the reaction, and after acidification with 10% hydrochloric acid, the crude product was further separated by silica gel chromatography with chloroform:methanol (volume ratio: 99:1) as a developer to obtain the compound 1 with a yield of 31.6%. MS (ESI+): m/z C$_{48}$H$_{54}$N$_2$O$_{17}$S$_2$, [M+H]$^+$=995.3.

100 mg of the compound 5 and 10 mL of benzylamine were dissolved in 100 mL of pyridine, fully mixed, heated to 55° C. under nitrogen protection, and stirred in dark for 12 h. On completion of the reaction, the solvent was removed by rotary evaporation. The solid residue was dissolved in 100 mL of chloroform, adjusted with diluted hydrochloric acid until the solution was at a neutral pH, and spin-dried to obtain a crude product. The resulting crude product was further separated by 1.5% KH$_2$PO$_4$ silica gel chromatography with petroleum ether:ethyl acetate:ethanol (volume ratio: 3:2:1) as a developer to obtain a compound I-10: yield: 38.6%; MS (ESI+), m/z $C_{54}H_{59}N_3O_{16}S_2$, $[M+H]^+=1070.3$; maximum UV absorption wavelength: $\lambda_{max}$ (log 6), 713 nm (4.2).

Example 73

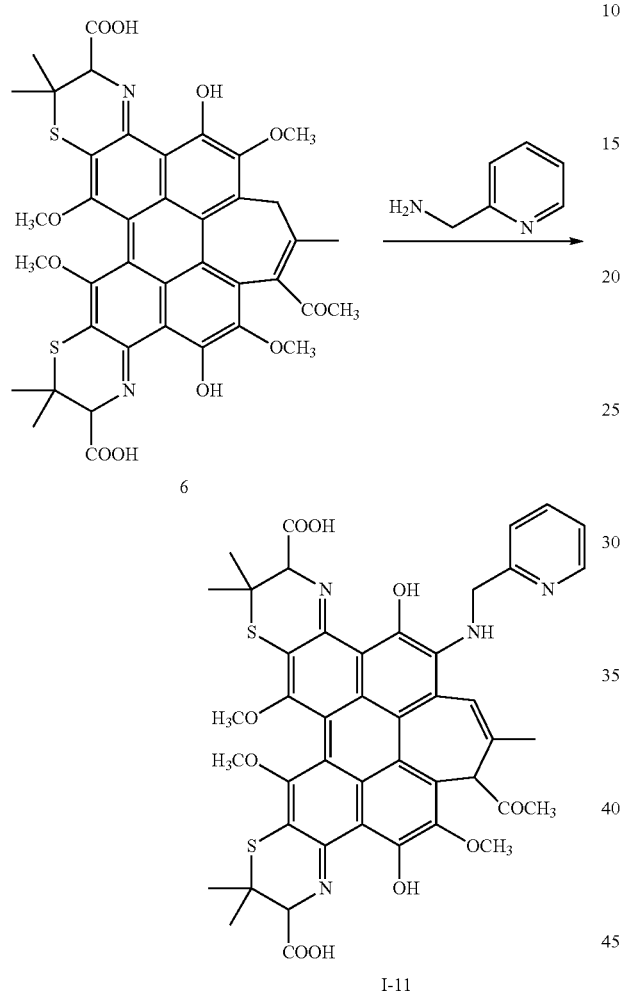

Please refer to the following documents for the preparation method of a compound 6: Photoreactions of hypocrellin B with thiol compounds, *Journal of Photochemistry and Photobiology B: Biology,* 1998, 44, 45-52; Synthesis of a new water-soluble phototherapeutic sensitizer, *Dyes and Pigments,* 1999, 4, 93-100. 10 groups of 5 mL of methanol/water buffer solution (1/3, pH=11) of HB (0.5 mM) and 2-dimethyl cysteine (0.1 mM) present in 10 photochemical reactors were irradiated with a 450 W high pressure sodium lamp (light below 470 nm filtered with a glass long pass filter) at room temperature for 30 min. On completion of the reaction, and after acidification with 10% hydrochloric acid, a crude product was obtained by washing with chloroform and spin drying of the water phase, and then the compound 6 was obtained by Sephadex G-15 column chromatography with water as an eluting agent: yield: 40.2%. MS (ESI+): m/z $C_{40}H_{38}N_2O_{11}S_2$, $[M+H]^+=787.2$.

100 mg of the compound 6 and 10 mL of 2-methylamino pyridine were dissolved in 100 mL of pyridine, fully mixed, heated to 60° C. under nitrogen protection, and stirred in dark for 10 h. On completion of the reaction, the solvent was removed by rotary evaporation. The solid residue was dissolved in 100 mL of chloroform, adjusted with diluted hydrochloric acid until the solution was at a neutral pH, and spin-dried to obtain a crude product. The resulting crude product was further separated by 1.5% $KH_2PO_4$ silica gel chromatography with petroleum ether:ethyl acetate:ethanol (volume ratio: 3:2:1) as a developer to obtain a compound I-11: yield: 33.9%; MS (ESI+), m/z $C_{45}H_{42}N_4O_{10}S_2$, $[M+H]^+=863.2$; maximum UV absorption wavelength: $\lambda_{max}$ (log ε), 709 nm (4.2).

Example 74

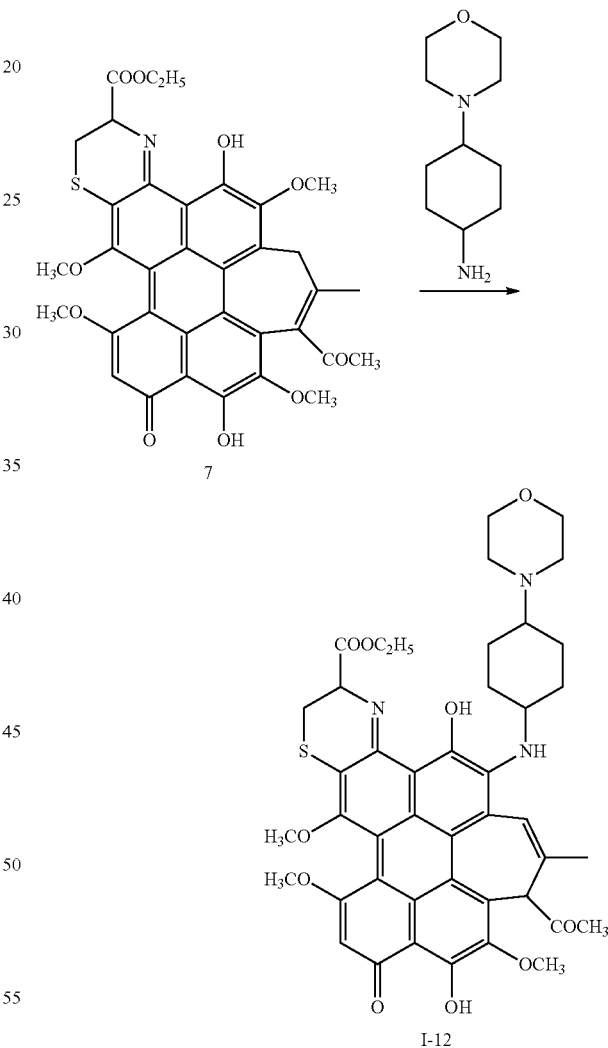

Please refer to the following documents for the preparation method of a compound 7: Photoreactions of hypocrellin B with thiol compounds, *Journal of Photochemistry and Photobiology B: Biology,* 1998, 44, 45-52; Synthesis of a new water-soluble phototherapeutic sensitizer, *Dyes and Pigments,* 1999, 4, 93-100. 10 groups of 5 mL of ethanol/water buffer solution (1/3, pH=10) of HB (0.2 mM) and cysteine ethyl ester (0.01 mM) present in 10 photochemical reactors were irradiated with a 450 W high pressure sodium lamp (light below 470 nm filtered with a glass long pass filter) at room temperature for 20 min. On completion of the reaction, and after acidification with 10% hydrochloric acid, chloroform was added for extraction. The chloroform phase was washed with water and then spin-dried to obtain a crude product. The crude product was further separated by silica gel chromatography with chloroform:methanol (volume ratio: 99:1) as a developer to obtain a mixture of 4,5-substituted, 8,9-substituted or 4,5,8,9-substituted HB, which were separated by HPLC to obtain the compound 7 with a yield of 24.5%. MS (ESI+): m/z $C_{35}H_{31}NO_{10}S$, $[M+H]^+$= 658.2.

100 mg of the compound 7 and 10 mL of 4-morpholin-cyclohexylamine were dissolved in 100 mL of pyridine, fully mixed, heated to 50° C. under nitrogen protection, and stirred in dark for 10 h. On completion of the reaction, the solvent was removed by rotary evaporation. The solid residue was dissolved in 100 mL of chloroform, and washed with 50 mL of diluted aqueous hydrochloric acid solution several times until the solution was neutral. The organic phase was spin-dried to obtain a crude product. The resulting crude product was further separated by 1% $KH_2PO_4$ silica gel chromatography with petroleum ether:ethyl acetate:ethanol (volume ratio: 3:2:1) as a developer to obtain a compound I-12: yield: 30.8%; MS (ESI+), m/z $C_{44}H_{47}N_3O_{10}S_2$, $[M+H]^+$=810.3; maximum UV absorption wavelength: λmax (log ε), 685 nm (4.2).

Example 75

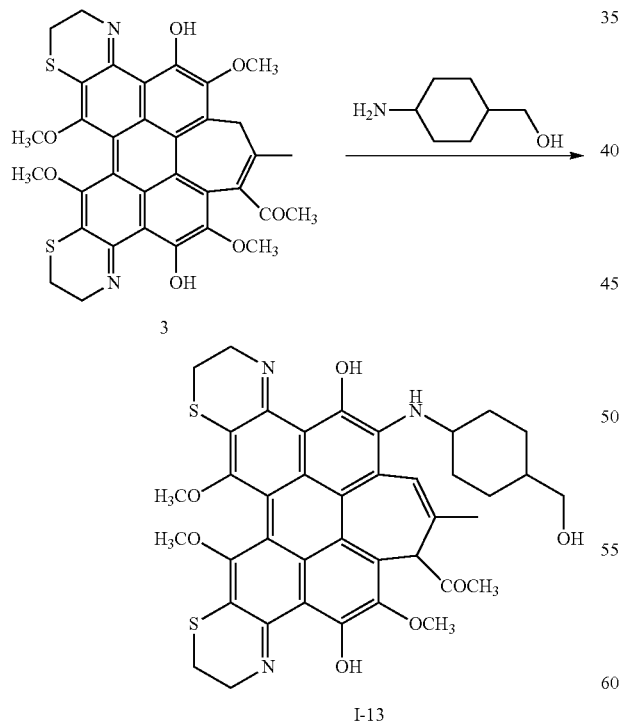

I-13

Please refer to Example 71 for the synthesis of a compound I-13: yield: 46.4%; MS (ESI+), m/z $C_{40}H_{41}N_3O_7S_2$, $[M+H]^+$=740.2; maximum UV absorption wavelength: $\lambda_{max}$ (log ε), 710 nm (4.1).

Example 76

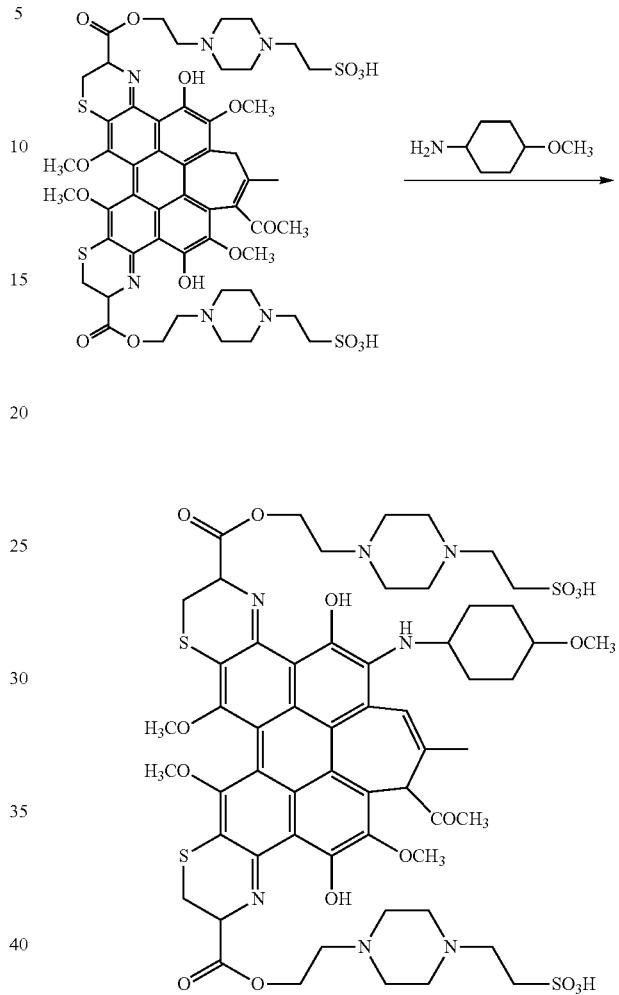

Please refer to Example 72 for the synthesis of a compound I-14: yield: 26.6%; MS (ESI+), m/z $C_{58}H_{73}N_7O_{17}S_4$, $[M+H]^+$=1268.4; maximum UV absorption wavelength: $\lambda_{max}$ (log ε), 712 nm (4.0).

Example 77

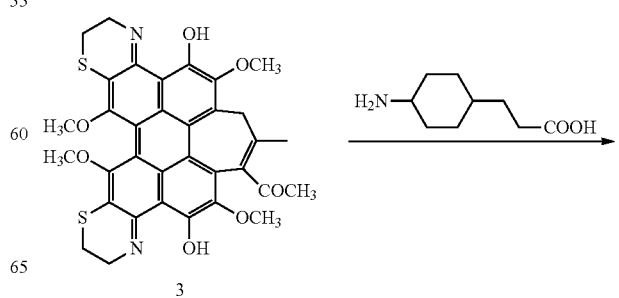

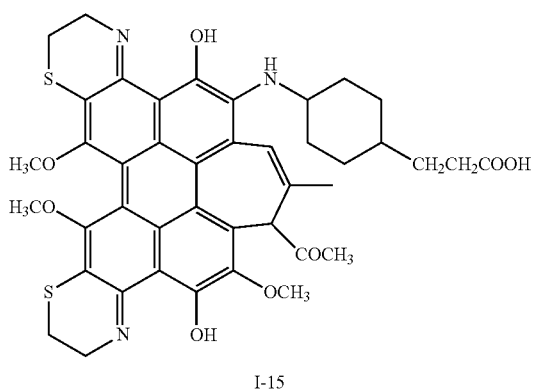

I-15

Please refer to Example 71 for the synthesis of a compound I-15: yield: 35.6%; MS (ESI+), m/z $C_{42}H_{43}N_3O_8S_2$, $[M+H]^+=782.2$; maximum UV absorption wavelength: $\lambda_{max}$ (log ε), 710 nm (4.1).

Example 78

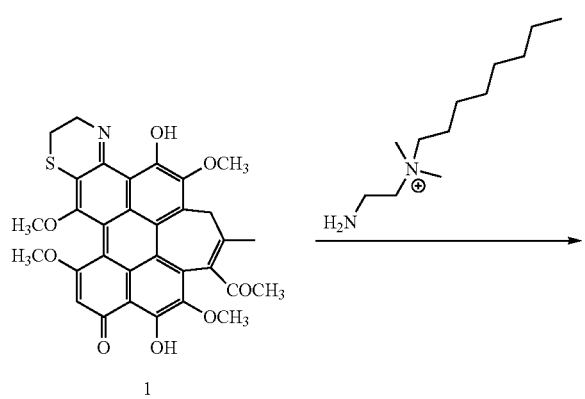

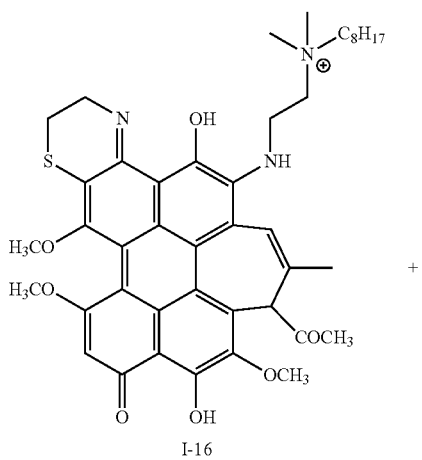

I-16

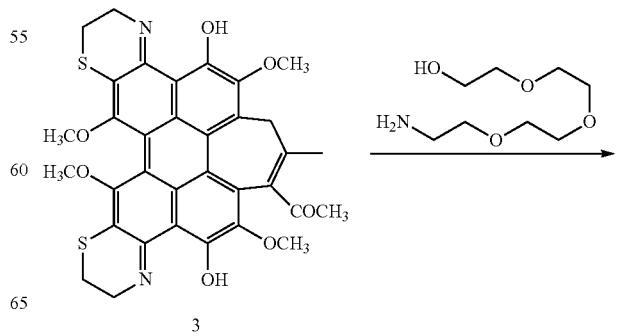

I-17

100 mg of the compound 1 and 200 mg of a long chain quaternary ammonium salt derivative were dissolved in 20 mL of anhydrous acetonitrile, fully mixed, heated to 50° C. under nitrogen protection, and stirred in dark for 10 h. On completion of the reaction, the solvent was removed by rotary evaporation. The solid residue was dissolved in 200 mL of dichloromethane, washed with 50 mL of diluted aqueous hydrochloric acid solution until the solution was neutral, and spin-dried to obtain a crude product. The resulting crude product was further separated by silica gel chromatography with acetone:ethylacetate:ethanol:diethylamine (volume ratio: 20:1:1:3) as a developer to respectively obtain two products I-16 and I-17. I-16: yield: 16.4%; MS (ESI+), m/z $C_{43}H_{52}N_3O_7S$, $[M+H]^+=754.4$; maximum UV absorption wavelength: $\lambda_{max}$ (log ε), 681 nm (4.2). I-17: yield: 11.2%; MS (ESI+), m/z $C_{55}H_{79}N_5O_6S$, $[M+H]^+=468.8$; maximum UV absorption wavelength: $\lambda_{max}$ (log ε), 692 nm (4.3).

Example 79

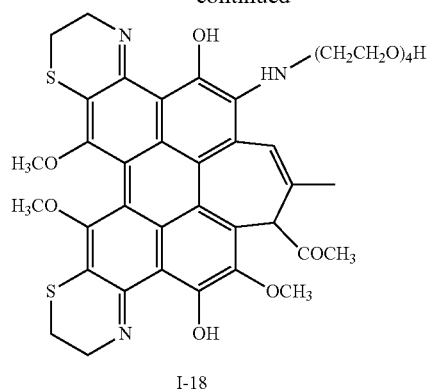

I-18

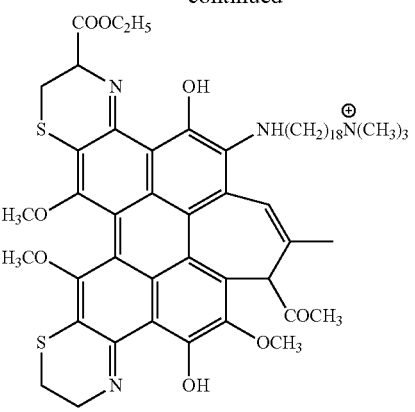

I-20

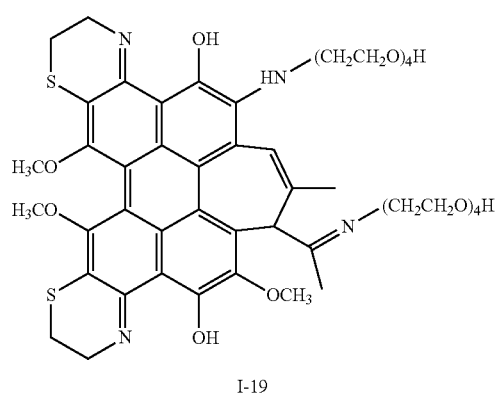

I-19

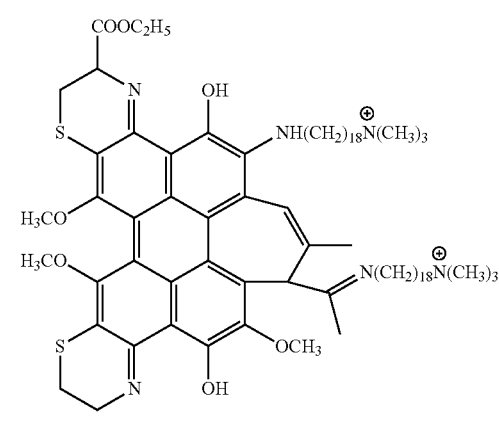

I-21

Please refer to Example 78 for the synthesis of compounds I-18 and I-19. I-18: yield: 12.4%; MS (ESI+), m/z $C_{41}H_{45}N_3O_{10}S_2$, $[M+H]^+=804.2$; maximum UV absorption wavelength: $\lambda_{max}$ (log ε), 712 nm (4.0). I-19: yield: 8.1%; MS (ESI+), m/z $C_{49}H_{62}N_4O_{13}S_2$, $[M+H]^+=979.4$; maximum UV absorption wavelength: $\lambda_{max}$ (log ε), 718 nm (4.1).

Example 80

The synthesis of compounds I-20 and I-21 is identical to Example 68. I-20: yield: 16.4%; MS (ESI+), m/z $C_{43}H_{52}N_3O_7S$, $[M]^+=952.5$; maximum UV absorption wavelength: $\lambda_{max}$ (log ε), 681 nm (4.2). I-21: yield: 11.2%; MS (ESI+), m/z $C_{76}H_{119}N_5O_8S$, $[M/2]^{2+}=630.9$; maximum UV absorption wavelength: $\lambda_{max}$ (log ε), 691 nm (4.1).

Example 81

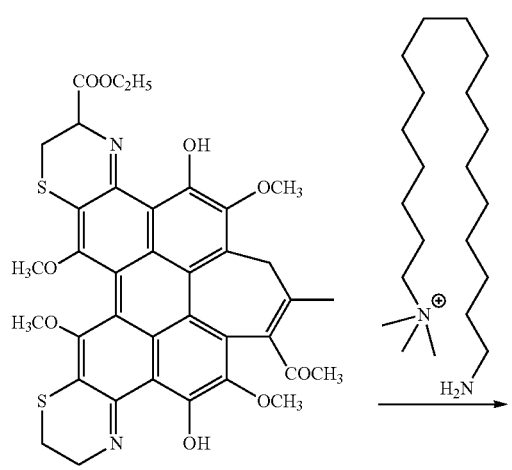

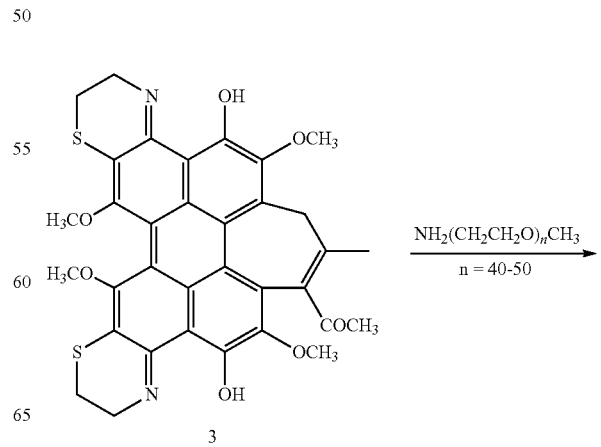

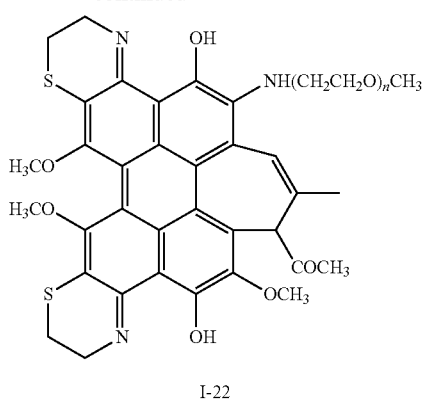

I-22

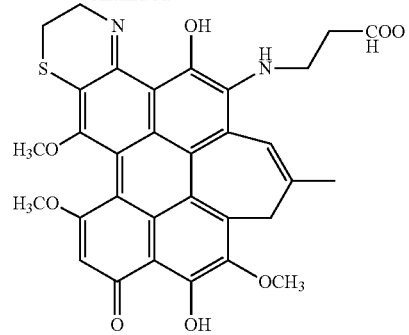

I-24

100 mg of the compound 3 and 400 mg of amino-PEG 2000 were dissolved in 20 mL of dichloromethane, fully mixed, and stirred in dark at room temperature under nitrogen protection for 20 h. On completion of the reaction, diethyl ether was added to separate out a solid, i.e., a crude product. The resulting crude product was further separated by silica gel chromatography to obtain a compound I-22: yield: 16.4%; MS (ESI+), m/z $C_{33}H_{27}N_2O_6S_2$, [M+H]$^+$= 612.1; maximum UV absorption wavelength: $\lambda_{max}$ (log ε), 681 nm (4.0).

Example 82

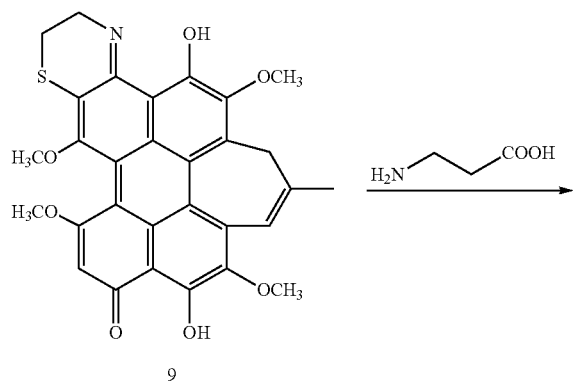

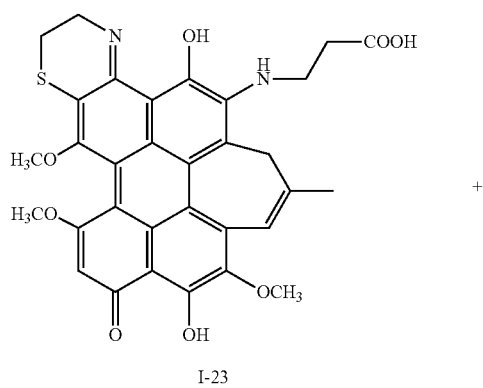

I-23

Please refer to the following documents for the preparation method of a compound 9: Photoreactions of hypocrellin B with thiol compounds, *Journal of Photochemistry and Photobiology B: Biology*, 1998, 44, 45-52; Synthesis of a new water-soluble phototherapeutic sensitizer, *Dyes and Pigments*, 1999, 4, 93-100. 10 groups of 5 mL of ethanol/water buffer solution (1/3, pH=10) of deacetylated hypocrellin HC (0.2 mM) and mercaptoethylamine hydrochloride (0.01 mM) present in 10 photochemical reactors were irradiated with a 450 W high pressure sodium lamp (light below 470 nm filtered with a glass long pass filter) at room temperature for 10 min. On completion of the reaction, and after acidification with 10% hydrochloric acid, chloroform was added for extraction. The chloroform phase was washed with water and then spin-dried to obtain a crude product. The crude product was further separated by silica gel chromatography with chloroform:methanol (volume ratio: 99:1) as a developer to obtain a mixture of 4,5-substituted, 8,9-substituted or 4,5,8,9-substituted HB, which were separated by HPLC to obtain the compound 9 with a yield of 22.4%. MS (ESI+): m/z $C_{30}H_{25}NO_7S$, [M+H]$^+$=544.1.

100 mg of the compound 9 and 10 mL of glycine were dissolved in 20 mL of pyridine, fully mixed, heated to 50° C. under nitrogen protection, and stirred in dark for 10 h. On completion of the reaction, the solvent was removed by rotary evaporation. After adding deionized water and washing with ethyl acetate, the water phase was spin-dried to obtain a crude product. The resulting crude product was further separated by 1% $KH_2PO_4$ silica gel chromatography with petroleum ether:ethyl acetate:ethanol (volume ratio: 3:2:1) as a developer to respectively obtain two products I-23 and I-24. I-23 and I-24: yield: 15.1%; MS (ESI+), m/z $C_{32}H_{28}N_2O_8S$, [M+H]$^+$=600.1; maximum UV absorption wavelength: $\lambda_{max}$ (log ε), 680 nm (4.0).

Example 83
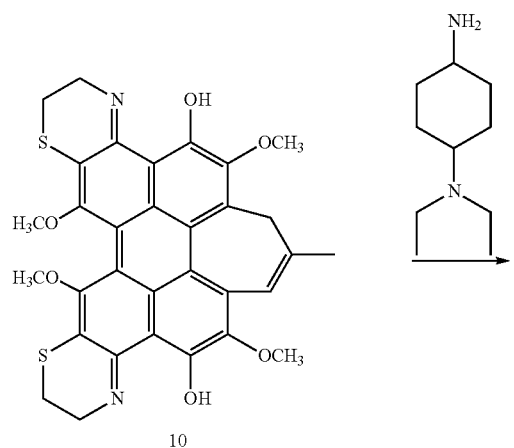
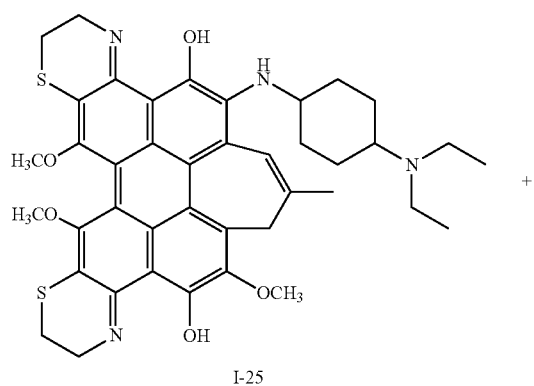
Example 84
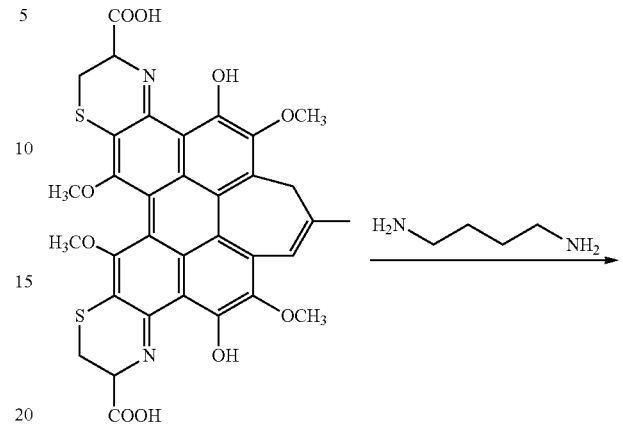
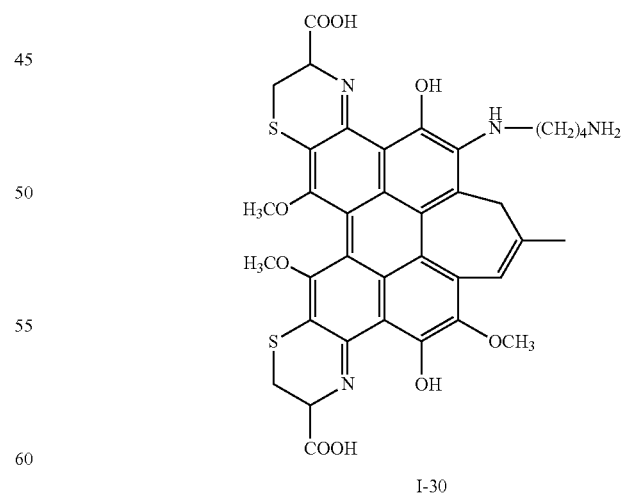
Please refer to Example 82 for the synthesis of compounds I-25 and I-26. I-25 and I-26: yield: 11.4%; MS (ESI+), m/z $C_{41}H_{46}N_4O_5S_2$, $[M+H]^+=739.3$; maximum UV absorption wavelength: $\lambda_{max}$ (log ε), 710 nm (4.0).
Please refer to Example 72 for the synthesis of compounds I-27 and I-28. I-27 and I-28: yield: 9.4%; MS (ESI+), m/z $C_{37}H_{36}N_4O_9S_2$, $[M+H]^+=745.2$; maximum UV absorption wavelength: $\lambda_{max}$ (log ε), 711 nm (4.0).

Example 85

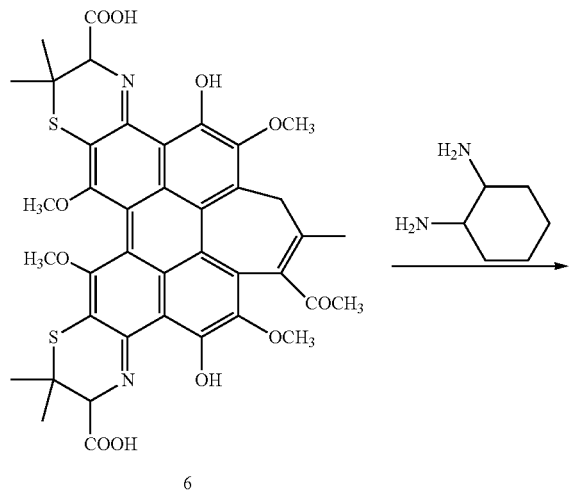

6

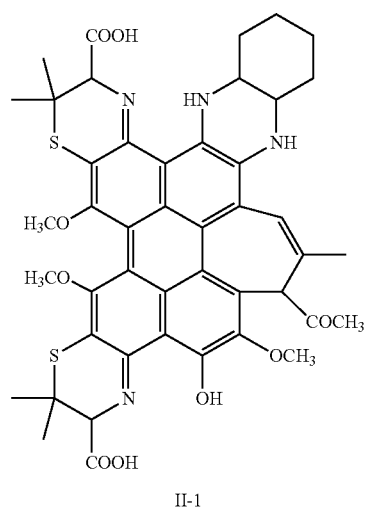

II-1

200 mg of the compound 12 was dissolved in 100 mL of freshly distilled tetrahydrofuran, and then 10 mL of cyclohexanediamine was added. The resulting solution was stirred in dark, and kept at 60° C. for 18 h. On termination of the reaction, the solvent was removed under reduced pressure, dissolved in chloroform, and washed with diluted hydrochloric acid until neutral. The organic phase was spin-dried to obtain a crude product, which was further separated by 1% $KH_2PO_4$ silica gel chromatography with petroleum ether:ethyl acetate:ethanol (volume ratio: 2:2:1) as a developer to obtain a compound I-1: yield: 18.5%; MS (ESI+), m/z $C_{45}H_{46}N_4O_9S_2$, $[M+H]^+=851.3$; maximum UV absorption wavelength: $\lambda_{max}$ (log ε), 735 nm (4.4).

Example 86

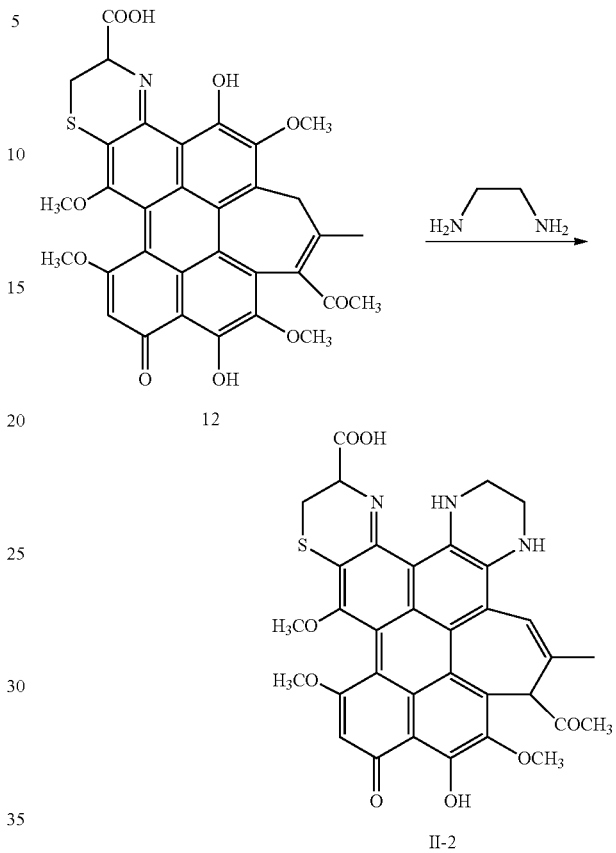

12

II-2

Please refer to Example 67 for the synthesis of a compound 12. 200 mg of the compound 12 was dissolved in 100 mL of freshly distilled tetrahydrofuran, and then 40 mL of hexanediamine was added. The resulting solution was stirred in dark, and kept at 55° C. for 12 h. On termination of the reaction, the solvent was removed under reduced pressure, dissolved in chloroform, and washed with diluted hydrochloric acid until neutral. The organic phase was spin-dried to obtain a crude product, which was further separated by 1% $KH_3PO_4$ silica gel chromatography with petroleum ether:ethyl acetate:ethanol (volume ratio: 2:2:1) as a developer to obtain a compound I-2: yield: 50.3%; MS (ESI+), m/z $C_{34}H_{29}N_3O_8S$, $[M+H]^+=640.2$; maximum UV absorption wavelength: $\lambda_{max}$ (log ε), 710 nm (4.4).

Figure 18:
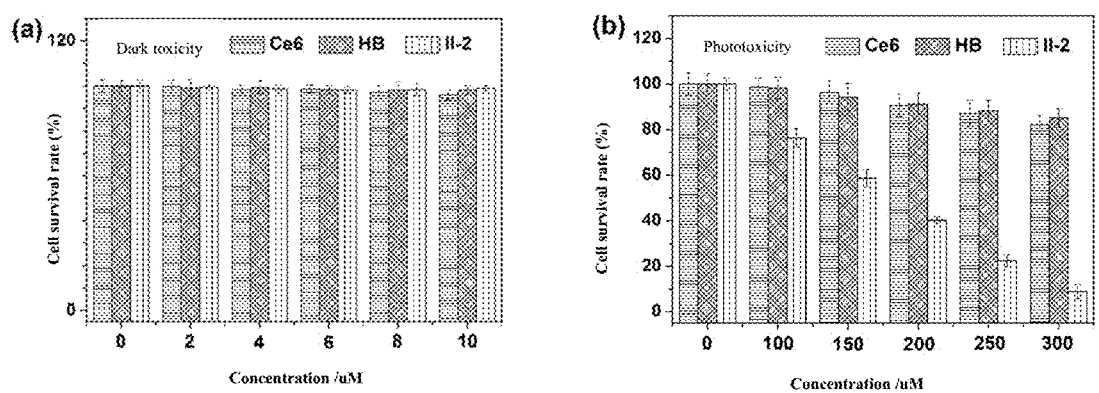
FIG. 18a shows the Hela cell dark toxicity of different concentrations of a dihydroporphin Ce6, hypocrellin B (HB) and a hypocrellin derivative II-2 according to Example 86 of the invention.
FIG. 18b shows the Hela cell phototoxicity of different concentrations of a dihydroporphin Ce6, hypocrellin B (HB) and a hypocrellin derivative II-2 according to Example 86 of the invention.

Dark toxicity experiment: Hela cells at a certain concentration were inoculated into a 96-well plate, and cultured for 12-24 h. After removing the original culture solution from the 96-well plate, compound II-2 solutions at different concentrations were added. After incubation for 1 h, the photosensitizer solution was removed, and a fresh culture solution was added for cultivation in a 5% $CO_2$ environment at 37° C. for 24 h. The survival rate of cells in each group was detected by MTT assay. As shown in FIG. 18a, the compound II-2 has very low cytotoxicity, which is equivalent to the cytotoxicity of the commercial photosensitizer dihydroporphin Ce6 and the HB. Phototoxicity experiment: Hela cells were incubated together with different concentrations of the compound II-2, the HB and the Ce6 respectively, further incubated in an incubator with a 5% $CO_2$ environment at 37° C. for another 1 hour. After laser irradiation with a power density of 20 mW/cm² at a wavelength of 808 nm for 20 min, the Hela cells were further cultured and incubated in an incubator with a 5% $CO_2$ environment at 37° C. for another 24 h. The survival rate of cells in each group was detected by MTT assay. As shown in FIG. 18b, 300 nM compound I-1 can kill more than 85% Hela cells, while the commercial photosensitizer Ce6 can kill only about 20% Hela cells under identical conditions.

Example 87

Please refer to Example 67 for the synthesis of a compound 13. Please refer to Example 86 for the synthesis of compounds II-3 and II-4. II-3: yield: 19.9%; MS (ESI+), m/z $C_{37}H_{35}N_3O_8S$, [M+H]$^+$=682.2; maximum UV absorption wavelength: $\lambda_{max}$ (log ε), 711 nm (4.3). II-4: yield: 18.6%; MS (ESI+), m/z $C_{37}H_{35}N_3O_8S$, [M+H]$^+$=682.2; maximum UV absorption wavelength: $\lambda_{max}$ (log ε), 711 nm (4.3).

Example 88

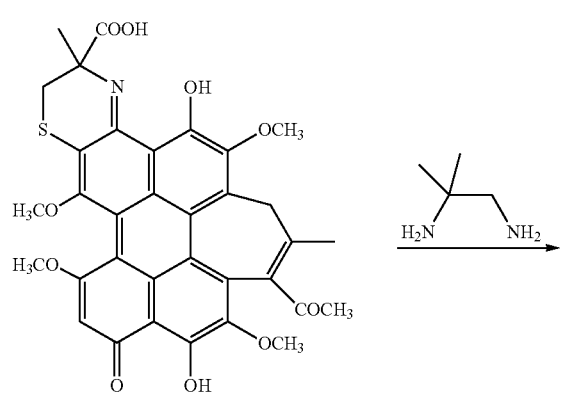

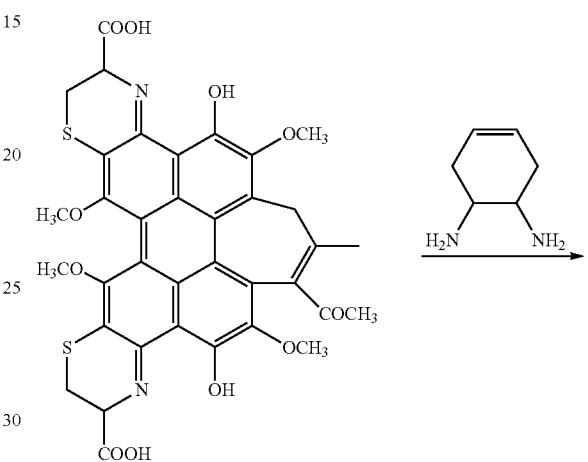

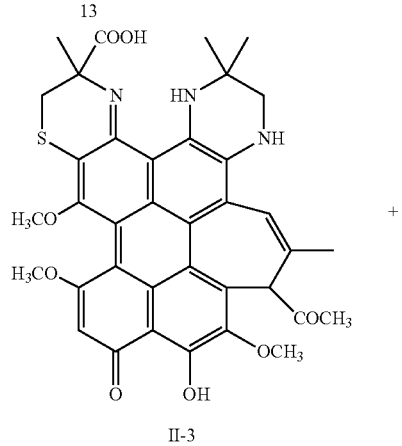

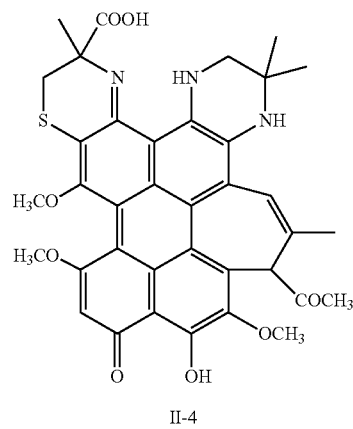

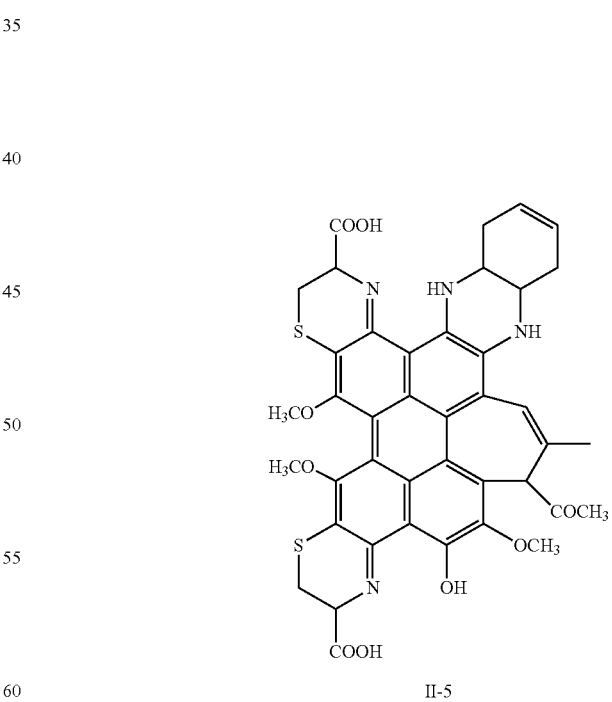

Please refer to Example 69 for the synthesis of a compound 14. Please refer to Example 85 for the synthesis of a compound II-5: yield: 15.2%; MS (ESI+), m/z $C_{41}H_{36}N_4O_9S_2$, [M+H]$^+$=793.2; maximum UV absorption wavelength: $\lambda_{max}$ (log ε), 730 nm (4.4).

Example 89

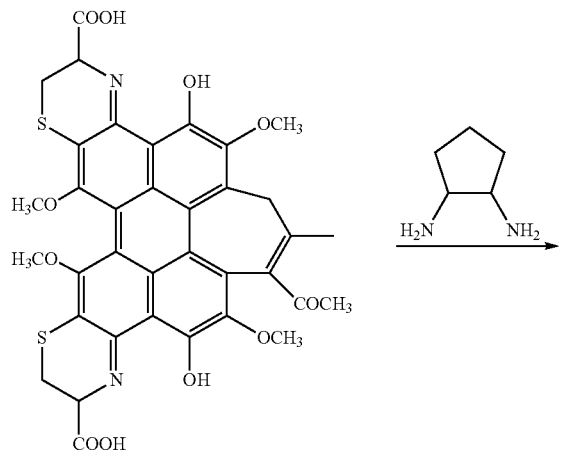

14

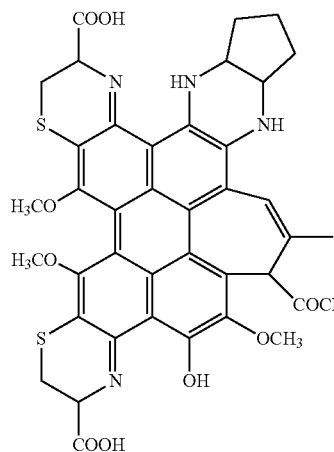

II-6

Please refer to Example 85 for the synthesis of a compound II-6: yield: 10.5%; MS (ESI+), m/z $C_{40}H_{36}N_4O_9S_2$, [M+H]$^+$=781.2; maximum UV absorption wavelength: $\lambda_{max}$ (log ε), 730 nm (4.2).

Example 90

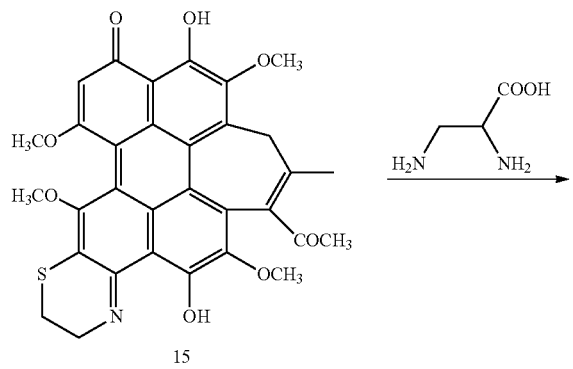

15

-continued

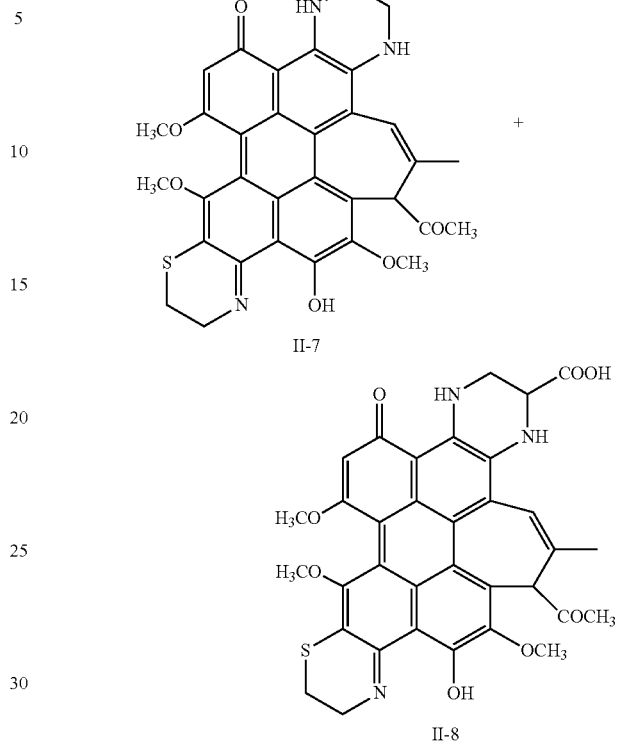

II-7

II-8

Please refer to Example 68 for the synthesis of a compound 15. Please refer to Example 85 for the synthesis of compounds II-7 and II-8. II-7: yield: 15.9%; MS (ESI+), m/z $C_{34}H_{29}N_3O_8S$, [M+H]$^+$=640.2; maximum UV absorption wavelength: $\lambda_{max}$ (log ε), 715 nm (4.4). II-8: yield: 17.4%; MS (ESI+), m/z $C_{34}H_{29}N_3O_8S$, [M+H]$^+$=640.2; maximum UV absorption wavelength: $\lambda_{max}$ (log ε), 715 nm (4.4).

Example 91

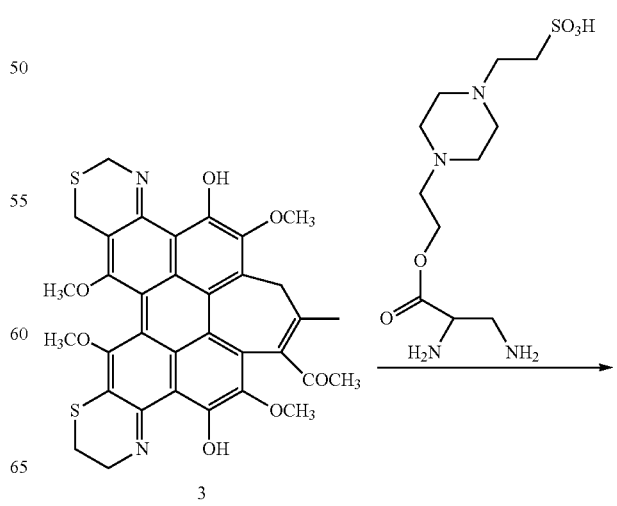

3

-continued

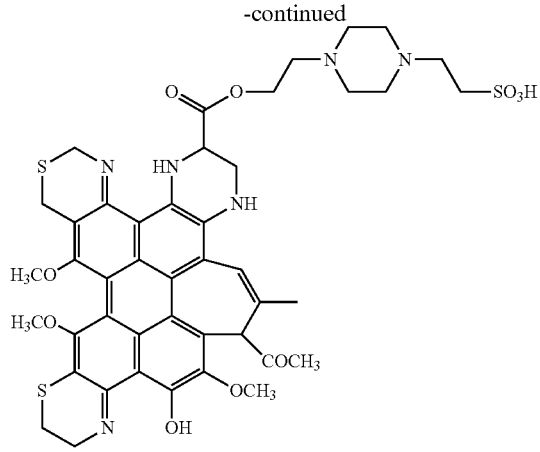

II-9

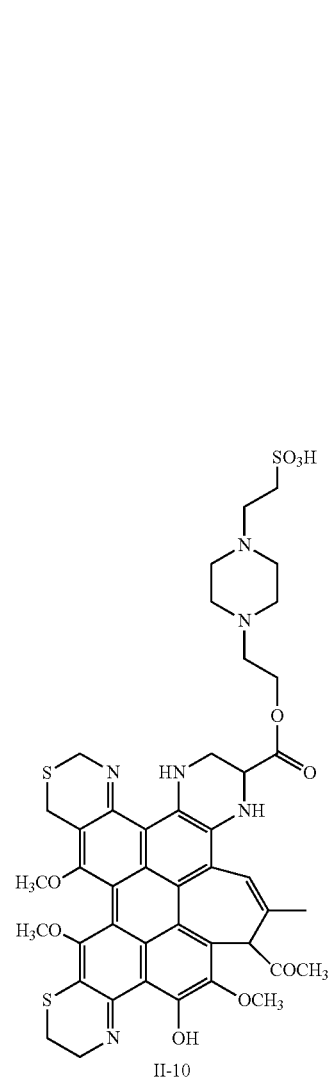

II-10

Example 92

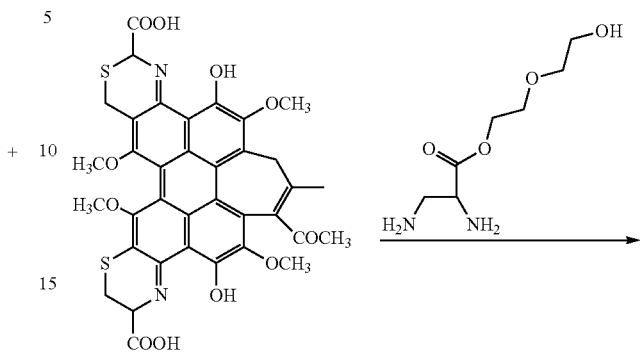

14

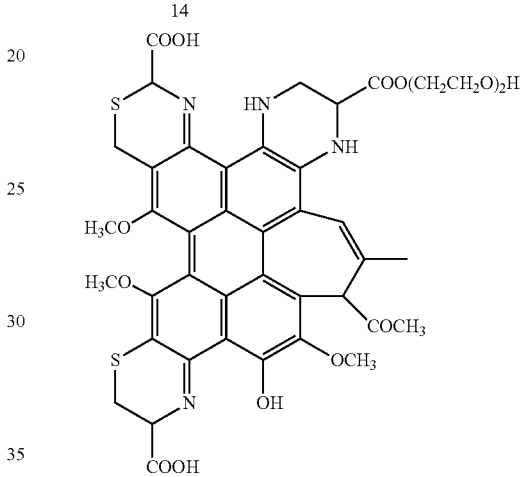

II-11

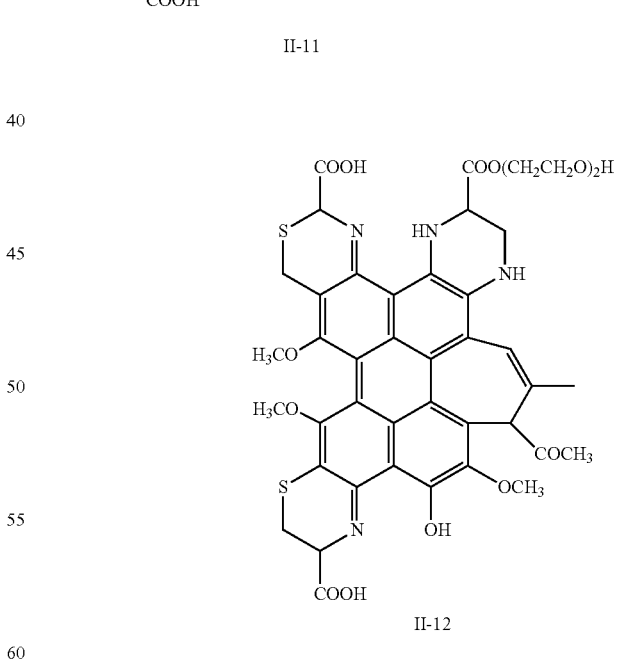

II-12

Please refer to Example 86 for the synthesis of compounds II-9 and II-10. II-9: yield: 9.9%; MS (ESI+), m/z $C_{44}H_{48}N_6O_{10}S_3$, $[M+H]^+=917.2$; maximum UV absorption wavelength: $\lambda_{max}$ (log ε), 734 nm (4.2). II-10: yield: 10.4%; MS (ESI+), m/z $C_{44}H_{48}N_6O_{10}S_3$, $[M+H]^+=917.2$; maximum UV absorption wavelength: $\lambda_{max}$ (log ε), 734 nm (4.2).

Please refer to Example 86 for the synthesis of compounds II-11 and II-12. II-11: yield: 10.0%; MS (ESI+), m/z $C_{42}H_{40}N_4O_{13}S_2$, $[M+H]^+=873.2$; maximum UV absorption wavelength: $\lambda_{max}$ (log ε), 735 nm (4.3). 11-12: yield: 9.6%; MS (ESI+), m/z $C_{42}H_{40}N_4O_{13}S_2$, $[M+H]^+=873.2$; maximum UV absorption wavelength: $\lambda_{max}$ (log ε), 735 nm (4.3).

Example 93

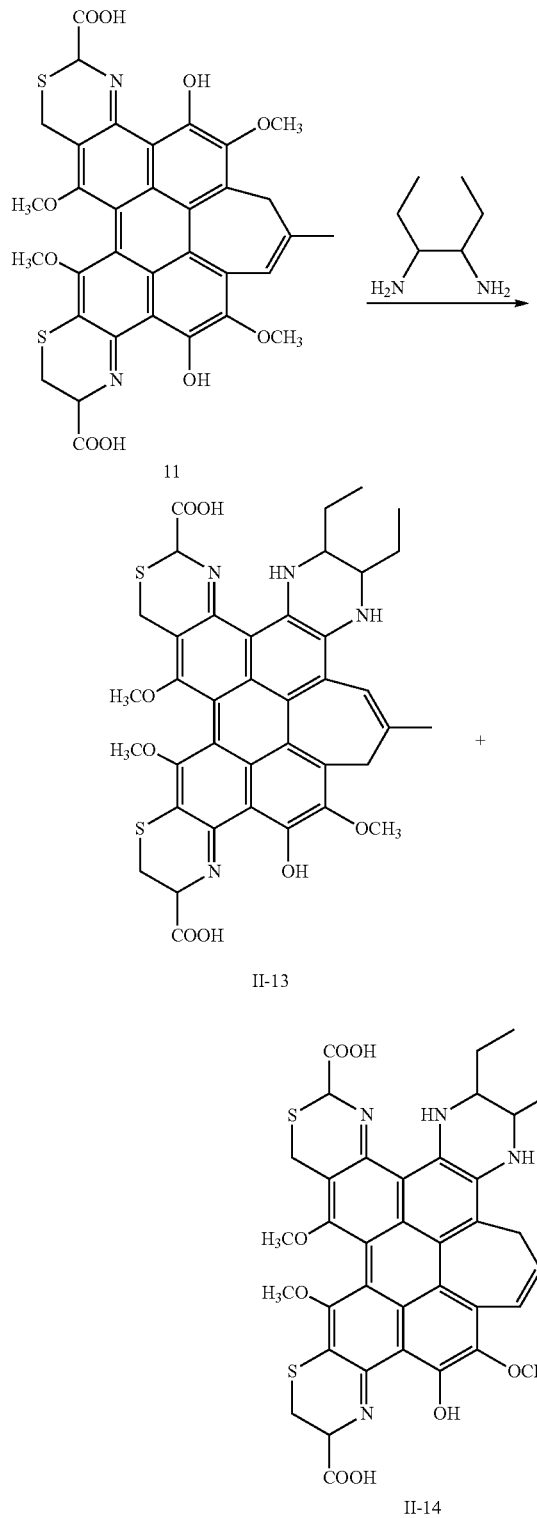

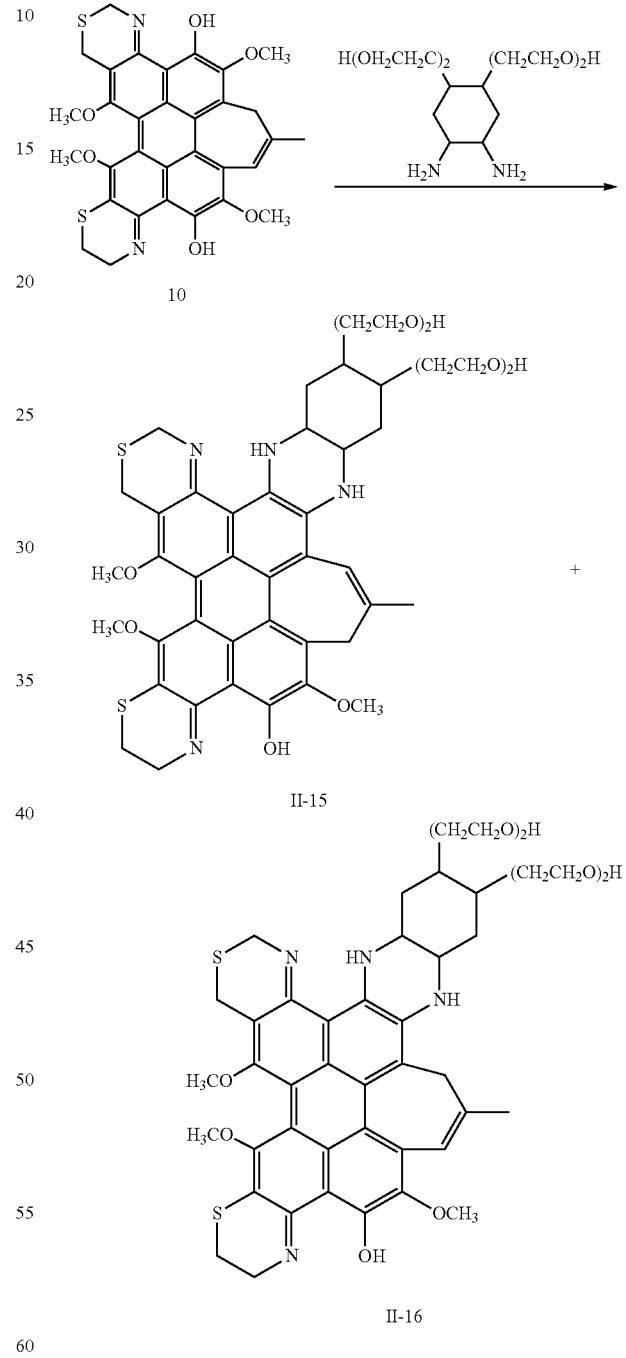

Example 94

Please refer to Example 87 for the synthesis of compounds 11-13 and 11-14. 11-13: yield: 12.7%; MS (ESI+), m/z $C_{39}H_{38}N_4O_8S_2$, $[M+H]^+=755.2$; maximum UV absorption wavelength: $\lambda_{max}$ (log ε), 732 nm (4.0). 11-14: yield: 10.9%; MS (ESI+), m/z $C_{39}H_{38}N_4O_8S_2$, $[M+H]^+=755.2$; maximum UV absorption wavelength: $\lambda_{max}$ (log ε), 732 nm (4.0).

Please refer to Example 87 for the synthesis of compounds II-15 and II-16. II-15: yield: 8.2%; MS (ESI+), m/z $C_{45}H_{52}N_4O_8S_2$, $[M+H]^+=841.3$; maximum UV absorption wavelength: $\lambda_{max}$ (log ε), 731 nm (4.0). II-16: yield: 7.6%; MS (ESI+), m/z $C_{45}H_{52}N_4O_8S_2$, $[M+H]^+=841.3$; maximum UV absorption wavelength: $\lambda_{max}$ (log ε), 731 nm (4.0).

Example 95

Figure 10:
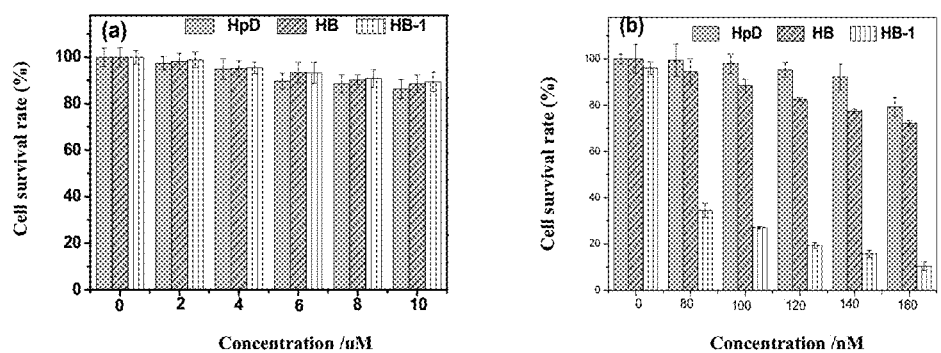
FIG. 10 shows the Hela cell dark toxicity (a) and phototoxicity (b) of different concentrations of a hematoporphyrin derivative HpD, hypocrellin B (HB), and a PEG-containing hypocrellin derivative HB-1 according to Example 3 of the invention.
Figure 11:
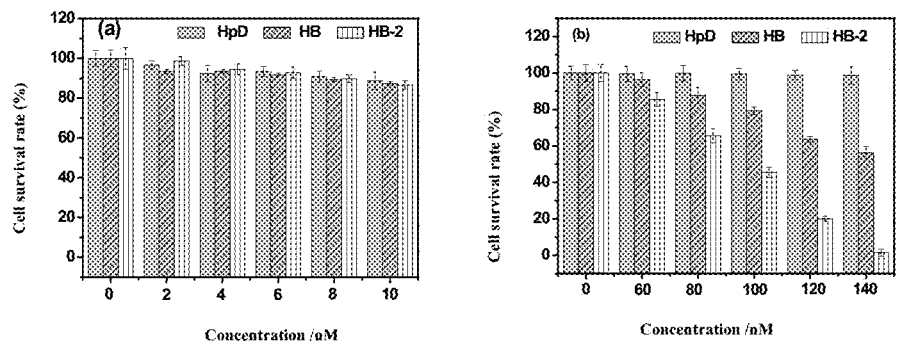
FIG. 11 shows the Hela cell dark toxicity (a) and phototoxicity (b) of different concentrations of a hematoporphyrin derivative HpD, hypocrellin B (HB), and a PEG-containing hypocrellin derivative HB-2 according to Example 3 of the invention.
Figure 12:
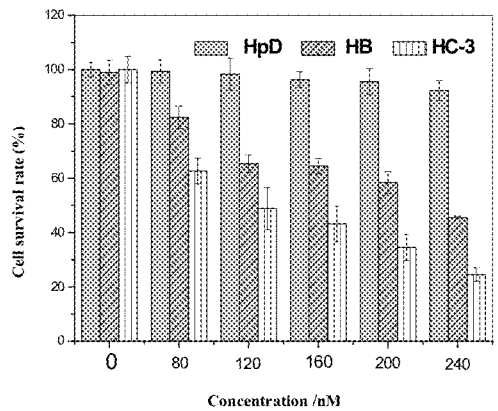
FIG. 12 shows the Hela cell phototoxicity of different concentrations of a hematoporphyrin derivative HpD, hypocrellin B (HB), and an aminopropanol-modified deacetylated hypocrellin derivative HC-3 or HC-4 synthesized in Example 4 of the invention.
Figure 13:
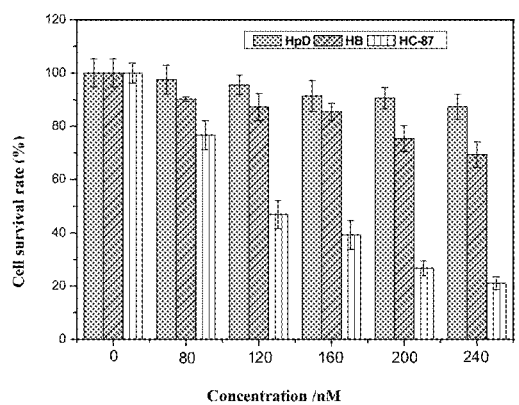
FIG. 13 shows the Hela cell phototoxicity of different concentrations of a hematoporphyrin derivative HpD, hypocrellin B (HB), and a deacetylated hypocrellin derivative HC-87 or HC-88 modified with a long chain quaternary ammonium salt synthesized in Example 46 of the invention.
Figure 14:
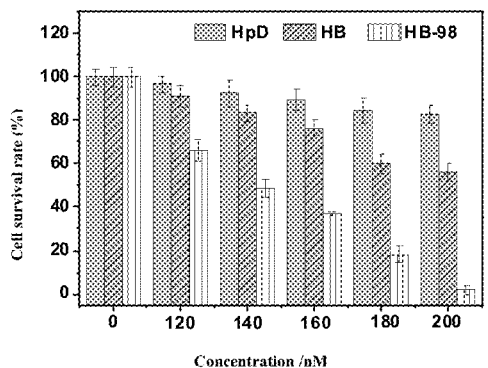
FIG. 14 shows the Hela cell phototoxicity of different concentrations of a hematoporphyrin derivative HpD, hypocrellin B (HB) and a piperazinohypocrellin B derivative HB-98 according to Example 52 of the invention.
Figure 15:
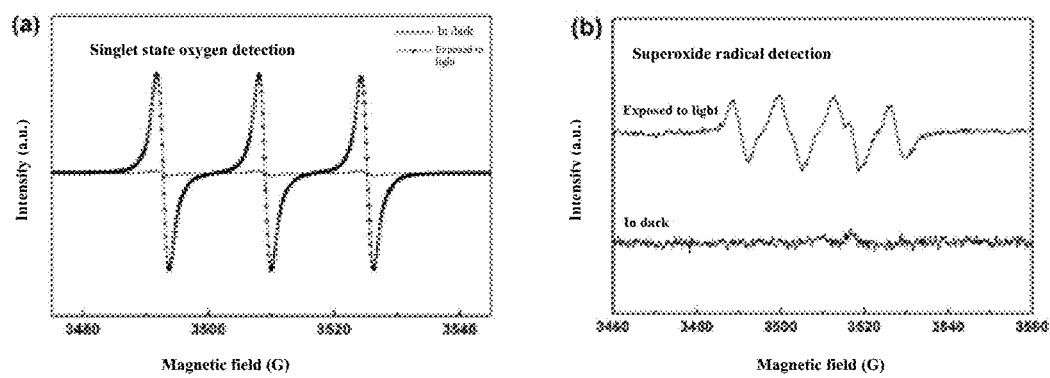
FIG. 15a shows the reaction of a hypocrellin derivative I-1 according to Example 67 of the invention with a singlet state oxygen scavenger.
FIG. 15b shows the reaction of a hypocrellin derivative I-1 according to Example 67 of the invention with a superoxide radical scavenger.

Dark Cytotoxicity Experiment:

Cultured Hela cells were digested and percussed with 0.25% trypsin, made into a single cell suspension, adjusted to a cell count of about $2 \times 10^4$/mL, inoculated into a 96-well culture plate with 200 uL/well, and cultured in an incubator with a 5% $CO_2$ environment at 37° C. After cells were adherent, the supernatant culture solution was discarded, different concentrations of photosensitizers (hematoporphyrin derivative HpD, HB, and hypocrellin derivative HB-1) were added strictly in dark according to the experiment design, and further incubated in an incubator with a 5% $CO_2$ environment at 37° C. for another 1 h. The survival rate of cells was detected by MTT assay. 20 uL of MTT (prepared with PBS, concentration: 5 mg/mL) was added to each well, and further incubated in an incubator with a 5% $CO_2$ environment at 37° C. for another 4 h. Then the incubation was terminated. The supernatant was carefully pipetted from the wells and discarded, and then 150 uL of dimethyl sulfoxide (DMSO) was added to each well. The violet crystal was fully dissolved by vibration with a microvibrator for 10 min. The optical density value (OD value) of each well was detected by an ELIASA at 570 nm wavelength to calculate the cell survival rate according to the following formula: cell survival rate=OD value of the experimental group/OD value of the blank group×100%. FIG. 10a shows the dark toxicity experiment results.

Example 96

Cell Phototoxicity Experiment:

Cultured Hela cells were digested and percussed with 0.25% trypsin, made into a single cell suspension, adjusted to a cell count of about $2 \times 10^4$/mL, inoculated into a 96-well culture plate with 200 uL/well, and cultured in an incubator with a 5% $CO_2$ environment at 37° C. After cells were adherent, the supernatant culture solution was discarded, different concentrations of photosensitizers (hematoporphyrin derivative HpD, HB, and hypocrellin derivative HB-1) were added strictly in dark according to the experiment design, and further incubated in an incubator with a 5% $CO_2$ environment at 37° C. for another 1 h. Then the 96-well culture plate was perpendicularly irradiated with uniform semiconductor laser beam at a wavelength of 635 nm with the power density adjusted to 20 mW/cm$^2$ for 1000 S. At the same time, a blank group was arranged for each 96-well culture plate, and 6 wells were arranged for each condition. After irradiation, the culture plate was further incubated in an incubator with a 5% $CO_2$ environment at 37° C. for another 24 h, and then the cell survival rate was detected. The survival rate of cells was detected by MTT assay. 20 uL of MTT (prepared with PBS, concentration: 5 mg/mL) was added to each well, and further incubated in an incubator with a 5% $CO_2$ environment at 37° C. for another 4 h. Then the incubation was terminated. The supernatant was carefully pipetted from the wells and discarded, and then 150 uL of dimethyl sulfoxide (DMSO) was added to each well. The violet crystal was fully dissolved by vibration with a microvibrator for 10 min. The optical density value (OD value) of each well was detected by an ELIASA at 570 nm wavelength to calculate the cell survival rate according to the following formula: cell survival rate=OD value of the experimental group/OD value of the blank group×100%. FIG. 10b shows the phototoxicity experiment results.

Comparison Example 1

Figure 5:
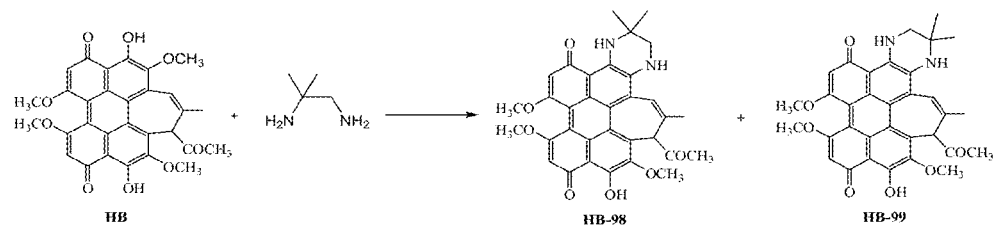
FIG. 5 shows a synthesis reaction route map of piperazinohypocrellin B derivatives HB-98 and HB-99 according to Example 52 of the invention.
Figure 6:
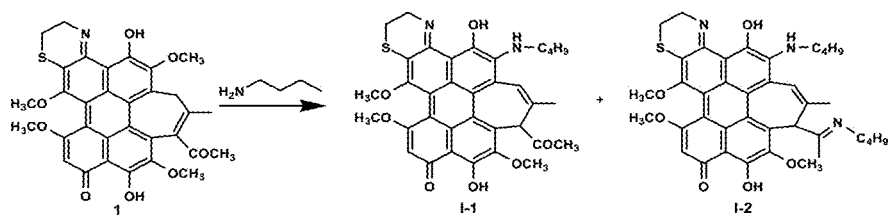
FIG. 6 shows a synthesis reaction route map of polysubstituted hypocrellin B derivatives I-1 and I-2 according to Example 67 of the invention.
Figure 7:
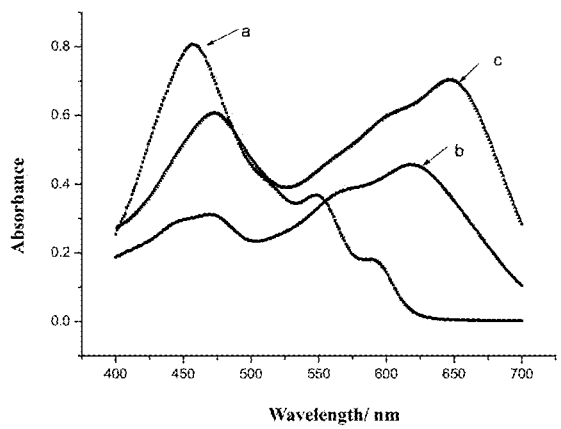
FIG. 7 shows the comparison of the absorption spectra of hypocrellin B (HB) (a) extracted in Example 1, a PEG-containing hypocrellin B derivative HB-1 (b) prepared in Example 3 and a piperazinohypocrellin B derivative HB-98 (c) prepared in Example 52 of the invention.
Figure 8:
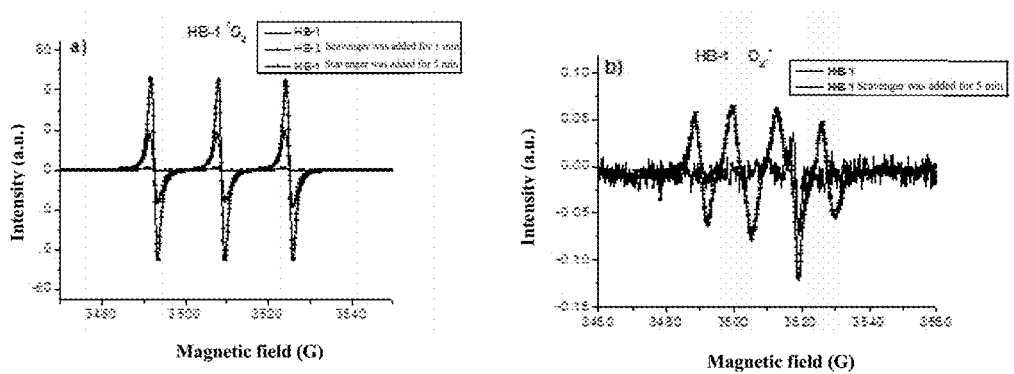
FIG. 8 shows the reactions of a PEG-containing hypocrellin derivative HB-1 according to Example 3 of the invention respectively with a singlet state oxygen scavenger (a) and a superoxide radical scavenger (b)
Figure 9:
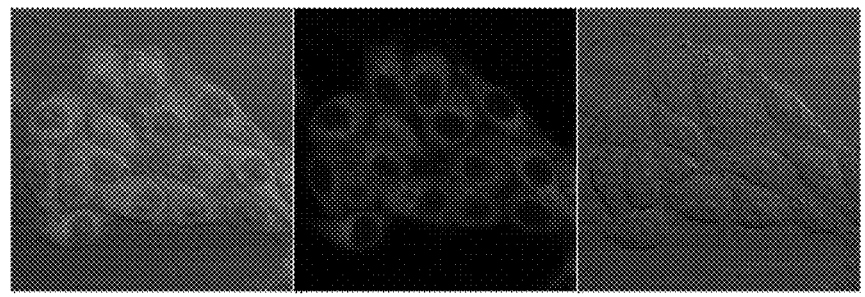
FIG. 9 shows confocal fluorescence imaging of a PEG-containing hypocrellin derivative HB-1 according to Example 3 of the invention respectively in Hela cells.

The structural formula of unmodified hypocrellin B (HB) is shown in FIG. 5, the absorption spectrum is shown in FIG. 7a, the maximum absorption wavelength is 450 nm, and there is weak red absorption at 590 nm. HB has weak light absorption capacity in the phototherapy window of 600-900 nm, and has much poorer ability to photodynamically kill tumor cells than the amphiphilic hypocrellin derivatives according to the invention (FIG. 10-14).

Comparison Example 2

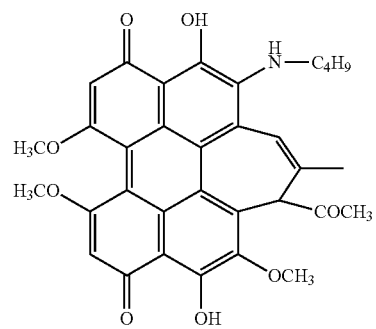

A patent No. CN1194263A discloses that a compound A has the maximum absorption at 623 nm. The maximum absorption spectrum wavelength of the hypocrellin derivative A in the comparison Example is nearly 50 nm lower when compared with the polysubstituted near infrared hypocrellin derivative I-1 prepared according to the invention.

Comparison Example 3

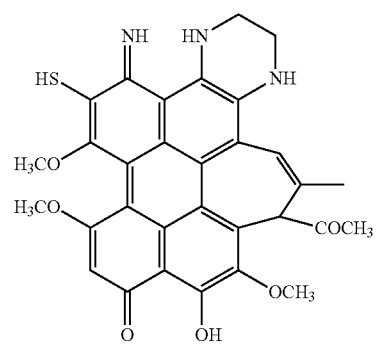

A document (Hypocrellin derivative with improvements of red absorption and active oxygen species generation, *Bioorganic & Medicinal Chemistry Letters*, 2004, 14, 1499-1501) discloses that a compound B has the maximum absorption at 640 nm. The maximum absorption spectrum wavelength of the hypocrellin derivative B in the comparison Example is nearly 50 nm lower when compared with the polysubstituted near infrared hypocrellin derivative II-2 prepared according to the invention.

Conclusions: The monosubstituted or polysubstituted amphiphilic hypocrellin derivative prepared according to the invention has an obvious red shift of its absorption spectrum and a greatly enhanced high molar extinction coefficient, and shows very strong near infrared red absorption capacity and amphiphilicity. Lack of any substitution will damage the effects of hypocrellin derivatives in some aspects to different extents.

Obviously, the above examples of the invention are only provided to clearly illustrate the invention, and rather than to limit the embodiments of the invention. For those with ordinary skills in the art, other different forms of alterations or variations may also be made on the basis of the above description. Here, it is impossible to exhaustively provide all embodiments, and all apparent alterations or variations derived from the technical solution of the invention still fall within the scope of protection of the invention.

The invention claimed is:

1. A monosubstituted or polysubstituted amphiphilic hypocrellin derivative, being represented by general structural formula (I) or (II), or their enol tautomers:

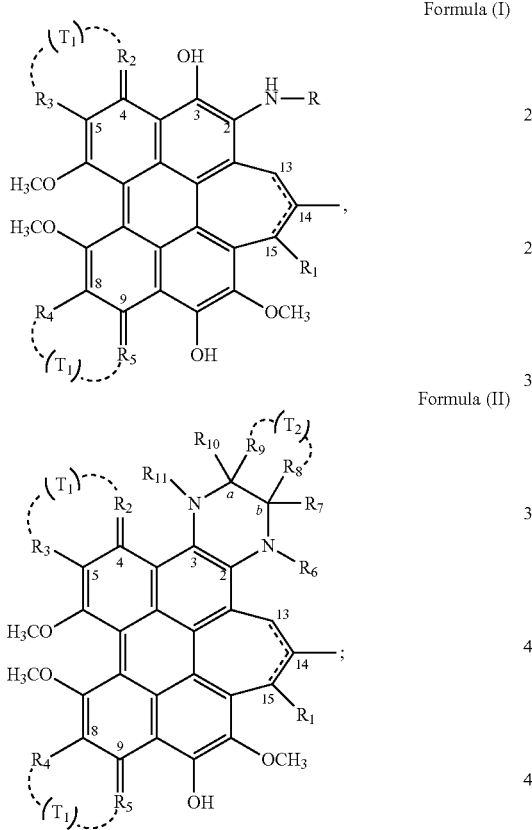

in formulas (I) and (II), $T_1$ means that neither of two adjacent $R_2$ and $R_3$ nor two adjacent $R_4$ and $R_5$ are bonded, or one group or two groups are bonded; when neither of two adjacent $R_2$ and $R_3$ nor two adjacent $R_4$ and $R_5$ are bonded, then $R_2$ and $R_5$ are oxygen, and $R_3$ and $R_4$ are hydrogen; when two adjacent $R_2$ and $R_3$ or two adjacent $R_4$ and $R_5$ are bonded, they form a substituted or unsubstituted six-membered heterocycle, wherein $T_1$ is a substituted or unsubstituted linker containing two carbon atoms, $R_2$ and $R_5$ are nitrogen, and $R_3$ and $R_4$ are sulfur; when two adjacent $R_2$ and $R_3$ are bonded and two adjacent $R_4$ and $R_5$ are not bonded, then $R_2$ and $R_3$ form a substituted or unsubstituted six-membered heterocycle, wherein $T_1$ is a substituted or unsubstituted linker containing two carbon atoms, $R_4$ is hydrogen, and $R_5$ is oxygen; and when two adjacent $R_2$ and $R_3$ are not bonded and two adjacent $R_4$ and $R_5$ are bonded, then $R_2$ is oxygen, $R_3$ is hydrogen, and $R_4$ and $R_5$ form a substituted or unsubstituted six-membered heterocycle, wherein $T_1$ is a substituted or unsubstituted linker containing two carbon atoms;

in formula (I), $R_1$ is —H, —COCH$_3$ or —C(CH$_3$)=N—R, in formula (II), $R_1$ is —H; $T_2$ means that $R_8$ and $R_9$ are bonded or not bonded; and when $R_8$ and $R_9$ are bonded, they form a substituted or unsubstituted five-membered, six-membered or seven-membered ring, wherein $T_2$ is a substituted or unsubstituted linker containing one, two or three carbon atoms;

in formula (I), the substituent R is represented by general structural formula (III):

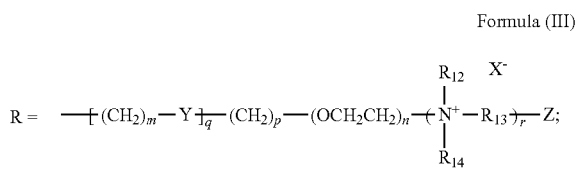

in formula (III), $0 \le m \le 12$, $0 \le n \le 500$, $0 \le p \le 12$, $0 \le q \le 12$, $0 \le r \le 1$; the m, n, p, q and r are zero or positive integers; Y is a linking group; Z is a terminal group; and (OCH$_2$CH$_2$)$_n$ is a polyethylene glycol unit;

in formula (III), the linking group Y is NH, O, S, a carboxylate, an amide, a sulfonate, an aryl, a heteroaryl, an alkyl containing 3-12 carbon atoms or a cycloalkyl containing 3-12 carbon atoms; the aryl is a substituted or unsubstituted aryl; the heteroaryl is a substituted or unsubstituted heteroaryl; the alkyl containing 3-12 carbon atoms comprises a substituted or unsubstituted or heteroatom-containing alkene or alkyne; the cycloalkyl containing 3-12 carbon atoms comprises a substituted or unsubstituted or heteroatom-containing cycloalkane, cycloalkene or cycloalkyne; the heteroatom is oxygen, nitrogen or sulfur; the substituent of said substituted Y groups is an alkyl containing 1-12 carbon atoms, an alkenyl containing 2-12 carbon atoms, an alkynyl containing 2-12 carbon atoms, a cycloalkyl containing 3-8 carbon atoms, an aryl or an aralkyl containing 6-12 carbon atoms; or an alkyl with a terminal group containing a hydroxy, a carboxy, a sulfo or a carboxylate; or an alkyl, alkenyl, alkynyl, cycloalkyl, aryl or aralkyl having a chain containing oxygen or sulfur and 1-12 carbon atoms;

in formula (III), the terminal group Z is hydrogen, an alkyl consisting essentially of 1-12 carbon atoms, an alkoxy containing 1-12 carbon atoms, a phenyl, a heterocycle, a hydroxy, a sulfhydryl, a carboxy, a carboxylate, —COOCH$_3$, —COOC$_2$H$_5$, or a sulfo or a pyridine salt;

in formula (III), when the terminal group Z is a pyridine salt, a substituent on the pyridine ring of the pyridine salt is at an ortho-position, a meta-position or a para-position; the pyridine salt is prepared by quaternization of pyridine and a halogenated hydrocarbon containing 1-12 carbon atoms of different chain lengths; and the anion of the pyridine salt is a pharmaceutically acceptable anion;

in formula (III), three substituents $R_{12}$, $R_{13}$ and $R_{14}$ of the quaternary ammonium salt are independently or completely: an alkyl containing 1-12 carbon atoms, an alkenyl containing 2-12 carbon atoms, an alkynyl containing 2-12 carbon atoms, a cycloalkyl containing 3-8 carbon atoms, a cycloalkenyl containing 3-8 carbon atoms, an aryl or an aralkyl containing 6-12 carbon atoms; or an alkyl with a terminal group containing a hydroxy, a carboxy, a sulfo or a carboxylate; or an alkyl, alkenyl, alkynyl, cycloalkyl, aryl or aralkyl having a chain containing oxygen, nitrogen or sulfur and 1-12 carbon atoms; or different combinations of the above substituents; and the anion $X^-$ of the quaternary ammonium salt is a pharmaceutically acceptable anion;

in formula (I), when neither of two adjacent $R_2$ and $R_3$ nor two adjacent $R_4$ and $R_5$ are bonded, $R_2$ and $R_5$ are oxygen, $R_3$ and $R_4$ are hydrogen, and $R_1$ is —$COCH_3$, the linking group Y in the substituent R in formula (I) is not NH;

in formula (II), each of $R_6$-$R_{11}$ on the hypocrellinopiperazine ring are represented by general structural formula (III) of the substituent R, and $R_6$-$R_{11}$ are identical or partially identical or different.

2. The monosubstituted or polysubstituted amphiphilic hypocrellin derivative according to claim 1, wherein the $T_1$ in formula (I) is absent, which is represented by general structural formula (IV):

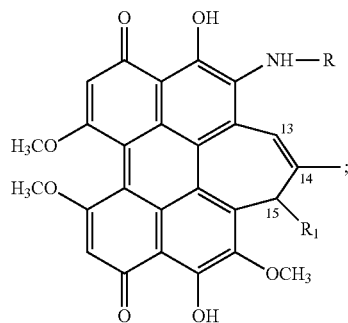

Formula (IV)

in formula (IV), the substituent $R_1$ of the hypocrellin derivative is H, —$COCH_3$ or —$C(CH_3)$=N—R;

in formula (IV), the substituent R is represented by general structural formula (III); and in formula (IV), when the $R_1$ is —$COCH_3$, the linking group Y in the substituent R is not NH.

3. The monosubstituted or polysubstituted amphiphilic hypocrellin derivative according to claim 1, wherein both of the $T_1$ and the $T_2$ in formula (II) are acyclically bonded, and is represented by general structural formula (V):

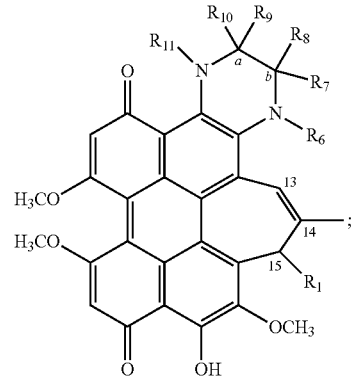

Formula (V)

in formula (II), when none of two adjacent $R_2$ and $R_3$, two adjacent $R_4$ and $R_5$ and two adjacent $R_5$ and $R_9$ of hypocrellin are bonded, $R_2$ and $R_5$ are oxygen, and $R_3$ and $R_4$ are hydrogen, it is represented by general structural formula (V);

in formula (V), the substituent $R_1$ of the piperazinohypocrellin derivative is H; and in formula (V), the substituents $R_6$-$R_{11}$ on the hypocrellinopiperazine ring are represented by general structural formula (III) of the substituent R, and $R_6$-$R_{11}$ are identical or partially identical or different.

4. The monosubstituted or polysubstituted amphiphilic hypocrellin derivative according to claim 1, wherein the $T_1$ in formula (I) and formula (II) is a substituted or unsubstituted linker containing two carbon atoms, and has a structure represented by formula (VI), each of $R_{15}$-$R_{18}$ on the hypocrellinopiperazine ring are represented by general structural formula (III) of the substituent R according to claim 1, and $R_{15}$-$R_{18}$ are identical or partially identical or different, and the $R_8$, the $R_9$ and the $T_2$ in formula (II) form a substituted or unsubstituted five-membered, six-membered or seven-membered ring represented by formula (VII):

Formula (VI)

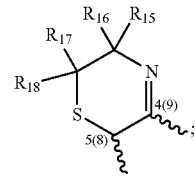

Formula (VII)

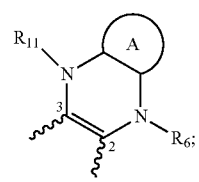

wherein ring A is a saturated or unsaturated five-membered, six-membered or seven-membered heterocycle or non-heterocycle, and the substituents thereon are independently or completely the substituent R in formula (III) according to claim 1.

5. The monosubstituted or polysubstituted amphiphilic hypocrellin derivative according to claim 1, wherein the linker Y in the substituent R is: —NH—; —O—, —S—; —COO—; CONH—; —$SO_3$—; —$C_6H_4$-(phenyl); —$C_6H_3$ ($CH_3$)—, —$C_6H_3(C_2H_5)$—; —$C_6H_3$(OH)—, —$C_6H_3$(F)—, —$C_6H_3$(Cl)—, —$C_6H_3$(Br)—, —$C_5H_3$N-(pyridyl); —$C_3H_4$-(cyclopropyl); —$C_4H_6$-(cyclobutyl); —$C_5H_8$-(cyclopentyl); —$C_5H_7(CH_3)$-(methylcyclopentyl); —$C_5H_7$(OH)-(hydroxycyclopentyl); —$C_6H_{10}$-(cyclohexyl); —$C_6H_9(CH_3)$-(methylcyclohexyl); —$C_6H_9(C_2H_5)$-(ethylcyclohexyl); —$C_6H_9(C_3H_7)$-(propylcyclohexyl); —$C_6H_9$($C_4H_9$)-(butylcyclohexyl); —$C_6H_8(CH_3)_2$-(dimethylcyclohexyl); —$C_6H_9$(OH)-(hydroxycyclohexyl); —$C_7H_{12}$-(cycloheptyl);

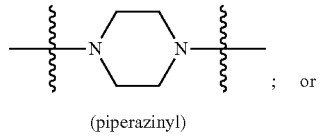

(piperazinyl)

; or

-continued

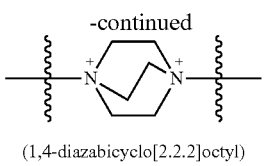

(1,4-diazabicyclo[2.2.2]octyl)

6. The monosubstituted or polysubstituted amphiphilic hypocrellin derivative according to claim 1, wherein the terminal group Z in the substituent R is: —H; —CH$_3$; —C$_2$H$_5$, —C$_3$H$_7$, —C$_4$H$_9$; —C$_5$H$_{11}$, —C$_6$H$_{13}$; —OCH$_3$; —OC$_2$H$_5$, —OC$_3$H$_7$, —OC$_4$H$_9$, —OC$_5$H$_{11}$; —OC$_6$H$_{13}$; —C$_6$H$_5$, pyridyl; —OH, —SH, —COOH; —COOCH$_3$, —COOC$_2$H$_5$, —SO$_3$H; or a pyridine salt with a pharmaceutically acceptable anion and wherein the quaternary ammonium group in the substituent R is: —N$^-$(CH$_3$)$_3$; —N$^-$(C$_2$H$_5$)$_3$; —N$^-$(C$_3$H$_7$)$_3$; —N$^-$(C$_4$H$_9$)$_3$; —N$^-$(C$_5$H$_{11}$)$_3$; —N$^-$(C$_6$H$_{13}$)$_3$; —N$^-$(CH$_3$)$_2$(C$_2$H$_5$); —N$^-$(CH$_3$)$_2$(C$_3$H$_7$); —N$^-$(CH$_3$)$_2$(C$_4$H$_9$); —N$^-$(CH$_3$)$_2$(C$_5$H$_{11}$); —N$^-$(CH$_3$)$_2$(C$_6$H$_{13}$); —N$^-$(CH$_3$)$_2$(C$_7$H$_{15}$); —N$^-$(CH$_3$)$_2$(C$_8$H$_{17}$); —N$^-$(CH$_3$)$_2$(C$_9$H$_{19}$); —N$^-$(CH$_3$)$_2$(C$_{10}$H$_{23}$); —N$^-$(CH$_3$)$_2$(C$_{11}$H$_{23}$); —N$^-$(CH$_3$)$_2$C$_{12}$H$_{25}$); —N$^-$(C$_2$H$_5$)$_2$(C$_3$H$_7$); —N$^-$(C$_2$H$_5$)$_2$(C$_4$H$_9$); —N$^-$(C$_2$H$_5$)$_2$(C$_5$H$_{11}$); —N$^-$(C$_2$H$_5$)$_2$(C$_6$H$_{13}$); —N$^-$(C$_2$H$_5$)$_2$(C$_7$H$_{15}$); —N$^-$(C$_2$H$_5$)$_2$(C$_8$H$_{17}$); —N$^-$(C$_2$H$_5$)$_2$(C$_9$H$_{19}$); —N$^-$(C$_2$H$_5$)$_2$(C$_{10}$H$_{23}$); —N$^-$(C$_2$H$_5$)$_2$(C$_{11}$H$_{23}$); or —N$^+$(C$_2$H$_5$)$_2$(C$_{12}$H$_{25}$).

7. The monosubstituted or polysubstituted amphiphilic hypocrellin derivative according to claim 1, wherein the general structural formula of the hypocrellin derivative is an enol tautomer represented by formula (I') or formula (I):

Formula I'

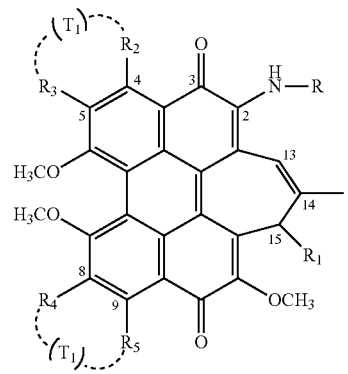

-continued

Formula II'

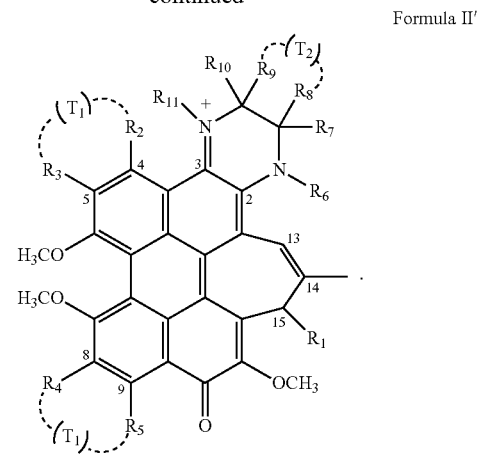

8. A method for preparing the monosubstituted or polysubstituted amphiphilic hypocrellin derivative according to claim 2 or 3, comprising the following steps:
mixing hypocrellin B and a corresponding substituted amino derivative at a molar ratio of 1:5-50 in an organic solvent, which is one or more of acetonitrile, tetrahydrofuran, pyridine, methanol and ethanol, keeping the resulting solution in dark at a reaction temperature of 20-100° C. under the protection of an inert gas for 6-18 h, and purifying the product by separation to obtain the amphiphilic hypocrellin derivative in formula (IV) or formula (V).

9. A method for preparing the monosubstituted or polysubstituted amphiphilic hypocrellin derivative according to claim 4, comprising the following steps:
mixing hypocrellin B or deacetylated hypocrellin B and a corresponding substituted thioethylamine derivative at a molar ratio of 1:50-500 in a mixed solvent of an organic solvent and water, illuminating the resulting solution with light at a wavelength>450 nm at room temperature at pH>9 for 10-40 min, and purifying the product by separation to obtain a 4,5-substituted, 8,9-substituted or 4,5,8,9-substituted hypocrellin derivative; and
mixing the hypocrellin derivative and a corresponding substituted amino derivative at a molar ratio of 1:5-50 in an organic solvent, keeping the resulting solution in dark at a reaction temperature of 20-150° C. under the protection of an inert gas for 4-20 h, and obtaining the corresponding polysubstituted hypocrellin derivative in formula (VI) or formula (VII) by separation and purification of the product.

10. A photodynamic drug for use in photodynamic therapy including the monosubstituted or polysubstituted amphiphilic hypocrellin derivative according to claim 1.

* * * * *